United States Patent
Qi et al.

(10) Patent No.: US 12,077,539 B2
(45) Date of Patent: Sep. 3, 2024

(54) IMIDAZOLE AND TRIAZOLE KRAS INHIBITORS

(71) Applicant: Incyte Corporation, Wilmington, DE (US)

(72) Inventors: Chao Qi, Wilmington, DE (US); Xiaozhao Wang, Mt. Laurel, NJ (US); Wenqing Yao, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 17/700,923

(22) Filed: Mar. 22, 2022

(65) Prior Publication Data

US 2022/0306633 A1  Sep. 29, 2022

Related U.S. Application Data

(60) Provisional application No. 63/164,042, filed on Mar. 22, 2021.

(51) Int. Cl.
| | |
|---|---|
| *C07D 471/14* | (2006.01) |
| *A61K 31/4375* | (2006.01) |
| *A61P 35/00* | (2006.01) |

(52) U.S. Cl.
CPC .......... *C07D 471/14* (2013.01); *A61P 35/00* (2018.01)

(58) Field of Classification Search
CPC ............. C07D 471/14; A61K 31/4375; A61P 35/00; A61P 29/00; A61P 37/00
USPC ............................................. 546/82; 514/293
See application file for complete search history.

(56) References Cited

U.S. PATENT DOCUMENTS

| | | |
|---|---|---|
| 7,592,453 B2 | 9/2009 | Kajino et al. |
| 7,897,609 B2 | 3/2011 | Niwas et al. |
| 8,034,802 B2 | 10/2011 | Averett |
| 8,143,270 B2 | 3/2012 | Kshirsagar et al. |
| 8,158,794 B2 | 4/2012 | Kshirsagar et al. |
| 8,207,187 B2 | 6/2012 | Beck et al. |
| 8,513,250 B2 | 8/2013 | Escaich et al. |
| 8,557,984 B2 | 10/2013 | Bouillot et al. |
| 8,563,565 B2 | 10/2013 | Norimine et al. |
| 8,637,670 B2 | 1/2014 | Kumar et al. |
| 8,658,666 B2 | 2/2014 | Rice et al. |
| 8,846,710 B2 | 9/2014 | Kshirsagar et al. |
| 8,895,581 B2 | 11/2014 | McConnell et al. |
| 9,062,046 B2 | 6/2015 | Kumar et al. |
| 9,169,246 B2 | 10/2015 | Benazet et al. |
| 9,550,776 B2 | 1/2017 | Norimine et al. |
| 9,573,947 B2 | 2/2017 | Ozaki |
| 9,694,006 B2 | 7/2017 | Beck et al. |
| 9,771,327 B2 | 9/2017 | Zawistoski et al. |
| 9,873,694 B2 | 1/2018 | Lipford et al. |
| 10,039,753 B2 | 8/2018 | Coffman et al. |
| 10,544,138 B2 | 1/2020 | Gray et al. |
| 11,053,240 B2 | 7/2021 | Li et al. |
| 2011/0230476 A1 | 9/2011 | Niu et al. |
| 2012/0065187 A1 | 3/2012 | Borchardt et al. |
| 2012/0108627 A1 | 5/2012 | Kumar et al. |
| 2012/0232074 A1 | 9/2012 | Bouillot et al. |
| 2014/0243286 A1 | 8/2014 | Arnold et al. |
| 2016/0264570 A1 | 9/2016 | McKew et al. |
| 2017/0217960 A1 | 8/2017 | Ferguson |
| 2017/0197945 A1 | 9/2017 | Li et al. |
| 2017/0294489 A1 | 10/2017 | Lim et al. |
| 2019/0144444 A1 | 5/2019 | Blake et al. |
| 2019/0177338 A1 | 6/2019 | Kettle et al. |
| 2019/0270743 A1 | 9/2019 | Marx et al. |
| 2021/0230162 A1 | 7/2021 | Zhao et al. |
| 2021/0269434 A1 | 9/2021 | Wang et al. |
| 2021/0308123 A1 | 10/2021 | Zhang et al. |
| 2021/0317118 A1 | 10/2021 | Zhang et al. |
| 2021/0355121 A1 | 11/2021 | Zhu et al. |
| 2021/0355141 A1 | 11/2021 | Hoang et al. |
| 2022/0064188 A1 | 3/2022 | Carlsen et al. |

FOREIGN PATENT DOCUMENTS

| | | |
|---|---|---|
| CN | 102399218 A | 4/2012 |
| CN | 103012397 B | 3/2017 |
| CN | 108003153 A | 5/2018 |

(Continued)

OTHER PUBLICATIONS

Chen et al., "Small-Molecule Inhibitors Directly Targeting KRAS as Anticancer Therapeutics", *Journal of Medicinal Chemistry* 63(3):14404-14424 (2020).

International Search Report and Written Opinion for International Application No. PCT/US2022/021303, mailed Jul. 1, 2022, 12 pages.

Kettle et al., "Covalent inhibitors of the GTPase KRAS$^{G12C}$: a review of the patent literature",*Expert Opinion on Therapeutics Patents* 30(2):103-120 (2020).

(Continued)

*Primary Examiner* — Charanjit Aulakh
(74) *Attorney, Agent, or Firm* — Lathrop GPM LLP; Brian C. Trinque; Nicole Sassu

(57) ABSTRACT

Disclosed are compounds of Formula I, methods of using the compounds for inhibiting KRAS activity and pharmaceutical compositions comprising such compounds. The compounds are useful in treating, preventing or ameliorating diseases or disorders associated with KRAS activity such as cancer.

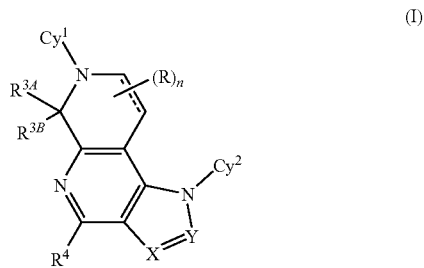

(I)

42 Claims, No Drawings

(56) References Cited

FOREIGN PATENT DOCUMENTS

| | | |
|---|---|---|
| EP | 2573073 B1 | 10/2014 |
| IN | 2012MU02281 A | 6/2012 |
| WO | WO 2008056151 A1 | 5/2007 |
| WO | WO 2007/143526 A2 | 12/2007 |
| WO | WO 2009/123967 A1 | 10/2009 |
| WO | WO 2010049366 A1 | 5/2010 |
| WO | WO 2010135571 A1 | 11/2010 |
| WO | WO 2011031896 A2 | 3/2011 |
| WO | WO 2012/011642 A1 | 1/2012 |
| WO | WO 2012154731 A1 | 11/2012 |
| WO | WO 2016168540 A1 | 10/2016 |
| WO | WO 2016161361 | 12/2016 |
| WO | WO 2016199943 A1 | 12/2016 |
| WO | WO 2017058805 A1 | 4/2017 |
| WO | WO 2017/092413 A1 | 6/2017 |
| WO | WO 2017/201161 | 11/2017 |
| WO | WO 2018119183 A2 | 6/2018 |
| WO | WO 2018217651 A1 | 11/2018 |
| WO | WO 2019201283 A1 | 10/2019 |
| WO | WO 2019209896 A1 | 10/2019 |
| WO | WO 2019213516 A1 | 11/2019 |
| WO | WO 2020/055755 | 3/2020 |

OTHER PUBLICATIONS

Kettle et al., "Structure-based design and pharmacokinetic optimization of covalent allosteric inhibitors of the mutant GTPase $KRAS^{G12C}$", *Journal of Medicinal Chemistry* 63(9):4468-4483 (Feb. 2020).

Kim et al., "Targeting KRAS (G12C): From Inhibitory Mechanism to Modulation of Antitumor Effects in Patients", *Cell* 183(4):850-859 (2020).

Korzeniecki, Claudia et al.: "Targeting KRAS mutant cancers by preventing signaling transduction in the MAPK pathway", European Journal of Medicinal Chemistry, Elsevier, Amsterdam, NL, vol. 211, Nov. 17, 2020.

Zhu Jian et al: "Structure-based discovery of selective BRPFI bromodomain inhibitors", European Journal of Medicinal Chemistry, Elsevier, Amsterdam, NL, vol. 155, Jun. 2, 2018 (Jun. 2, 2018), pp. 337-352.

Cox et al., "Drugging the undruggable Ras: mission impossible?", *Nature Reviews Drug Discovery* 13(11):828-851 (2014).

Fernandez-Medarde et al., "Ras in Cancer and Developmental Diseases", *Genes & Cancer* 2(3):344-358 (2011).

IMIDAZOLE AND TRIAZOLE KRAS INHIBITORS

RELATED APPLICATIONS

This application claims priority to U.S. Provisional Application No. 63/164,042 filed on Mar. 22, 2021, the entire content of which are hereby incorporated by reference in its entirety.

FIELD OF THE INVENTION

The disclosure provides compounds as well as their compositions and methods of use. The compounds modulate KRAS activity and are useful in the treatment of various diseases including cancer.

BACKGROUND OF THE INVENTION

Ras proteins are part of the family of small GTPases that are activated by growth factors and various extracellular stimuli. The Ras family regulates intracellular signaling pathways responsible for growth, migration, survival and differentiation of cells. Activation of RAS proteins at the cell membrane results in the binding of key effectors and initiation of a cascade of intracellular signaling pathways within the cell, including the RAF and PI3K kinase pathways. Somatic mutations in RAS may result in uncontrolled cell growth and malignant transformation while the activation of RAS proteins is tightly regulated in normal cells (Simanshu, D. et al. Cell 170.1 (2017):17-33).

The Ras family is comprised of three members: KRAS, NRAS and HRAS. RAS mutant cancers account for about 25% of human cancers. KRAS is the most frequently mutated isoform accounting for 85% of all RAS mutations whereas NRAS and HRAS are found mutated in 12% and 3% of all Ras mutant cancers respectively (Simanshu, D. et al. Cell 170.1 (2017):17-33). KRAS mutations are prevalent amongst the top three most deadly cancer types: pancreatic (97%), colorectal (44%), and lung (30%) (Cox, A. D. et al. Nat. Rev. Drug Discov. (2014) 13:828-51). The majority of RAS mutations occur at amino acid residue 12, 13, and 61. The frequency of specific mutations varies between RAS gene isoforms and while G12 and Q61 mutations are predominant in KRAS and NRAS respectively, G12, G13 and Q61 mutations are most frequent in HRAS. Furthermore, the spectrum of mutations in a RAS isoform differs between cancer types. For example, KRAS G12D mutations predominate in pancreatic cancers (51%), followed by colorectal adenocarcinomas (45%) and lung cancers (17%) while KRAS G12 V mutations are associated with pancreatic cancers (30%), followed by colorectal adenocarcinomas (27%) and lung adenocarcinomas (23%) (Cox, A. D. et al. Nat Rev Drug Discov (2014) 13:828-51). In contrast, KRAS G12C mutations predominate in non-small cell lung cancer (NSCLC) comprising 11-16% of lung adenocarcinomas, and 2-5% of pancreatic and colorectal adenocarcinomas (Cox, A. D. et al. Nat. Rev. Drug Discov. (2014) 13:828-51). Genomic studies across hundreds of cancer cell lines have demonstrated that cancer cells harboring KRAS mutations are highly dependent on KRAS function for cell growth and survival (McDonald, R. et al. Cell 170 (2017): 577-592). The role of mutant KRAS as an oncogenic driver is further supported by extensive in vivo experimental evidence showing mutant KRAS is required for early tumour onset and maintenance in animal models (Cox, A. D. et al. Nat Rev Drug Discov (2014) 13:828-51).

Taken together, these findings suggest that KRAS mutations play a critical role in human cancers; development of inhibitors targeting mutant KRAS may therefore be useful in the clinical treatment of diseases that are characterized by a KRAS mutation.

SUMMARY

The present disclosure provides, inter alia, a compound of Formula I:

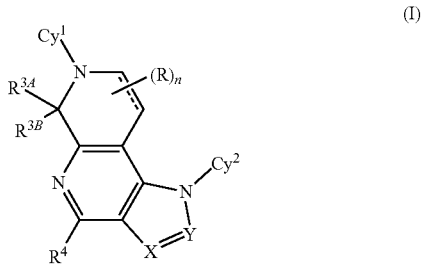

(I)

or a pharmaceutically acceptable salt thereof, wherein constituent variables are defined herein.

The present disclosure further provides a pharmaceutical composition comprising a compound of the disclosure, or a pharmaceutically acceptable salt thereof, and at least one pharmaceutically acceptable carrier or excipient.

The present disclosure further provides methods of inhibiting KRAS activity, which comprises administering to an individual a compound of the disclosure, or a pharmaceutically acceptable salt thereof. The present disclosure also provides uses of the compounds described herein in the manufacture of a medicament for use in therapy. The present disclosure also provides the compounds described herein for use in therapy.

The present disclosure further provides methods of treating a disease or disorder in a patient comprising administering to the patient a therapeutically effective amount of a compound of the disclosure, or a pharmaceutically acceptable salt thereof.

DETAILED DESCRIPTION

Compounds

In an aspect, provided herein is a compound of Formula I:

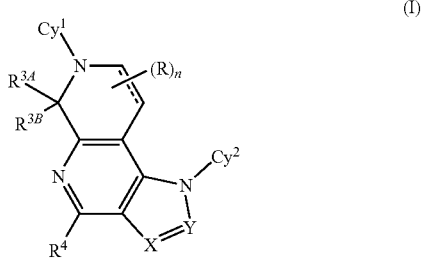

(I)

or a pharmaceutically acceptable salt thereof,
wherein:
≡ represents a single bond or a double bond;
X is N or $CR^5$;

Y is N or $CR^6$;

each R is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NOR^a)R^b$, $C(=NR^e)NR^cR^d$, $NR^cC(=NR^e)NR^cR^d$, $NR^cC(=NR^e)R^b$, $NR^cS(O)R^b$, $NR^cS(O)_2R^b$, $NR^cS(O)_2NR^cR^d$, $S(O)R^b$, $S(O)NR^cR^d$, $S(O)_2R^b$, $S(O)_2NR^cR^d$, and $BR^hR^i$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

n is 0, 1, 2, 3, or 4;

$Cy^1$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

$R^{3A}$ and $R^{3B}$ are each independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NOR^{a3})R^{b3}$, $C(=NR^{e3})NR^{c3}R^{d3}$, $NR^{c3}C(=NR^{e3})NR^{c3}R^{d3}$, $NR^{c3}C(=NR^{e3})R^{b3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$, and $BR^{h3}R^{i3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{30}$;

or $R^{3A}$ and $R^{3B}$ can be taken together with the carbon atom to which they are attached to form a C=O;

$R^4$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{i4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NOR^{a4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, and $BR^{h4}R^{i4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{40}$;

$R^5$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NOR^{a5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, and $BR^{h5}R^{i5}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{50}$;

$R^6$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOR^{a6})R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, and $BR^{h6}R^{i6}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{60}$;

$Cy^2$ is selected from $C_{3-10}$ cycloalkyl, 4-14 membered heterocycloalkyl, $C_{6-10}$ aryl and 5-10 membered heteroaryl; wherein the 4-14 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-14 membered heterocycloalkyl is optionally substituted by oxo to form a carbonyl group; and wherein the $C_{3-10}$ cycloalkyl, 4-14 membered heterocycloalkyl, $C_{6-10}$ aryl and 5-10 membered heteroaryl are each optionally substituted with 1, 2, 3 or 4 substituents independently selected from $R^{20}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a10}$, $SR^{a10}$, $C(O)R^{b10}$, $C(O)NR^{c10}R^{d10}$, $C(O)OR^{a10}$, $OC(O)R^{b10}$, $OC(O)NR^{c10}R^{d10}$, $NR^{c10}R^{d10}$, $NR^{c10}C(O)R^{b10}$, $NR^{c10}C(O)OR^{a10}$, $NR^{c10}C(O)NR^{c10}R^{d10}$, $C(=NR^{e10})R^{b10}$, $C(=NOR^{a10})R^{b10}$, $C(=NR^{e10})NR^{c10}R^{d10}$, $NR^{c10}C(=NR^{e10})NR^{c10}R^{d10}$, $NR^{c10}S(O)R^{b10}$, $NR^{c10}S(O)_2R^{b10}$, $NR^{c10}S(O)_2NR^{c10}R^{d10}$, $S(O)R^{b10}$, $S(O)NR^{c10}R^{d10}$, $S(O)_2R^{b10}$, $S(O)_2NR^{c10}R^{d10}$, and $BR^{h10}R^{i10}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, and $BR^{h11}R^{i11}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a12}$, $SR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$, and $BR^{h12}R^{i12}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a20}$, $SR^{a20}$, $C(O)R^{b20}$, $C(O)NR^{c20}R^{d20}$, $C(O)OR^{a20}$, $OC(O)R^{b20}$, $OC(O)NR^{c20}R^{d20}$, $NR^{c20}R^{d20}$, $NR^{c20}C(O)R^{b20}$, $NR^{c20}C(O)NR^{c20}R^{d20}$, $OR^{a20}$, $NR^{c20}C(O)NR^{c20}R^{d20}$, $C(=NR^{e20})R^{b20}$, $C(=NOR^{a20})R^{b20}$, $C(=NR^{e20})NR^{c20}R^{d20}$, $NR^{c20}C(=NR^{e20})NR^{c20}R^{d20}$, $NR^{c20}S(O)R^{b20}$, $NR^{c20}S(O)_2R^{b20}$, $NR^{c20}S(O)_2NR^{c20}R^{d20}$, $S(O)R^{b20}$, $S(O)NR^{c20}R^{d20}$, $S(O)_2R^{b20}$, $S(O)_2NR^{c20}R^{d20}$, and $BR^{h20}R^{i20}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, and $BR^{h21}R^{i21}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^g$;

each $R^{22}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a22}$, $SR^{a22}$, $C(O)R^{b22}$, $C(O)NR^{c22}R^{d22}$, $C(O)OR^{a22}$, $OC(O)R^{b22}$, $OC(O)NR^{c22}R^{d22}$, $NR^{c22}R^{d22}$, $NR^{c22}C(O)R^{b22}$, $NR^{c22}C(O)OR^{a22}$, $NR^{c22}C(O)NR^{c22}R^{d22}$, $NR^{c22}S(O)R^{b22}$, $NR^{c22}S(O)_2R^{b22}$, $NR^{c22}S(O)_2NR^{c22}R^{d22}$, $S(O)R^{b22}$, $S(O)NR^{c22}R^{d22}$, $S(O)_2R^{b22}$, $S(O)_2NR^{c22}R^{d22}$, and $BR^{h22}R^{i22}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{23}$;

each $R^{23}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a23}$, $SR^{a23}$, $C(O)R^{b23}$, $C(O)NR^{c23}R^{d23}$, $C(O)OR^{a23}$, $OC(O)R^{b23}$, $OC(O)NR^{c23}R^{d23}$, $NR^{c23}R^{d23}$, $NR^{c23}C(O)R^{b23}$, $NR^{c23}C(O)OR^{a23}$, $NR^{c23}C(O)NR^{c23}R^{d23}$, $NR^{c23}S(O)R^{b23}$, $NR^{c23}S(O)_2R^{b23}$, $NR^{c23}S(O)_2NR^{c23}R^{d23}$, $S(O)R^{b23}$, $S(O)NR^{c23}R^{d23}$, $S(O)_2R^{b23}$, $S(O)_2NR^{c23}R^{d23}$, and $BR^{h23}R^{i23}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{24}$;

each $R^{24}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a24}$, $SR^{a24}$, $C(O)R^{b24}$, $C(O)NR^{c24}R^{d24}$, $C(O)OR^{a24}$, $OC(O)R^{b24}$, $OC(O)NR^{c24}R^{d24}$, $NR^{c24}R^{d24}$, $NR^{c24}C(O)R^{b24}$, $NR^{c24}C(O)OR^{a24}$, $NR^{c24}C(O)NR^{c24}R^{d24}$, $NR^{c24}S(O)R^{b24}$, $NR^{c24}S(O)_2R^{b24}$, $NR^{c24}S(O)_2NR^{c24}R^{d24}$, $S(O)R^{b24}$, $S(O)NR^{c24}R^{d24}$, $S(O)_2R^{b24}$, $S(O)_2NR^{c24}R^{d24}$, and $BR^{h24}R^{i24}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{30}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a30}$, $SR^{a30}$, $C(O)R^{b30}$, $C(O)NR^{c30}R^{d30}$, $C(O)OR^{a30}$, $OC(O)R^{b30}$, $OC(O)NR^{c30}R^{d30}$, $NR^{c30}R^{d30}$, $NR^{c30}C(O)R^{b30}$, $NR^{c30}C(O)OR^{a30}$, $NR^{c30}C(O)NR^{c30}R^{d30}$, $NR^{c30}S(O)R^{b30}$, $NR^{c30}S(O)_2R^{b30}$, $NR^{c30}S(O)_2NR^{c30}R^{d30}$, $S(O)R^{b30}$, $S(O)NR^{c30}R^{d30}$, $S(O)_2R^{b30}$, $S(O)_2NR^{c30}R^{d30}$, and $BR^{h30}R^{i30}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{31}$;

each $R^{31}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)OR^{a31}$, $NR^{c31}C(O)NR^{c31}R^{d31}$, $NR^{c31}S(O)R^{b31}$, $NR^{c31}S(O)_2R^{b31}$, $NR^{c31}S(O)_2NR^{c31}R^{d31}$, $S(O)R^{b31}$, $S(O)NR^{c31}R^{d31}$, $S(O)_2R^{b31}$, $S(O)_2NR^{c31}R^{d31}$, and $BR^{h31}R^{i31}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{32}$;

each $R^{32}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a32}$, $SR^{a32}$, $C(O)R^{b32}$, $C(O)NR^{c32}R^{d32}$, $C(O)OR^{a32}$, $OC(O)R^{b32}$, $OC(O)NR^{c32}R^{d32}$, $NR^{c32}R^{d32}$, $NR^{c32}C(O)R^{b32}$, $NR^{c32}C(O)$ $OR^{a32}$, $NR^{c32}C(O)NR^{c32}R^{d32}$, $NR^{c32}S(O)R^{b32}$, $NR^{c32}S(O)_2R^{b32}$, $NR^{c32}S(O)_2NR^{c32}R^{d32}$, $S(O)R^{b32}$, $S(O)NR^{c32}R^{d32}$, $S(O)_2R^{b32}$, $S(O)_2NR^{c32}R^{d32}$, and $BR^{h32}R^{i32}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{40}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a40}$, $SR^{a40}$, $C(O)R^{b40}$, $C(O)NR^{c40}R^{d40}$, $C(O)OR^{a40}$, $OC(O)R^{b40}$, $OC(O)NR^{c40}R^{d40}$, $NR^{c40}R^{d40}$, $NR^{c40}C(O)R^{b40}$, $NR^{c40}C(O)OR^{a40}$, $NR^{c40}C(O)NR^{c40}R^{d40}$, $NR^{c40}S(O)R^{b40}$, $NR^{c40}S(O)_2R^{b40}$, $NR^{c40}S(O)_2NR^{c40}R^{d40}$, $S(O)R^{b40}$, $S(O)NR^{c40}R^{d40}$, $S(O)_2R^{b40}$, $S(O)_2NR^{c40}R^{d40}$, and $BR^{h40}R^{i40}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{41}$;

each $R^{41}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d41}$, $NR^{c41}S(O)R^{b41}$, $NR^{c41}S(O)_2R^{b41}$, $NR^{c41}S(O)_2NR^{c41}R^{d41}$, $S(O)R^{b41}$, $S(O)NR^{c41}R^{d41}$, $S(O)_2R^{b41}$, $S(O)_2NR^{c41}R^{d41}$, and $BR^{h41}R^{i41}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{42}$;

each $R^{42}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a42}$, $SR^{a42}$, $C(O)R^{b42}$, $C(O)NR^{c42}R^{d42}$, $C(O)OR^{a42}$, $OC(O)R^{b42}$, $OC(O)NR^{c42}R^{d42}$, $NR^{c42}R^{d42}$, $NR^{c42}C(O)R^{b42}$, $NR^{c42}C(O)OR^{a42}$, $NR^{c42}C(O)NR^{c42}R^{d42}$, $NR^{c42}S(O)R^{b42}$, $NR^{c42}S(O)_2R^{b42}$, $NR^{c42}S(O)_2NR^{c42}R^{d42}$, $S(O)R^{b42}$, $S(O)NR^{c42}R^{d42}$, $S(O)_2R^{b42}$, $S(O)_2NR^{c42}R^{d42}$, and $BR^{h42}R^{i42}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{50}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a50}$, $SR^{a50}$, $C(O)R^{b50}$, $C(O)NR^{c50}R^{d50}$, $C(O)OR^{a50}$, $OC(O)R^{b50}$, $OC(O)NR^{c50}R^{d50}$, $NR^{c50}R^{d50}$, $NR^{c50}C(O)R^{b50}$, $NR^{c50}C(O)OR^{a50}$, $NR^{c50}C(O)NR^{c50}R^{d50}$, $NR^{c50}S(O)R^{b50}$, $NR^{c50}S(O)_2R^{b50}$, $NR^{c50}S(O)_2NR^{c50}R^{d50}$, $S(O)R^{b50}$, $S(O)NR^{c50}R^{d50}$, $S(O)_2R^{b50}$, $S(O)_2NR^{c50}R^{d50}$, and $BR^{h50}R^{i50}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{51}$;

each $R^{51}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a51}$, $SR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, and $BR^{h51}R^{i51}$; wherein said $C_{1-6}$ alkyl, $C_{2-6}$ alkenyl, $C_{2-6}$ alkynyl, $C_{3-6}$ cycloalkyl, $C_{6-10}$ aryl, 5-6 membered heteroaryl and 4-7 membered heterocycloalkyl, are each optionally substituted with 1, 2, 3, or 4 substituents independently selected from $R^{52}$;

each $R^{52}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a52}$, $SR^{a52}$, $C(O)R^{b52}$, $C(O)NR^{c52}R^{d52}$, $C(O)OR^{a52}$, $OC(O)R^{b52}$, $OC(O)NR^{c52}R^{d52}$, $NR^{c52}R^{d52}$, $NR^{c52}C(O)R^{b52}$, $NR^{c52}C(O)OR^{a52}$, $NR^{c52}C(O)NR^{c52}R^{d52}$, $NR^{c52}S(O)R^{b52}$, $NR^{c52}S(O)_2R^{b52}$, $NR^{c52}S(O)_2NR^{c52}R^{d52}$, $S(O)R^{b52}$, $S(O)NR^{c52}R^{d52}$, $S(O)_2R^{b52}$, $S(O)_2NR^{c52}R^{d52}$, and $BR^{h52}R^{i52}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{60}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a60}$, $SR^{a60}$, $C(O)R^{b60}$, $C(O)NR^{c60}R^{d60}$, $C(O)OR^{a60}$, $OC(O)R^{b60}$, $OC(O)NR^{c60}R^{d60}$, $NR^{c60}R^{d60}$, $NR^{c60}C(O)R^{b60}$, $NR^{c60}C(O)OR^{a60}$, $NR^{c60}C(O)NR^{c60}R^{d60}$, $NR^{c60}S(O)R^{b60}$, $NR^{c60}S(O)_2R^{b60}$, $NR^{c60}S(O)_2NR^{c60}R^{d60}$, $S(O)R^{b60}$, $S(O)NR^{c60}R^{d60}$, $S(O)_2R^{b60}$, $S(O)_2NR^{c60}R^{d60}$, and $BR^{h60}R^{i60}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{61}$;

each $R^{61}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a61}$, $SR^{a61}$, $C(O)R^{b61}$, $C(O)NR^{c61}R^{d61}$, $C(O)OR^{a61}$, $OC(O)R^{b61}$, $OC(O)NR^{c61}R^{d61}$, $NR^{c61}R^{d61}$, $NR^{c61}C(O)R^{b61}$, $NR^{c61}C(O)OR^{a61}$, $NR^{c61}C(O)NR^{c61}R^{d61}$, $NR^{c61}S(O)R^{b61}$, $NR^{c61}S(O)_2R^{b61}$, $NR^{c61}S(O)_2NR^{c61}R^{d61}$, $S(O)R^{b61}$, $S(O)NR^{c61}R^{d61}$, $S(O)_2R^{b61}$, $S(O)_2NR^{c61}R^{d61}$, and $BR^{h61}R^{i61}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{62}$;

each $R^{62}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a62}$, $SR^{a62}$, $C(O)R^{b62}$, $C(O)NR^{c62}R^{d62}$, $C(O)OR^{a62}$, $OC(O)R^{b62}$, $OC(O)NR^{c62}R^{d62}$, $NR^{c62}R^{d62}$, $NR^{c62}C(O)R^{b62}$, $NR^{c62}C(O)OR^{a62}$, $NR^{c62}C(O)NR^{c62}R^{d62}$, $NR^{c62}S(O)R^{b62}$, $NR^{c62}S(O)_2R^{b62}$, $NR^{c62}S(O)_2NR^{c62}R^{d62}$, $S(O)R^{b62}$, $S(O)NR^{c62}R^{d62}$, $S(O)_2R^{b62}$, $S(O)_2NR^{c62}R^{d62}$, and $BR^{h62}R^{i62}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^a$, $R^b$, $R^c$ and $R^d$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{22}$;

or any $R^c$ and $R^d$ attached to the same N atom, together with the N atom to which they are attached, form a 4-, 5-, 6- or 7-membered heterocycloalkyl group optionally substituted with 1, 2, 3, or 4 substituents independently selected from $R^{22}$;

each $R^e$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^h$ and $R^i$ is independently selected from OH, $C_{1-6}$ alkoxy, and $C_{1-6}$ haloalkoxy; or any $R^h$ and $R^i$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a3}$, $R^{b3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{30}$;

or any $R^{c3}$ and $R^{d3}$ attached to the same N atom, together with the N atom to which they are attached, form a 4-, 5-, 6- or 7-membered heterocycloalkyl group optionally substituted with 1, 2, 3, or 4 substituents independently selected from $R^{30}$;

each $R^{e3}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h3}$ and $R^{i3}$ is independently selected from OH, $C_{1-6}$ alkoxy, and $C_{1-6}$ haloalkoxy; or any $R^{h3}$ and $R^{i3}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a4}$, $R^{b4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c4}$ and $R^{d4}$ attached to the same N atom, together with the N atom to which they are attached, form a 4-, 5-, 6- or 7-membered heterocycloalkyl group optionally substituted with 1, 2, 3, or 4 substituents independently selected from $R^{40}$;

each $R^{e4}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h4}$ and $R^{i4}$ is independently selected from OH, $C_{1-6}$ alkoxy, and $C_{1-6}$ haloalkoxy; or any $R^{h4}$ and $R^{i4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{j4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c4}$ and $R^{j4}$ attached to the same N atom, together with the N atom to which they are attached, form a 4-, 5-, 6- or 7-membered heterocycloalkyl group optionally substituted with 1, 2, 3, or 4 substituents independently selected from $R^{40}$;

each $R^{a5}$, $R^{b5}$, $R^{c5}$, and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{50}$;

or any $R^{c5}$ and $R^{d5}$ attached to the same N atom, together with the N atom to which they are attached, form a 4-, 5-, 6- or 7-membered heterocycloalkyl group optionally substituted with 1, 2 or 3 substituents independently selected from $R^{50}$;

each $R^{e5}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h5}$ and $R^{i5}$ is independently selected from OH, $C_{1-6}$ alkoxy, and $C_{1-6}$ haloalkoxy; or any $R^{h5}$ and $R^{i5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a6}$, $R^{b6}$, $R^{c6}$, and $R^{d6}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^{60}$;

each $R^{e6}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h6}$ and $R^{i6}$ is independently selected from OH, $C_{1-6}$ alkoxy, and $C_{1-6}$ haloalkoxy; or any $R^{h6}$ and $R^{i6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a10}$, $R^{b10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

or any $R^{c10}$ and $R^{d10}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{e10}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h10}$ and $R^{i10}$ is independently selected from OH, $C_{1-6}$ alkoxy, and $C_{1-6}$ haloalkoxy; or any $R^{h10}$ and $R^{i10}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a11}$, $R^{b11}$, $R^{c11}$ and $R^{d11}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

or any $R^{c11}$ and $R^{d11}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{h11}$ and $R^{i11}$ is independently selected from OH, $C_{1-6}$ alkoxy, and $C_{1-6}$ haloalkoxy; or any $R^{h11}$ and $R^{i11}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a12}$, $R^{b12}$, $R^{c12}$ and $R^{d12}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{h12}$ and $R^{i12}$ is independently selected from OH, $C_{1-6}$ alkoxy, and $C_{1-6}$ haloalkoxy; or any $R^{h12}$ and $R^{i12}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a20}$, $R^{b20}$, $R^{c20}$ and $R^{d20}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{21}$;

or any $R^{c20}$ and $R^{d20}$ attached to the same N atom, together with the N atom to which they are attached, form a 4-, 5-, 6- or 7-membered heterocycloalkyl group optionally substituted with 1, 2, 3, or 4 substituents independently selected from $R^{21}$;

each $R^{e20}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h20}$ and $R^{i20}$ is independently selected from OH, $C_{1-6}$ alkoxy, and $C_{1-6}$ haloalkoxy; or any $R^{h20}$ and $R^{i20}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a21}$, $R^{b21}$, $R^{c21}$ and $R^{d21}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

or any $R^{c21}$ and $R^{d21}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{h21}$ and $R^{i21}$ is independently selected from OH, $C_{1-6}$ alkoxy, and $C_{1-6}$ haloalkoxy; or any $R^{h21}$ and $R^{i21}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a22}$, $R^{b22}$, $R^{c22}$ and $R^{d22}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{23}$;

or any $R^{c22}$ and $R^{d22}$ attached to the same N atom, together with the N atom to which they are attached, form a 4-, 5-, 6- or 7-membered heterocycloalkyl group optionally substituted with 1, 2, 3, or 4 substituents independently selected from $R^{23}$;

each $R^{h22}$ and $R^{i22}$ is independently selected from OH, $C_{1-6}$ alkoxy, and $C_{1-6}$ haloalkoxy; or any $R^{h22}$ and $R^{i22}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a23}$, $R^{b23}$, $R^{c23}$ and $R^{d23}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{24}$;

or any $R^{c23}$ and $R^{d23}$ attached to the same N atom, together with the N atom to which they are attached, form a 4-, 5-, 6- or 7-membered heterocycloalkyl group optionally substituted with 1, 2 or 3 substituents independently selected from $R^{24}$;

each $R^{h23}$ and $R^{i23}$ is independently selected from OH, $C_{1-6}$ alkoxy, and $C_{1-6}$ haloalkoxy; or any $R^{h23}$ and $R^{i23}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a24}$, $R^{b24}$, $R^{c24}$ and $R^{d24}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{h24}$ and $R^{i24}$ is independently selected from OH, $C_{1-6}$ alkoxy, and $C_{1-6}$ haloalkoxy; or any $R^{h24}$ and $R^{i24}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a30}$, $R^{b30}$, $R^{c30}$ and $R^{d30}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{31}$;

or any $R^{c30}$ and $R^{d30}$ attached to the same N atom, together with the N atom to which they are attached, form a 4-, 5-, 6- or 7-membered heterocycloalkyl group optionally substituted with 1, 2, 3, or 4 substituents independently selected from $R^{31}$;

each $R^{h30}$ and $R^{i30}$ is independently selected from OH, $C_{1-6}$ alkoxy, and $C_{1-6}$ haloalkoxy; or any $R^{h30}$ and $R^{i30}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a31}$, $R^{b31}$, $R^{c31}$ and $R^{d31}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{32}$;

or any $R^{c31}$ and $R^{d31}$ attached to the same N atom, together with the N atom to which they are attached, form a 4-, 5-, 6- or 7-membered heterocycloalkyl group optionally substituted with 1, 2 or 3 substituents independently selected from $R^{32}$;

each $R^{h31}$ and $R^{i31}$ is independently selected from OH, $C_{1-6}$ alkoxy, and $C_{1-6}$ haloalkoxy; or any $R^{h31}$ and $R^{i31}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a32}$, $R^{b32}$, $R^{c32}$ and $R^{d32}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c32}$ and $R^{d32}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{h32}$ and $R^{i32}$ is independently selected from OH, $C_{1-6}$ alkoxy, and $C_{1-6}$ haloalkoxy; or any $R^{h32}$ and $R^{i32}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a40}$, $R^{b40}$, $R^{c40}$ and $R^{d40}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{41}$;

or any $R^{c40}$ and $R^{d40}$ attached to the same N atom, together with the N atom to which they are attached, form a 4-, 5-, 6- or 7-membered heterocycloalkyl group optionally substituted with 1, 2, 3, or 4 substituents independently selected from $R^{41}$;

each $R^{h40}$ and $R^{i40}$ is independently selected from OH, $C_{1-6}$ alkoxy, and $C_{1-6}$ haloalkoxy; or any $R^{h40}$ and $R^{i40}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a41}$, $R^{b41}$, $R^{c41}$ and $R^{d41}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{42}$;

or any $R^{c41}$ and $R^{d41}$ attached to the same N atom, together with the N atom to which they are attached, form a 4-, 5-, 6- or 7-membered heterocycloalkyl group optionally substituted with 1, 2 or 3 substituents independently selected from $R^{42}$;

each $R^{h41}$ and $R^{i41}$ is independently selected from OH, $C_{1-6}$ alkoxy, and $C_{1-6}$ haloalkoxy; or any $R^{h41}$ and $R^{i41}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a42}$, $R^{b42}$, $R^{c42}$ and $R^{d42}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c42}$ and $R^{d42}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{h42}$ and $R^{i42}$ is independently selected from OH, $C_{1-6}$ alkoxy, and $C_{1-6}$ haloalkoxy; or any $R^{h42}$ and $R^{i42}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a50}$, $R^{b50}$, $R^{c50}$ and $R^{d50}$, is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{51}$;

or any $R^{c50}$ and $R^{d50}$ attached to the same N atom, together with the N atom to which they are attached, form a 4-, 5-, 6- or 7-membered heterocycloalkyl group optionally substituted with 1, 2 or 3 substituents independently selected from $R^{51}$;

each $R^{h50}$ and $R^{i50}$ is independently selected from OH, $C_{1-6}$ alkoxy, and $C_{1-6}$ haloalkoxy; or any $R^{h50}$ and $R^{i50}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a51}$, $R^{b51}$, $R^{c51}$ and $R^{d51}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{52}$;

or any $R^{c51}$ and $R^{d51}$ attached to the same N atom, together with the N atom to which they are attached, form a 4-, 5-, 6- or 7-membered heterocycloalkyl group optionally substituted with 1, 2, 3, or 4 substituents independently selected from $R^{52}$;

each $R^{h51}$ and $R^{i51}$ is independently selected from OH, $C_{1-6}$ alkoxy, and $C_{1-6}$ haloalkoxy; or any $R^{h51}$ and $R^{i51}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a52}$, $R^{b52}$, $R^{c52}$ and $R^{d52}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c52}$ and $R^{d52}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{h52}$ and $R^{i52}$ is independently selected from OH, $C_{1-6}$ alkoxy, and $C_{1-6}$ haloalkoxy; or any $R^{h52}$ and $R^{i52}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a60}$, $R^{b60}$, $R^{c60}$ and $R^{d60}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{61}$;

or any $R^{c60}$ and $R^{d60}$ attached to the same N atom, together with the N atom to which they are attached, form a 4-, 5-, 6- or 7-membered heterocycloalkyl group optionally substituted with 1, 2, 3, or 4 substituents independently selected from $R^{61}$;

each $R^{h60}$ and $R^{i60}$ is independently selected from OH, $C_{1-6}$ alkoxy, and $C_{1-6}$ haloalkoxy; or any $R^{h60}$ and $R^{i60}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a61}$, $R^{b61}$, $R^{c61}$ and $R^{d61}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{62}$;

or any $R^{c61}$ and $R^{d61}$ attached to the same N atom, together with the N atom to which they are attached, form a 4-, 5-, 6- or 7-membered heterocycloalkyl group optionally substituted with 1, 2 or 3 substituents independently selected from $R^{62}$;

each $R^{h61}$ and $R^{i61}$ is independently selected from OH, $C_{1-6}$ alkoxy, and $C_{1-6}$ haloalkoxy; or any $R^{h61}$ and $R^{i61}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a62}$, $R^{b62}$, $R^{c62}$ and $R^{d62}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c62}$ and $R^{d62}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{h62}$ and $R^{i62}$ is independently selected from OH, $C_{1-6}$ alkoxy, and $C_{1-6}$ haloalkoxy; or any $R^{h62}$ and $R^{i62}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^g$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In an embodiment of a compound of Formula I, or a pharmaceutically acceptable salt thereof, === represents a single bond or a double bond;

X is N or $CR^5$;

Y is N or $CR^6$;

each R is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NOR^a)R^b$, $C(=NR^e)NR^cR^d$, $NR^cC(=NR^e)NR^cR^d$, $NR^cC(=NR^e)R^b$, $NR^cS(O)R^b$, $NR^cS(O)_2R^b$, $NR^cS(O)_2NR^cR^d$, $S(O)R^b$, $S(O)NR^cR^d$, $S(O)_2R^b$, $S(O)_2NR^cR^d$, and $BR^hR^i$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

n is 0, 1, 2, 3, or 4;

$Cy^1$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

$R^{3A}$ and $R^{3B}$ are each independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NOR^{a3})R^{b3}$, $C(=NR^{e3})NR^{c3}R^{d3}$, $NR^{c3}C(=NR^{e3})NR^{c3}R^{d3}$, $NR^{c3}C(=NR^{e3})R^{b3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$, and $BR^{h3}R^{i3}$; or $R^{3A}$ and $R^{3B}$ can be taken together with the carbon atom to which they are attached to form a C=O;

$R^4$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NOR^{a4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, and $BR^{h4}R^{i4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{40}$;

$R^5$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NOR^{a5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, and $BR^{h5}R^{i5}$;

$R^6$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOR^{a6})R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, and $BR^{h6}R^{i6}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{60}$;

$Cy^2$ is selected from $C_{3-10}$cycloalkyl, 4-14 membered heterocycloalkyl, $C_{6-10}$ aryl and 5-10 membered heteroaryl; wherein the 4-14 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-14 membered heterocycloalkyl is optionally substituted by oxo to form a carbonyl group; and wherein the $C_{3-10}$ cycloalkyl, 4-14 membered heterocycloalkyl, $C_{6-10}$ aryl and 5-10 membered heteroaryl are each optionally substituted with 1, 2, 3 or 4 substituents independently selected from $R^{20}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a10}$, $SR^{a10}$, $C(O)R^{b10}$, C(O)NR$^{c10}$R$^{d10}$, C(O)OR$^{a10}$, OC(O)R$^{b10}$, OC(O)NR$^{c10}$R$^{d10}$, NR$^{c10}$R$^{d10}$, NR$^{c10}$C(O)R$^{b10}$, NR$^{c10}$C(O)OR$^{a10}$, NR$^{c10}$C(O)NR$^{c10}$R$^{d10}$, C(=NR$^{e10}$)R$^{b10}$, C(=NOR$^{a10}$)R$^{b10}$, C(=NR$^{e10}$)NR$^{c10}$R$^{d10}$, NR$^{c10}$C(=NR$^{e10}$)NR$^{c10}$R$^{d10}$, NR$^{c10}$S(O)R$^{b10}$, NR$^{c10}$S(O)$_2$R$^{b10}$, NR$^{c10}$S(O)$_2$NR$^{c10}$R$^{d10}$, S(O)R$^{b10}$, S(O)NR$^{c10}$R$^{d10}$, S(O)$_2$R$^{b10}$, S(O)$_2$NR$^{c10}$R$^{d10}$, and BR$^{h10}$R$^{i10}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from R$^{11}$;

each R$^{11}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$ alkylene, halo, D, CN, OR$^{a11}$, SR$^{a11}$, C(O)R$^{b11}$, C(O)NR$^{c11}$R$^{d11}$, C(O)OR$^{a11}$, OC(O)R$^{b11}$, OC(O)NR$^{c11}$R$^{d11}$, NR$^{c11}$R$^{d11}$, NR$^{c11}$C(O)R$^{b11}$, NR$^{c11}$C(O)OR$^{a11}$, NR$^{c11}$C(O)NR$^{c11}$R$^{d11}$, NR$^{c11}$S(O)R$^{b11}$, NR$^{c11}$S(O)$_2$R$^{b11}$, NR$^{c11}$S(O)$_2$NR$^{c11}$R$^{d11}$, S(O)R$^{b11}$, S(O)NR$^{c11}$R$^{d11}$, S(O)$_2$R$^{b11}$, S(O)$_2$NR$^{c11}$R$^{d11}$, and BR$^{h11}$R$^{i11}$;

each R$^{20}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$ alkylene, halo, D, CN, NO$_2$, OR$^{a20}$, SR$^{a20}$, C(O)R$^{b20}$, C(O)NR$^{c20}$R$^{d20}$, C(O)OR$^{a20}$, OC(O)R$^{b20}$, OC(O)NR$^{c20}$R$^{d20}$, NR$^{c20}$R$^{d20}$, NR$^{c20}$C(O)R$^{b20}$, NR$^{c20}$C(O)OR$^{a20}$, NR$^{c20}$C(O)NR$^{c20}$R$^{d20}$, C(=NR$^{e20}$)R$^{b20}$, C(=NOR$^{a20}$)R$^{b20}$, C(=NR$^{e20}$)NR$^{c20}$R$^{d20}$, NR$^{c20}$C(=NR$^{e20}$)NR$^{c20}$R$^{d20}$, NR$^{c20}$S(O)R$^{b20}$, NR$^{c20}$S(O)$_2$R$^{b20}$, NR$^{c20}$S(O)$_2$NR$^{c20}$R$^{d20}$, S(O)R$^{b20}$, S(O)NR$^{c20}$R$^{d20}$, S(O)$_2$R$^{b20}$, S(O)$_2$NR$^{c20}$R$^{d20}$, and BR$^{h20}$R$^{i20}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from R$^{21}$;

each R$^{21}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$ alkylene, halo, D, CN, OR$^{a21}$, SR$^{a21}$, C(O) R$^{b21}$, C(O)NR$^{c21}$R$^{d21}$, C(O)OR$^{a21}$, OC(O)R$^{b21}$, OC(O)NR$^{c21}$R$^{d21}$, NR$^{c21}$R$^{d21}$, NR$^{c21}$C(O)R$^{b21}$, NR$^{c21}$C(O)OR$^{a21}$, NR$^{c21}$C(O)NR$^{c21}$R$^{d21}$, NR$^{c21}$S(O)R$^{b21}$, NR$^{c21}$S(O)$_2$R$^{b21}$, NR$^{c21}$S(O)$_2$NR$^{c21}$R$^{d21}$, S(O)R$^{b21}$, S(O)NR$^{c21}$R$^{d21}$, S(O)$_2$R$^{b21}$, S(O)$_2$NR$^{c21}$R$^{d21}$, and BR$^{b21}$R$^{i21}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from R$^g$;

each R$^{22}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$ alkylene, halo, D, CN, NO$_2$, OR$^{a22}$, SR$^{a22}$, C(O)R$^{b22}$, C(O)NR$^{c22}$R$^{d22}$, C(O)OR$^{a22}$, OC(O)R$^{b22}$, OC(O)NR$^{c22}$R$^{d22}$, NR$^{c22}$R$^{d22}$, NR$^{c22}$C(O)R$^{b22}$, NR$^{c22}$C(O)OR$^{a22}$, NR$^{c22}$C(O)NR$^{c22}$R$^{d22}$, NR$^{c22}$S(O)R$^{b22}$, NR$^{c22}$S(O)$_2$R$^{b22}$, NR$^{c22}$S(O)$_2$NR$^{c22}$R$^{d22}$, S(O)R$^{b22}$, S(O)NR$^{c22}$R$^{d22}$, S(O)$_2$R$^{b22}$, S(O)$_2$NR$^{c22}$R$^{d22}$, and BR$^{h22}$R$^{i22}$;

each R$^{40}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$ alkylene, halo, D, CN, NO$_2$, OR$^{a40}$, SR$^{a40}$, C(O)R$^{b40}$, C(O)NR$^{c40}$R$^{d40}$, C(O)OR$^{a40}$, OC(O)R$^{b40}$, OC(O)NR$^{c40}$R$^{d40}$, NR$^{c40}$R$^{d40}$, NR$^{c40}$C(O)R$^{b40}$, NR$^{c40}$C(O)OR$^{a40}$, NR$^{c40}$C(O)NR$^{c40}$R$^{d40}$, NR$^{c40}$S(O)R$^{b40}$, NR$^{c40}$S(O)$_2$R$^{b40}$, NR$^{c40}$S(O)$_2$NR$^{c40}$R$^{d40}$, S(O)R$^{b40}$, S(O)NR$^{c40}$R$^{d40}$, S(O)$_2$R$^{b40}$, S(O)$_2$NR$^{c40}$R$^{d40}$, and BR$^{h40}$R$^{i40}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from R$^{41}$;

each R$^{41}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$ alkylene, halo, D, CN, OR$^{a41}$, SR$^{a41}$, C(O)R$^{b41}$, C(O)NR$^{c41}$R$^{d41}$, C(O)OR$^{a41}$, OC(O)R$^{b41}$, OC(O)NR$^{c41}$R$^{d41}$, NR$^{c41}$R$^{d41}$, NR$^{c41}$C(O)R$^{b41}$, NR$^{c41}$C(O)OR$^{a41}$, NR$^{c41}$C(O)NR$^{c41}$R$^{d41}$, NR$^{c41}$S(O)R$^{b41}$, NR$^{c41}$S(O)$_2$R$^{b41}$, NR$^{c41}$S(O)$_2$NR$^{c41}$R$^{d41}$, S(O)R$^{b41}$, S(O)NR$^{c41}$R$^{d41}$, S(O)$_2$R$^{b41}$, S(O)$_2$NR$^{c41}$R$^{d41}$, and BR$^{h41}$R$^{i41}$;

each R$^{60}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$ alkylene, halo, D, CN, NO$_2$, OR$^{a60}$, SR$^{a60}$, C(O)R$^{b60}$, C(O)NR$^{c60}$R$^{d60}$, C(O)OR$^{a60}$, OC(O)R$^{b60}$, OC(O)NR$^{c60}$R$^{d60}$, NR$^{c60}$R$^{d60}$, NR$^{c60}$C(O)R$^{b60}$, NR$^{c60}$C(O)OR$^{a60}$, NR$^{c60}$C(O)NR$^{c60}$R$^{d60}$, NR$^{c60}$S(O)R$^{b60}$, NR$^{c60}$S(O)$_2$R$^{b60}$, NR$^{c60}$S(O)$_2$NR$^{c60}$R$^{d60}$, S(O)R$^{b60}$, S(O)NR$^{c60}$R$^{d60}$, S(O)$_2$R$^{b60}$, S(O)$_2$NR$^{c60}$R$^{d60}$, and BR$^{h60}$R$^{i60}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from $R^{61}$;

each $R^{61}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a61}$, $SR^{a61}$, $C(O)R^{b61}$, $C(O)NR^{c61}R^{d61}$, $C(O)OR^{a61}$, $OC(O)R^{b61}$, $OC(O)NR^{c61}R^{d61}$, $NR^{c61}R^{d61}$, $NR^{c61}C(O)R^{b61}$, $NR^{c61}C(O)OR^{a61}$, $NR^{c61}C(O)NR^{c61}R^{d61}$, $NR^{c61}S(O)R^{b61}$, $NR^{c61}S(O)_2R^{b61}$, $NR^{c61}S(O)_2NR^{c61}R^{d61}$, $S(O)R^{b61}$, $S(O)NR^{c61}R^{d61}$, $S(O)_2R^{b61}$, $S(O)_2NR^{c61}R^{d61}$, and $BR^{h61}R^{i61}$;

each $R^a$, $R^b$, $R^c$ and $R^d$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{22}$;

or any $R^c$ and $R^d$ attached to the same N atom, together with the N atom to which they are attached, form a 4-, 5-, 6- or 7-membered heterocycloalkyl group optionally substituted with 1, 2, 3, or 4 substituents independently selected from $R^{22}$;

each $R^e$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^h$ and $R^i$ is independently selected from OH, $C_{1-6}$ alkoxy, and $C_{1-6}$ haloalkoxy; or any $R^h$ and $R^i$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a3}$, $R^{b3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c3}$ and $R^{d3}$ attached to the same N atom, together with the N atom to which they are attached, form a 4-, 5-, 6- or 7-membered heterocycloalkyl group;

each $R^{e3}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h3}$ and $R^{i3}$ is independently selected from OH, $C_{1-6}$ alkoxy, and $C_{1-6}$ haloalkoxy; or any $R^{h3}$ and $R^{i3}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a4}$, $R^{b4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c4}$ and $R^{d4}$ attached to the same N atom, together with the N atom to which they are attached, form a 4-, 5-, 6- or 7-membered heterocycloalkyl group optionally substituted with 1, 2, 3, or 4 substituents independently selected from $R^{40}$;

each $R^{e4}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h4}$ and $R^{i4}$ is independently selected from OH, $C_{1-6}$ alkoxy, and $C_{1-6}$ haloalkoxy; or any $R^{h4}$ and $R^{i4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{j4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c4}$ and $R^{j4}$ attached to the same N atom, together with the N atom to which they are attached, form a 4-, 5-, 6- or 7-membered heterocycloalkyl group optionally substituted with 1, 2, 3, or 4 substituents independently selected from $R^{40}$;

each $R^{a5}$, $R^{b5}$, $R^{c5}$, and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c5}$ and $R^{d5}$ attached to the same N atom, together with the N atom to which they are attached, form a 4-, 5-, 6- or 7-membered heterocycloalkyl group;

each $R^{e5}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h5}$ and $R^{i5}$ is independently selected from OH, $C_{1-6}$ alkoxy, and $C_{1-6}$ haloalkoxy; or any $R^{h5}$ and $R^{i5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a6}$, $R^{b6}$, $R^{c6}$, and $R^{d6}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^{60}$;

each $R^{e6}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h6}$ and $R^{i6}$ is independently selected from OH, $C_{1-6}$ alkoxy, and $C_{1-6}$ haloalkoxy; or any $R^{h6}$ and $R^{i6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a10}$, $R^{b10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

or any $R^{c10}$ and $R^{d10}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{e10}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h10}$ and $R^{i10}$ is independently selected from OH, $C_{1-6}$ alkoxy, and $C_{1-6}$ haloalkoxy; or any $R^{h10}$ and $R^{i10}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a11}$, $R^{b11}$, $R^{c11}$ and $R^{d11}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c11}$ and $R^{d11}$ attached to the same N atom, together with the N atom to which they are attached, form a 4-, 5-, 6- or 7-membered heterocycloalkyl group;

each $R^{h11}$ and $R^{i11}$ is independently selected from OH, $C_{1-6}$ alkoxy, and $C_{1-6}$ haloalkoxy; or any $R^{h11}$ and $R^{i11}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a20}$, $R^{b20}$, $R^{c20}$ and $R^{d20}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{21}$;

or any $R^{c20}$ and $R^{d20}$ attached to the same N atom, together with the N atom to which they are attached, form a 4-, 5-, 6- or 7-membered heterocycloalkyl group optionally substituted with 1, 2, 3, or 4 substituents independently selected from $R^{21}$;

each $R^{e20}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h20}$ and $R^{i20}$ is independently selected from OH, $C_{1-6}$ alkoxy, and $C_{1-6}$ haloalkoxy; or any $R^{h20}$ and $R^{i20}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a21}$, $R^{b21}$, $R^{c21}$ and $R^{d21}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

or any $R^{c21}$ and $R^{d21}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{h21}$ and $R^{i21}$ is independently selected from OH, $C_{1-6}$ alkoxy, and $C_{1-6}$ haloalkoxy; or any $R^{h21}$ and $R^{i21}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a22}$, $R^{b22}$, $R^{c22}$ and $R^{d22}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c22}$ and $R^{d22}$ attached to the same N atom, together with the N atom to which they are attached, form a 4-, 5-, 6- or 7-membered heterocycloalkyl group;

each $R^{h22}$ and $R^{i22}$ is independently selected from OH, $C_{1-6}$ alkoxy, and $C_{1-6}$ haloalkoxy; or any $R^{h22}$ and $R^{i22}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a40}$, $R^{b40}$, $R^{c40}$ and $R^{d40}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{41}$;

or any $R^{c40}$ and $R^{d40}$ attached to the same N atom, together with the N atom to which they are attached, form a 4-, 5-, 6- or 7-membered heterocycloalkyl group optionally substituted with 1, 2, 3, or 4 substituents independently selected from $R^{41}$;

each $R^{h40}$ and $R^{i40}$ is independently selected from OH, $C_{1-6}$ alkoxy, and $C_{1-6}$ haloalkoxy; or any $R^{h40}$ and $R^{i40}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a41}$, $R^{b41}$, $R^{c41}$ and $R^{d41}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c41}$ and $R^{d41}$ attached to the same N atom, together with the N atom to which they are attached, form a 4-, 5-, 6- or 7-membered heterocycloalkyl group;

each $R^{h41}$ and $R^{i41}$ is independently selected from OH, $C_{1-6}$ alkoxy, and $C_{1-6}$ haloalkoxy; or any $R^{h41}$ and $R^{i41}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a60}$, $R^{b60}$, $R^{c60}$ and $R^{d60}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{61}$;

or any $R^{c60}$ and $R^{d60}$ attached to the same N atom, together with the N atom to which they are attached, form a 4-, 5-, 6- or 7-membered heterocycloalkyl group optionally substituted with 1, 2, 3, or 4 substituents independently selected from $R^{61}$;

each $R^{h60}$ and $R^{i60}$ is independently selected from OH, $C_{1-6}$ alkoxy, and $C_{1-6}$ haloalkoxy; or any $R^{h60}$ and $R^{i60}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a61}$, $R^{b61}$, $R^{c61}$ and $R^{d61}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c61}$ and $R^{d61}$ attached to the same N atom, together with the N atom to which they are attached, form a 4-, 5-, 6- or 7-membered heterocycloalkyl group;

each $R^{h61}$ and $R^{i61}$ is independently selected from OH, $C_{1-6}$ alkoxy, and $C_{1-6}$ haloalkoxy; or any $R^{h61}$ and $R^{i61}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^g$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In yet another embodiment of a compound of Formula I, or a pharmaceutically acceptable salt thereof, ═══ represents a single bond or a double bond;

X is N or $CR^5$;

Y is N or $CR^6$;

each R is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $NR^cS(O)_2R^b$, $NR^cS(O)_2NR^cR^d$, $S(O)_2R^b$, and $S(O)_2NR^cR^d$;

n is 0, 1, 2, 3, or 4;

$Cy^1$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

$R^{3A}$ and $R^{3B}$ are each independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$;

or $R^{3A}$ and $R^{3B}$ can be taken together with the carbon atom to which they are attached to form a C═O;

$R^4$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{40}$;

$R^5$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)_2R^{b5}$, $NR^{c5}S(O)_2NR^{c5}R^{d5}$, $S(O)^2R^{b5}$, and $S(O)_2NR^{c5}R^{d5}$;

$R^6$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)_2R^{b6}$, $NR^{c6}S(O)_2NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{60}$;

$Cy^2$ is selected from $C_{3-10}$ cycloalkyl, 4-14 membered heterocycloalkyl, $C_{6-10}$ aryl and 5-10 membered heteroaryl; wherein the 4-14 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-14 membered heterocycloalkyl is optionally substituted by oxo to form a carbonyl group; and wherein the $C_{3-10}$ cycloalkyl, 4-14 membered heterocycloalkyl, $C_{6-10}$ aryl and 5-10 membered heteroaryl are each optionally substituted with 1, 2, 3 or 4 substituents independently selected from $R^{20}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a10}$, $SR^{a10}$, $C(O)R^{b10}$, $C(O)NR^{c10}R^{d10}$, $C(O)OR^{a10}$, $OC(O)R^{b10}$, $OC(O)NR^{c10}R^{d10}$, $NR^{c10}R^{d10}$, $NR^{c10}C(O)R^{b10}$, $NR^{c10}C(O)OR^{a10}$, $NR^{c10}C(O)NR^{c10}R^{d10}$, $NR^{c10}S(O)_2R^{b10}$, $NR^{c10}S(O)_2NR^{c10}R^{d10}$, $S(O)_2R^{b10}$, and $S(O)_2NR^{c10}R^{d10}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a20}$, $SR^{a20}$, $C(O)R^{b20}$, $C(O)NR^{c20}R^{d20}$, $C(O)OR^{a20}$, $OC(O)R^{b20}$, $OC(O)NR^{c20}R^{d20}$, $NR^{c20}R^{d20}$, $NR^{c20}C(O)R^{b20}$, $NR^{c20}C(O)OR^{a20}$, $NR^{c20}C(O)NR^{c20}R^{d20}$, $NR^{c20}S(O)_2R^{b20}$, $NR^{c20}S(O)_2NR^{c20}R^{d20}$, $S(O)_2R^{b20}$, and $S(O)_2NR^{c20}R^{d20}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)_2R^{b21}$, $NR^{c21}S(O)_2NR^{c21}R^{d21}$, $S(O)_2R^{b21}$, and $S(O)_2NR^{c21}R^{d21}$;

each $R^{40}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a40}$, $SR^{a40}$, $C(O)R^{b40}$, $C(O)NR^{c40}R^{d40}$, $C(O)OR^{a40}$, $OC(O)R^{b40}$, $OC(O)NR^{c40}R^{d40}$, $NR^{c40}R^{d40}$, $NR^{c40}C(O)R^{b40}$, $NR^{c40}C(O)OR^{a40}$, $NR^{c40}C(O)NR^{c40}R^{d40}$, $NR^{c40}S(O)_2R^{b40}$, $NR^{c40}S(O)_2NR^{c40}R^{d40}$, $S(O)_2R^{b40}$, and $S(O)_2NR^{c40}R^{d40}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{41}$;

each $R^{41}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d41}$, $NR^{c41}S(O)_2R^{b41}$, $NR^{c41}S(O)_2NR^{c41}R^{d41}$, $S(O)_2R^{b41}$, and $S(O)_2NR^{c41}R^{d41}$;

each $R^{60}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a60}$, $SR^{a60}$, $C(O)R^{b60}$, $C(O)NR^{c60}R^{d60}$, $C(O)OR^{a60}$, $OC(O)R^{b60}$, $OC(O)NR^{c60}R^{d60}$, $NR^{c60}R^{d60}$, $NR^{c60}C(O)R^{b60}$, $NR^{c60}C(O)$ $OR^{a60}$, $NR^{c60}C(O)NR^{c60}R^{d60}$, $NR^{c60}S(O)_2R^{b60}$, $NR^{c60}S(O)_2NR^{c60}R^{d60}$, $S(O)_2R^{b60}$, and $S(O)_2NR^{c60}R^{d60}$;

each $R^a$, $R^b$, $R^c$ and $R^d$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^c$ and $R^d$ attached to the same N atom, together with the N atom to which they are attached, form a 4-, 5-, 6- or 7-membered heterocycloalkyl group;

each $R^{a3}$, $R^{b3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c3}$ and $R^{d3}$ attached to the same N atom, together with the N atom to which they are attached, form a 4-, 5-, 6- or 7-membered heterocycloalkyl group;

each $R^{a4}$, $R^{b4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c4}$ and $R^{d4}$ attached to the same N atom, together with the N atom to which they are attached, form a 4-, 5-, 6- or 7-membered heterocycloalkyl group optionally substituted with 1, 2, 3, or 4 substituents independently selected from $R^{40}$;

each $R^{j4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c4}$ and $R^{j4}$ attached to the same N atom, together with the N atom to which they are attached, form a 4-, 5-, 6- or 7-membered heterocycloalkyl group optionally substituted with 1, 2, 3, or 4 substituents independently selected from $R^{40}$;

each $R^{a5}$, $R^{b5}$, $R^{c5}$, and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c5}$ and $R^{d5}$ attached to the same N atom, together with the N atom to which they are attached, form a 4-, 5-, 6- or 7-membered heterocycloalkyl group;

each $R^{a6}$, $R^{b6}$, $R^{c6}$, and $R^{d6}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^{60}$;

each $R^{a10}$, $R^{b10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c10}$ and $R^{d10}$ attached to the same N atom, together with the N atom to which they are attached, form a 4-, 5-, 6- or 7-membered heterocycloalkyl group;

each $R^{a20}$, $R^{b20}$, $R^{c20}$ and $R^{d20}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{21}$;

or any $R^{c20}$ and $R^{d20}$ attached to the same N atom, together with the N atom to which they are attached, form a 4-, 5-, 6- or 7-membered heterocycloalkyl group optionally substituted with 1, 2, 3, or 4 substituents independently selected from $R^{21}$;

each $R^{a21}$, $R^{b21}$, $R^{c21}$ and $R^{d21}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c21}$ and $R^{d21}$ attached to the same N atom, together with the N atom to which they are attached, form a 4-, 5-, 6- or 7-membered heterocycloalkyl group;

each $R^{a40}$, $R^{b40}$, $R^{c40}$ and $R^{d40}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{41}$;

or any $R^{c40}$ and $R^{d40}$ attached to the same N atom, together with the N atom to which they are attached, form a 4-, 5-, 6- or 7-membered heterocycloalkyl group optionally substituted with 1, 2, 3, or 4 substituents independently selected from $R^{41}$;

each $R^{a41}$, $R^{b41}$, $R^{c41}$ and $R^{d41}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c41}$ and $R^{d41}$ attached to the same N atom, together with the N atom to which they are attached, form a 4-, 5-, 6- or 7-membered heterocycloalkyl group; and each $R^{a60}$, $R^{b60}$, $R^{c60}$ and $R^{d60}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c60}$ and $R^{d60}$ attached to the same N atom, together with the N atom to which they are attached, form a 4-, 5-, 6- or 7-membered heterocycloalkyl group.

In an embodiment of a compound of Formula I, or a pharmaceutically acceptable salt thereof, === represents a single bond or a double bond;

X is N;

Y is N or $CR^6$;

each R is independently selected from $C_{1-6}$ alkyl, $C_{1-6}$ haloalkyl, halo, D, CN, $OR^a$, and $NR^cR^d$;

n is 0, 1, or 2;

Cy$^1$ is selected from C$_{6-10}$ aryl and 5-10 membered heteroaryl; wherein the 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the C$_{6-10}$ aryl and 5-10 membered heteroaryl are each optionally substituted with 1, 2, 3 or 4 substituents independently selected from R$^{10}$;

R$^{3A}$ and R$^{3B}$ are each independently selected from H, C$_{1-6}$ alkyl, C$_{1-6}$ haloalkyl, halo, D, CN, OR$^{a3}$, and NR$^{c3}$R$^{d3}$;

or R$^{3A}$ and R$^{3B}$ can be taken together with the carbon atom to which they are attached to form a C=O;

R$^4$ is selected from H, C$_{1-6}$ alkyl, C$_{1-6}$ haloalkyl, C$_{3-10}$ cycloalkyl, 4-10 membered heterocycloalkyl, C$_{6-10}$ aryl, 5-10 membered heteroaryl, halo, D, CN, OR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, and NR$^{c4}$C(O)R$^{b4}$; wherein said C$_{1-6}$ alkyl, C$_{3-10}$ cycloalkyl, 4-10 membered heterocycloalkyl, C$_{6-10}$ aryl, and 5-10 membered heteroaryl, are each optionally substituted with 1, 2, 3, or 4 substituents independently selected from R$^{40}$;

R$^6$ is selected from H, C$_{1-6}$ alkyl, C$_{1-6}$ haloalkyl, C$_{3-10}$ cycloalkyl, 4-10 membered heterocycloalkyl, C$_{6-10}$ aryl, 5-10 membered heteroaryl, halo, D, CN, OR$^{a6}$, and NR$^{c6}$R$^{d6}$; wherein said C$_{1-6}$ alkyl, C$_{3-10}$ cycloalkyl, 4-10 membered heterocycloalkyl, C$_{6-10}$ aryl, and 5-10 membered heteroaryl, are each optionally substituted with 1, 2, 3, or 4 substituents independently selected from R$^{60}$;

Cy$^2$ is selected from C$_{3-10}$ cycloalkyl, and 4-14 membered heterocycloalkyl; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group; and wherein the C$_{3-10}$ cycloalkyl, and 4-14 membered heterocycloalkyl, are each optionally substituted with 1, 2, 3 or 4 substituents independently selected from R$^{20}$;

each R$^{10}$ is independently selected from C$_{1-6}$ alkyl, C$_{1-6}$ haloalkyl, halo, D, CN, OR$^{a10}$, and NR$^{c10}$R$^{d10}$;

each R$^{20}$ is independently selected from C$_{1-6}$ alkyl, C$_{2-6}$ alkenyl, C$_{2-6}$ alkynyl, C$_{1-6}$ haloalkyl, halo, D, CN, OR$^{a20}$, C(O)R$^{b20}$, C(O)NR$^{c20}$R$^{d20}$, and NR$^{c20}$R$^{d20}$; wherein said C$_{1-6}$ alkyl, is optionally substituted with 1, 2, 3, or 4 substituents independently selected from R$^{21}$;

each R$^{21}$ is independently selected from C$_{1-6}$ alkyl, C$_{1-6}$ haloalkyl, halo, D, CN, OR$^{a21}$, and NR$^{c21}$R$^{d21}$;

each R$^{40}$ is independently selected from C$_{1-6}$ alkyl, C$_{1-6}$ haloalkyl, C$_{3-10}$ cycloalkyl, 4-10 membered heterocycloalkyl, C$_{6-10}$ aryl, 5-10 membered heteroaryl, halo, D, CN, OR$^{a40}$, and NR$^{c40}$R$^{d40}$; wherein said C$_{1-6}$ alkyl, C$_{3-10}$ cycloalkyl, 4-10 membered heterocycloalkyl, C$_{6-10}$ aryl, and 5-10 membered heteroaryl, are each optionally substituted with 1, 2, 3, or 4 substituents independently selected from R$^{41}$;

each R$^{41}$ is independently selected from C$_{1-6}$ alkyl, C$_{1-6}$ haloalkyl, halo, D, CN, OR$^{a41}$, and NR$^{c41}$R$^{d41}$;

each R$^{60}$ is independently selected from C$_{1-6}$ alkyl, C$_{1-6}$ haloalkyl, halo, D, CN, OR$^{a60}$, and NR$^{c60}$R$^{d60}$;

each R$^a$, R$^c$ and R$^d$ is independently selected from H, C$_{1-6}$ alkyl, and C$_{1-6}$ haloalkyl;

each R$^{a3}$, R$^{c3}$ and R$^{d3}$ is independently selected from H, C$_{1-6}$ alkyl, and C$_{1-6}$ haloalkyl;

each R$^{a4}$, R$^{b4}$, R$^{c4}$ and R$^{d4}$ is independently selected from H, C$_{1-6}$ alkyl, C$_{1-6}$ haloalkyl, C$_{3-10}$ cycloalkyl, 4-10 membered heterocycloalkyl, C$_{6-10}$ aryl and 5-10 membered heteroaryl; wherein said C$_{1-6}$ alkyl, C$_{3-10}$ cycloalkyl, 4-10 membered heterocycloalkyl, C$_{6-10}$ aryl and 5-10 membered heteroaryl, are each optionally substituted with 1, 2, 3, or 4 substituents independently selected from R$^{40}$;

or any R$^{c4}$ and R$^{d4}$ attached to the same N atom, together with the N atom to which they are attached, form a 4-, 5-, 6- or 7-membered heterocycloalkyl group optionally substituted with 1, 2, 3, or 4 substituents independently selected from R$^{40}$;

each R$^{j4}$ is independently selected from H, C$_{1-6}$ alkyl, C$_{1-6}$ haloalkyl, C$_{3-10}$ cycloalkyl, 4-10 membered heterocycloalkyl, C$_{6-10}$ aryl and 5-10 membered heteroaryl; wherein said C$_{1-6}$ alkyl, C$_{3-10}$ cycloalkyl, 4-10 membered heterocycloalkyl, C$_{6-10}$ aryl and 5-10 membered heteroaryl, are each optionally substituted with 1, 2, 3, or 4 substituents independently selected from R$^{40}$;

or any R$^{c4}$ and R$^{j4}$ attached to the same N atom, together with the N atom to which they are attached, form a 4-, 5-, 6- or 7-membered heterocycloalkyl group optionally substituted with 1, 2, 3, or 4 substituents independently selected from R$^{40}$;

each R$^{a6}$, R$^{c6}$, and R$^{d6}$ is independently selected from H, C$_{1-6}$ alkyl, C$_{1-6}$ haloalkyl, C$_{3-10}$ cycloalkyl, 4-10 membered heterocycloalkyl, C$_{6-10}$ aryl and 5-10 membered heteroaryl; wherein said C$_{1-6}$ alkyl, C$_{3-10}$ cycloalkyl, 4-10 membered heterocycloalkyl, C$_{6-10}$ aryl and 5-10 membered heteroaryl, are each optionally substituted with 1, 2, 3, or 4 substituents independently selected from R$^{60}$;

or any R$^{c6}$ and R$^{d6}$ attached to the same N atom, together with the N atom to which they are attached, form a 4-, 5-, 6- or 7-membered heterocycloalkyl group optionally substituted with 1, 2 or 3 substituents independently selected from R$^{60}$;

each R$^{a10}$, R$^{c10}$ and R$^{d10}$ is independently selected from H, C$_{1-6}$ alkyl, and C$_{1-6}$ haloalkyl;

each R$^{a20}$, R$^{b20}$, R$^{c20}$ and R$^{d20}$ is independently selected from H, C$_{1-6}$ alkyl, C$_{2-6}$ alkenyl, C$_{2-6}$ alkynyl, and C$_{1-6}$ haloalkyl; wherein said C$_{1-6}$ alkyl, C$_{2-6}$ alkenyl, and C$_{2-6}$ alkynyl, are each optionally substituted with 1, 2, 3, or 4 substituents independently selected from R$^{21}$;

each R$^{a21}$, R$^{c21}$ and R$^{d21}$, is independently selected from H, C$_{1-6}$ alkyl, and C$_{1-6}$ haloalkyl;

each R$^{a40}$, R$^{c40}$ and R$^{d40}$ is independently selected from H, C$_{1-6}$ alkyl, C$_{1-6}$ haloalkyl, C$_{3-10}$ cycloalkyl, 4-10 membered heterocycloalkyl, C$_{6-10}$ aryl and 5-10 membered heteroaryl; wherein said C$_{1-6}$ alkyl, C$_{3-10}$ cycloalkyl, 4-10 membered heterocycloalkyl, C$_{6-10}$ aryl and 5-10 membered heteroaryl, are each optionally substituted with 1, 2, 3, or 4 substituents independently selected from R$^{41}$;

or any R$^{c40}$ and R$^{d40}$ attached to the same N atom, together with the N atom to which they are attached, form a 4-, 5-, 6- or 7-membered heterocycloalkyl group optionally substituted with 1, 2, 3, or 4 substituents independently selected from R$^{41}$;

each R$^{a41}$, R$^{c41}$ and R$^{d41}$, is independently selected from H, C$_{1-6}$ alkyl, and C$_{1-6}$ haloalkyl; and each R$^{a60}$, R$^{c60}$ and R$^{d60}$ is independently selected from H, C$_{1-6}$ alkyl, and C$_{1-6}$ haloalkyl.

In another embodiment, the compound of Formula I is a compound of Formula II:

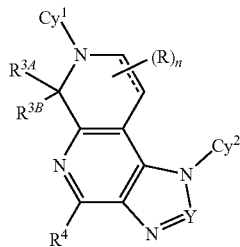

(II)

or a pharmaceutically acceptable salt thereof.

In an embodiment of a compound of Formula I or II, or a pharmaceutically acceptable salt thereof, ≡≡≡ represents a single bond or a double bond;

Y is N or $CR^6$;

each R is independently selected from $C_{1-6}$ alkyl, $C_{1-6}$ haloalkyl, halo, D, and CN;

n is 0, 1, or 2;

$Cy^1$ is selected from $C_{6-10}$ aryl and 5-10 membered heteroaryl; wherein the 5-10 membered heteroaryl each has at least one ring-forming carbon atom and 1 or 2 ring-forming heteroatoms independently selected from N and O; and wherein the $C_{6-10}$ aryl and 5-10 membered heteroaryl are each optionally substituted with 1, 2, or 3 substituents independently selected from $R^{10}$;

$R^{3A}$ and $R^{3B}$ are each independently selected from H, $C_{1-6}$ alkyl, $C_{1-6}$ haloalkyl, halo, D, and CN;

or $R^{3A}$ and $R^{3B}$ can be taken together with the carbon atom to which they are attached to form a C=O;

$R^4$ is selected from H, $C_{1-6}$ alkyl, $C_{1-6}$ haloalkyl, $C_{3-6}$ cycloalkyl, 4-6 membered heterocycloalkyl, phenyl, 5-6 membered heteroaryl, halo, D, CN, $OR^{a4}$, and $NR^{c4}R^{j4}$; wherein said $C_{1-6}$ alkyl, $C_{3-6}$ cycloalkyl, 4-6 membered heterocycloalkyl, phenyl, and 5-6 membered heteroaryl, are each optionally substituted with 1, 2, or 3 substituents independently selected from $R^{40}$;

$R^6$ is selected from H, $C_{1-6}$ alkyl, $C_{1-6}$ haloalkyl, halo, D, CN, $OR^{a6}$, and $NR^{c6}R^{d6}$; wherein said $C_{1-6}$ alkyl, is optionally substituted with 1, 2, or 3 substituents independently selected from $R^{60}$;

$Cy^2$ is selected from 4-8 membered heterocycloalkyl; wherein the 4-8 membered heterocycloalkyl has at least one ring-forming carbon atom and 1 or 2 ring-forming heteroatoms independently selected from N and O; and wherein the 4-8 membered heterocycloalkyl, is optionally substituted with 1, 2, or 3 substituents independently selected from $R^{20}$;

each $R^{10}$ is independently selected from $C_{1-6}$ alkyl, $C_{1-6}$ haloalkyl, halo, D, CN, $OR^{a10}$, and $NR^{c10}R^{d10}$;

each $R^{20}$ is independently selected from $C_{1-6}$ alkyl, $C_{2-6}$ alkenyl, $C_{2-6}$ alkynyl, $C_{1-6}$ haloalkyl, halo, D, CN, $OR^{a20}$, $C(O)R^{b20}$, $C(O)NR^{c20}R^{d20}$, and $NR^{c20}R^{d20}$; wherein said $C_{1-6}$ alkyl, is optionally substituted with 1, 2, 3, or 4 substituents independently selected from $R^{21}$;

each $R^{21}$ is independently selected from $C_{1-6}$ alkyl, $C_{1-6}$ haloalkyl, halo, D, CN, $OR^{a21}$, and $NR^{c21}R^{d21}$;

each $R^{40}$ is independently selected from $C_{1-6}$ alkyl, $C_{1-6}$ haloalkyl, $C_{3-6}$ cycloalkyl, 4-6 membered heterocycloalkyl, halo, D, CN, $OR^{a40}$, and $NR^{c40}R^{d40}$; wherein said $C_{1-6}$ alkyl, $C_{3-6}$ cycloalkyl, and 4-6 membered heterocycloalkyl, are each optionally substituted with 1, 2, or 3 substituents independently selected from $R^{41}$;

each $R^{41}$ is independently selected from $C_{1-6}$ alkyl, $C_{1-6}$ haloalkyl, halo, D, and CN;

each $R^{60}$ is independently selected from $C_{1-6}$ alkyl, $C_{1-6}$ haloalkyl, halo, D, CN, $OR^{a60}$, and $NR^{c60}R^{d60}$;

each $R^{a4}$, and $R^{c4}$ is independently selected from H, $C_{1-6}$ alkyl, $C_{1-6}$ haloalkyl, $C_{3-6}$ cycloalkyl, 4-6 membered heterocycloalkyl, phenyl and 5-6 membered heteroaryl; wherein said $C_{1-6}$ alkyl, $C_{3-6}$ cycloalkyl, 4-6 membered heterocycloalkyl, phenyl and 5-6 membered heteroaryl, are each optionally substituted with 1, 2, or 3 substituents independently selected from $R^{40}$;

each $R^{j4}$ is independently selected from H, $C_{1-6}$ alkyl, $C_{1-6}$ haloalkyl, $C_{3-6}$ cycloalkyl, 4-6 membered heterocycloalkyl, phenyl and 5-6 membered heteroaryl; wherein said $C_{1-6}$ alkyl, $C_{3-6}$ cycloalkyl, 4-6 membered heterocycloalkyl, phenyl and 5-6 membered heteroaryl, are each optionally substituted with 1, 2, 3, or 4 substituents independently selected from $R^{40}$;

or any $R^{c4}$ and $R^{j4}$ attached to the same N atom, together with the N atom to which they are attached, form a 4-, 5-, or 6-membered heterocycloalkyl group optionally substituted with 1, 2, 3, or 4 substituents independently selected from $R^{40}$;

each $R^{a6}$, $R^{c6}$, and $R^{d6}$ is independently selected from H, $C_{1-6}$ alkyl, and $C_{1-6}$ haloalkyl; wherein said $C_{1-6}$ alkyl, is optionally substituted with 1, 2, or 3 substituents independently selected from $R^{60}$;

each $R^{a10}$, $R^{c10}$ and $R^{d10}$ is independently selected from H, $C_{1-6}$ alkyl, and $C_{1-6}$ haloalkyl;

each $R^{a20}$, $R^{b20}$, $R^{c20}$ and $R^{d20}$ is independently selected from H, $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl, are each optionally substituted with 1, 2, 3, or 4 substituents independently selected from $R^{21}$;

each $R^{a21}$, $R^{c21}$ and $R^{d21}$, is independently selected from H, $C_{1-6}$ alkyl, and $C_{1-6}$ haloalkyl;

each $R^{a40}$, $R^{c40}$ and $R^{d40}$ is independently selected from H, $C_{1-6}$ alkyl, $C_{1-6}$ haloalkyl, $C_{3-6}$ cycloalkyl, and 4-6 membered heterocycloalkyl; wherein said $C_{1-6}$ alkyl, $C_{3-6}$ cycloalkyl, and 4-6 membered heterocycloalkyl, are each optionally substituted with 1, 2, or 3 substituents independently selected from $R^{41}$;

or any $R^{c40}$ and $R^{d40}$ attached to the same N atom, together with the N atom to which they are attached, form a 4-, 5-, or 6-membered heterocycloalkyl group optionally substituted with 1, 2, or 3 substituents independently selected from $R^{41}$; and each $R^{a60}$, $R^{c60}$ and $R^{d60}$ is independently selected from H, $C_{1-6}$ alkyl, and $C_{1-6}$ haloalkyl.

In yet another embodiment of a compound of Formula I or II, or a pharmaceutically acceptable salt thereof, ≡≡≡ represents a single bond or a double bond;

X is N;

Y is N, CH, or $C(C_{1-6}$ alkyl) optionally substituted with 1, 2, 3, or 4 substituents independently selected from $R^{60}$;

R is $C_{1-6}$ haloalkyl;

n is 0 or 1;

$Cy^1$ is $C_{6-10}$ aryl optionally substituted with 1 or 2 substituents independently selected from $R^{10}$;

$R^{3A}$ and $R^{3B}$ are H;

or $R^{3A}$ and $R^{3B}$ can be taken together with the carbon atom to which they are attached to form a C=O;

$R^4$ is selected from $OR^{a4}$, 4-6 membered heterocycloalkyl, and 5-6 membered heteroaryl, wherein said heterocycloalkyl and heteroaryl are each optionally substituted with 1, 2, 3, or 4 substituents independently selected from $R^{40}$;

$Cy^2$ is 4-8 membered heterocycloalkyl optionally substituted with 1, 2, or 3 substituents independently selected from $R^{20}$;

each $R^{10}$ is independently selected from $C_{1-6}$ alkyl, $C_{1-6}$ haloalkyl, halo, and OH.

each $R^{20}$ is independently selected from $C_{1-6}$ alkyl, $C_{1-6}$ haloalkyl, and $C(O)R^{b20}$, wherein said alkyl is optionally substituted with 1 or 2 substituents independently selected from $R^{21}$;

each $R^{21}$ is independently selected from $C_{1-6}$ haloalkyl, halo, CN, OH, and $NH_2$;

$R^{40}$ is independently selected from $C_{1-6}$ alkyl, OH, O($C_{1-6}$ alkyl), N($C_{1-6}$ alkyl)$_2$, NH($C_{1-6}$ alkyl), $NH_2$, and 4-6 membered heterocycloalkyl, wherein heterocycloalkyl is optionally substituted by $C_{1-6}$ alkyl;

each $R^{60}$ is independently selected from $C_{1-6}$ alkyl, $C_{1-6}$ haloalkyl, halo, CN, $OR^{a60}$, and $NR^{c60}R^{d60}$;

$R^{a4}$ is independently selected from H, $C_{1-6}$ alkyl, and $C_{1-6}$ haloalkyl, wherein $C_{1-6}$ alkyl is optionally substituted by $R^{40}$;

each $R^{b20}$ is independently selected from $C_{1-6}$ alkyl, $C_{2-6}$ alkenyl, and $C_{2-6}$ alkynyl; wherein said $C_{1-6}$ alkyl, $C_{2-6}$ alkenyl, and $C_{2-6}$ alkynyl, are each optionally substituted with halo; and each $R^{a60}$, $R^{c60}$ and $R^{d60}$ is independently selected from H and $C_{1-6}$ alkyl.

In still another embodiment, the compound of Formula I is a compound of Formula III:

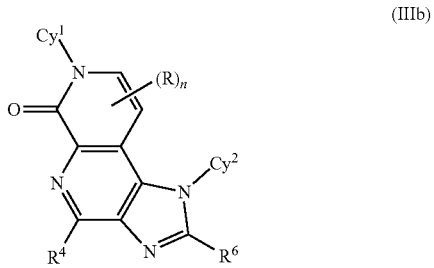

(III)

or a pharmaceutically acceptable salt thereof.

In an embodiment, the compound of Formula I is a compound of Formula IIIa:

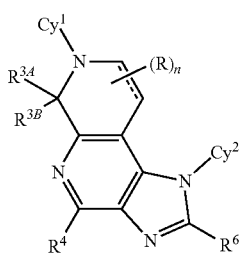

(IIIa)

or a pharmaceutically acceptable salt thereof.

In another embodiment, the compound of Formula I is a compound of Formula IIIb:

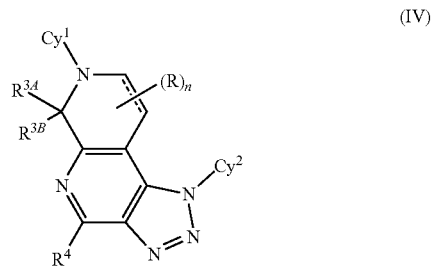

(IIIb)

or a pharmaceutically acceptable salt thereof.

In yet another embodiment, the compound of Formula I is a compound of Formula IV:

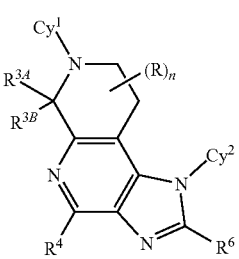

(IV)

or a pharmaceutically acceptable salt thereof.

In still another embodiment, === represents a single bond. In an embodiment, === represents a double bond.

In another embodiment, X is N. In another embodiment, X is $CR^5$.

In yet another embodiment, Y is CH or C($C_{1-6}$ alkyl) wherein $C_{1-6}$ alkyl is optionally substituted with 1, 2, 3, or 4 substituents independently selected from $R^{60}$. In still another embodiment, Y is N. In yet another embodiment, Y is $CR^6$.

In an embodiment each R is independently selected from $C_{1-6}$ alkyl, $C_{1-6}$ haloalkyl, halo, D, CN, $OR^a$, and $NR^cR^d$. In an embodiment each R is independently selected from $C_{1-6}$ alkyl, $C_{1-6}$ haloalkyl, halo, D, and CN;

In an embodiment, n is 0. In another embodiment, R is $C_{1-6}$ haloalkyl and n is 1. In an embodiment n is 0, 1, or 2.

In an embodiment, $Cy^1$ is selected from $C_{6-10}$ aryl and 5-10 membered heteroaryl; wherein the 5-10 membered heteroaryl each has at least one ring-forming carbon atom and 1 or 2 ring-forming heteroatoms independently selected from N and O; and wherein the $C_{6-10}$ aryl and 5-10 membered heteroaryl are each optionally substituted with 1, 2, or 3 substituents independently selected from $R^{10}$; In yet another embodiment, $Cy^1$ is $C_{6-10}$ aryl optionally substituted with 1 or 2 substituents independently selected from $R^{10}$.

In an embodiment, each $R^{10}$ is independently selected from $C_{1-6}$ alkyl, $C_{1-6}$ haloalkyl, halo, D, CN, $OR^{a10}$, and $NR^{c10}R^{d10}$. In still another embodiment, each $R^{10}$ is independently selected from $C_{1-6}$ alkyl, halo, and OH.

In an embodiment, $R^{3A}$ and $R^{3B}$ are taken together with the carbon atom to which they are attached to form a C=O. In another embodiment, $R^{3A}$ and $R^{3B}$ are each H. In another embodiment, $R^{3A}$ and $R^{3B}$ are each independently selected from H, $C_{1-6}$ alkyl, $C_{1-6}$ haloalkyl, halo, D, and CN;

In an embodiment, $R^4$ is selected from H, $C_{1-6}$ alkyl, $C_{1-6}$ haloalkyl, $C_{3-6}$ cycloalkyl, 4-6 membered heterocycloalkyl, phenyl, 5-6 membered heteroaryl, halo, D, CN, $OR^{a4}$, and $NR^{c4}R^{j4}$; wherein said $C_{1-6}$ alkyl, $C_{3-6}$ cycloalkyl, 4-6 membered heterocycloalkyl, phenyl, and 5-6 membered heteroaryl, are each optionally substituted with 1, 2, or 3 substituents independently selected from $R^{40}$. In yet another embodiment, $R^4$ is selected from $OR^{a4}$, 4-6 membered heterocycloalkyl, and 5-6 membered heteroaryl, wherein said heterocycloalkyl and heteroaryl are each optionally substituted with 1, 2, or 3 substituents independently selected from $R^{40}$.

In an embodiment, each $R^{40}$ is independently selected from $C_{1-6}$ alkyl, $C_{1-6}$ haloalkyl, $C_{3-6}$ cycloalkyl, 4-6 membered heterocycloalkyl, halo, D, CN, $OR^{a40}$, and $NR^{c40}R^{d40}$; wherein said $C_{1-6}$ alkyl, $C_{3-6}$ cycloalkyl, and 4-6 membered heterocycloalkyl, are each optionally substituted with 1, 2, or 3 substituents independently selected from $R^{41}$. In still another embodiment, each $R^{40}$ is independently selected from $C_{1-6}$ alkyl, $N(C_{1-6}$ alkyl$)_2$, $NH(C_{1-6}$ alkyl$)$, $NH_2$, and 4-6 membered heterocycloalkyl wherein heterocycloalkyl is optionally substituted with $R^{41}$.

In an embodiment, each $R^{41}$ is independently selected from $C_{1-6}$ alkyl, $C_{1-6}$ haloalkyl, halo, D, and CN. In an embodiment each $R^{41}$ is methyl.

In an embodiment each $R^{a4}$ is independently selected from H, $C_{1-6}$ alkyl, $C_{1-6}$ haloalkyl, $C_{3-6}$ cycloalkyl, 4-6 membered heterocycloalkyl, phenyl and 5-6 membered heteroaryl; wherein said $C_{1-6}$ alkyl, $C_{3-6}$ cycloalkyl, 4-6 membered heterocycloalkyl, phenyl and 5-6 membered heteroaryl, are each optionally substituted with 1, 2, or 3 substituents independently selected from $R^{40}$. In an embodiment, each $R^{a4}$ is independently selected from $C_{1-6}$ alkyl substituted with 4-6 membered heterocycloalkyl, wherein said heterocycloalkyl is optionally substituted with $C_{1-6}$ alkyl.

In an embodiment, each $R^{j4}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$. In an embodiment, each $R^{j4}$ is independently selected from $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$. In an embodiment, each $R^{j4}$ is independently selected from H, $C_{1-6}$ alkyl, $C_{1-6}$ haloalkyl, $C_{3-6}$ cycloalkyl, 4-6 membered heterocycloalkyl, phenyl and 5-6 membered heteroaryl; wherein said $C_{1-6}$ alkyl, $C_{3-6}$ cycloalkyl, 4-6 membered heterocycloalkyl, phenyl and 5-6 membered heteroaryl, are each optionally substituted with 1, 2, 3, or 4 substituents independently selected from $R^{40}$. In an embodiment, each $R^{j4}$ is independently selected from $C_{1-6}$ alkyl, $C_{1-6}$ haloalkyl, $C_{3-6}$ cycloalkyl, 4-6 membered heterocycloalkyl, phenyl and 5-6 membered heteroaryl; wherein said $C_{1-6}$ alkyl, $C_{3-6}$ cycloalkyl, 4-6 membered heterocycloalkyl, phenyl and 5-6 membered heteroaryl, are each optionally substituted with 1, 2, 3, or 4 substituents independently selected from $R^{40}$.

In an embodiment, $R^5$ is selected from H, $C_{1-6}$ alkyl, $C_{1-6}$ haloalkyl, halo, D, and CN. In an embodiment $R^5$ is selected from H and $C_{1-6}$ alkyl.

In an embodiment $R^6$ is selected from H, $C_{1-6}$ alkyl, $C_{1-6}$ haloalkyl, halo, D, CN, $OR^{a6}$, and $NR^{c6}R^{d6}$; wherein said $C_{1-6}$ alkyl, is optionally substituted with 1, 2, or 3 substituents independently selected from $R^{60}$. In an embodiment $R^6$ is selected from H and $C_{1-6}$ alkyl; wherein said $C_{1-6}$ alkyl, is optionally substituted with 1 or 2 substituents independently selected from $R^{60}$.

In an embodiment, each $R^{60}$ is independently selected from $C_{1-6}$ alkyl, $C_{1-6}$ haloalkyl, halo, D, CN, $OR^{a60}$, and $NR^{c60}R^{d60}$. In an embodiment, each $R^{60}$ is independently selected from $NH_2$, $NHCH_3$, and $N(CH_3)_2$.

In another embodiment, $Cy^2$ is 4-8 membered heterocycloalkyl optionally substituted with 1, 2, or 3 substituents independently selected from $R^{20}$. In another embodiment, $Cy^2$ is 4-6 membered heterocycloalkyl optionally substituted with 1 or 2 substituents independently selected from $R^{20}$.

In an embodiment, each $R^{20}$ is independently selected from $C_{1-6}$ alkyl, $C_{2-6}$ alkenyl, $C_{2-6}$ alkynyl, $C_{1-6}$ haloalkyl, halo, D, CN, $OR^{a20}$, $C(O)R^{b20}$, $C(O)NR^{c20}R^{d20}$, and $NR^{c20}R^{d20}$; wherein said $C_{1-6}$ alkyl, is optionally substituted with 1, 2, 3, or 4 substituents independently selected from $R^{21}$. In yet another embodiment, each $R^{20}$ is independently selected from $C_{1-6}$ alkyl and $C(O)R^{b20}$, wherein said alkyl is optionally substituted with 1 or 2 substituents independently selected from $R^{21}$.

In an embodiment, each $R^{21}$ is independently selected from $C_{1-6}$ alkyl, $C_{1-6}$ haloalkyl, halo, D, CN, $OR^{a21}$, and $NR^{b21}R^{d21}$. In still another embodiment, each $R^{21}$ is independently selected from $C_{1-6}$ haloalkyl, halo, CN, OH, and $NH_2$.

In an embodiment, each $R^{b20}$ is independently selected from $C_{1-6}$ alkyl, $C_{2-6}$ alkenyl, and $C_{2-6}$ alkynyl; wherein said $C_{1-6}$ alkyl, $C_{2-6}$ alkenyl, and $C_{2-6}$ alkynyl, are each optionally substituted with halo. In an embodiment, each $R^{b20}$ is independently selected from $C_{2-6}$ alkenyl, and $C_{2-6}$ alkynyl; wherein said $C_{2-6}$ alkenyl, and $C_{2-6}$ alkynyl, are each optionally substituted with halo.

In yet another embodiment, $Cy^2$ is selected from:

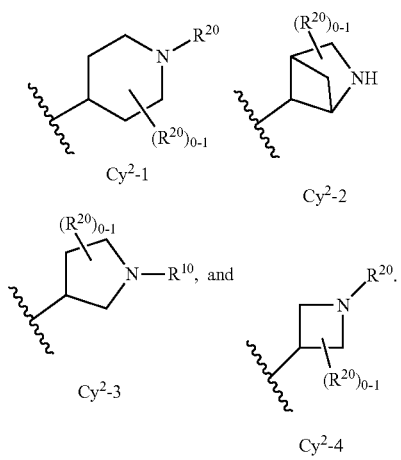

In an embodiment, $Cy^2$ is $Cy^2$-1. In another embodiment, $Cy^2$ is $Cy^2$-2. In yet another embodiment, $Cy^2$ is $Cy^2$-3. In still another embodiment, $Cy^2$ is $Cy^2$-4.

In an embodiment, each $R^{20}$ is independently selected from $C_{1-6}$ alkyl, $C_{1-6}$ haloalkyl, halo, D, CN, OH, and $NH_2$.

In an embodiment, the compound of Formula I is selected from:

2-(1-acryloyl-4-(4-(3-(dimethylamino)azetidin-1-yl)-7-(3-hydroxpaphthalen-1-yl)-6-oxo-6,7-dihydro-1H-imidazo[4,5-c][1,7]naphthyridin-1-yl)piperidin-2-yl)acetonitrile;

2-(1-(but-2-ynoyl)-4-(4-(3-(dimethylamino)azetidin-1-yl)-7-(3-hydroxpaphthalen-1-yl)-6-oxo-6,7-dihydro-1H-imidazo[4,5-c][1,7]naphthyridin-1-yl)piperidin-2-yl)acetonitrile;

1-(2-azabicyclo[2.1.1]hexan-5-yl)-4-(3-(dimethylamino)azetidin-1-yl)-7-(3-hydroxynaphthalen-1-yl)-2-(2-(methylamino)ethyl)-1,7-dihydro-6H-imidazo[4,5-c][1,7]naphthyridin-6-one;

2-(1-acryloyl-4-(4-(3-(dimethylamino)azetidin-1-yl)-7-(naphthalen-1-yl)-6,7,8,9-tetrahydro-1H-imidazo[4,5-c][1,7]naphthyridin-1-yl)piperidin-2-yl)acetonitrile;

2-(1-acryloyl-4-(4-(3-(dimethylamino)azetidin-1-yl)-7-(3-hydroxpaphthalen-1-yl)-6,7,8,9-tetrahydro-1H-imidazo[4,5-c][1,7]naphthyridin-1-yl)piperidin-2-yl)acetonitrile;

2-(1-acryloyl-4-(4-(3-(dimethylamino)azetidin-1-yl)-7-(naphthalen-1-yl)-6-oxo-8-(trifluoromethyl)-6,7-dihydro-1H-imidazo[4,5-c][1,7]naphthyridin-1-yl)piperidin-2-yl)acetonitrile;

2-(1-acryloyl-4-(4-(2-methylpyridin-3-yl)-7-(naphthalen-1-yl)-6-oxo-8-(trifluoromethyl)-6,7-dihydro-1H-imidazo[4,5-c][1,7]naphthyridin-1-yl)piperidin-2-yl)acetonitrile;

2-(1-acryloyl-4-(7-(3-chloro-2-methylphenyl)-4-(1-(1-methylpyrrolidin-2-yl)ethoxy)-6-oxo-8-(trifluoromethyl)-6,7-dihydro-1H-imidazo[4,5-c][1,7]naphthyridin-1-yl)piperidin-2-yl)acetonitrile;

2-(1-(but-2-ynoyl)-4-(7-(3-chloro-2-methylphenyl)-4-(1-(1-methylpyrrolidin-2-yl)ethoxy)-6-oxo-8-(trifluoromethyl)-6,7-dihydro-1H-imidazo[4,5-c][1,7]naphthyridin-1-yl)piperidin-2-yl)acetonitrile;

2-(4-(7-(3-chloro-2-methylphenyl)-4-(1-(1-methylpyrrolidin-2-yl)ethoxy)-6-oxo-8-(trifluoromethyl)-6,7-dihydro-1H-imidazo[4,5-c][1,7]naphthyridin-1-yl)-1-(2-fluoroacryloyl)piperidin-2-yl)acetonitrile;

2-(1-acryloyl-4-(7-(3-chloro-2-methylphenyl)-4-(3-(dimethylamino)-3-methylazetidin-1-yl)-6-oxo-8-(trifluoromethyl)-6,7-dihydro-1H-[1,2,3]triazolo[4,5-c][1,7]naphthyridin-1-yl)piperidin-2-yl)acetonitrile; and 2-(4-(7-(3-chloro-2-methylphenyl)-4-(3-(dimethylamino)-3-methylazetidin-1-yl)-6-oxo-8-(trifluoromethyl)-6,7-dihydro-1H-[1,2,3]triazolo[4,5-c][1,7]naphthyridin-1-yl)-1-((E)-4-fluorobut-2-enoyl)piperidin-2-yl)acetonitrile;

or a pharmaceutically acceptable salt thereof.

In another embodiment, the compound of Formula I is selected from:

2-((2S,4S)-1-acryloyl-4-(4-(3-(dimethylamino)azetidin-1-yl)-7-(3-hydroxynaphthalen-1-yl)-6-oxo-6,7-dihydro-1H-imidazo[4,5-c][1,7]naphthyridin-1-yl)piperidin-2-yl)acetonitrile;

2-((2S,4S)-1-(but-2-ynoyl)-4-(4-(3-(dimethylamino)azetidin-1-yl)-7-(3-hydroxynaphthalen-1-yl)-6-oxo-6,7-dihydro-1H-imidazo[4,5-c][1,7]naphthyridin-1-yl)piperidin-2-yl)acetonitrile;

1-((1R,4R,5S)-2-azabicyclo[2.1.1]hexan-5-yl)-4-(3-(dimethylamino)azetidin-1-yl)-7-(3-hydroxynaphthalen-1-yl)-2-(2-(methylamino)ethyl)-1,7-dihydro-6H-imidazo[4,5-c][1,7]naphthyridin-6-one;

2-((2S,4S)-1-acryloyl-4-(4-(3-(dimethylamino)azetidin-1-yl)-7-(naphthalen-1-yl)-6,7,8,9-tetrahydro-1H-imidazo[4,5-c][1,7]naphthyridin-1-yl)piperidin-2-yl)acetonitrile;

2-((2S,4S)-1-acryloyl-4-(4-(3-(dimethylamino)azetidin-1-yl)-7-(3-hydroxynaphthalen-1-yl)-6,7,8,9-tetrahydro-1H-imidazo[4,5-c][1,7]naphthyridin-1-yl)piperidin-2-yl)acetonitrile;

2-((2S,4S)-1-acryloyl-4-(4-(3-(dimethylamino)azetidin-1-yl)-7-(naphthalen-1-yl)-6-oxo-8-(trifluoromethyl)-6,7-dihydro-1H-imidazo[4,5-c][1,7]naphthyridin-1-yl)piperidin-2-yl)acetonitrile;

2-((2S)-1-acryloyl-4-(4-(2-methylpyridin-3-yl)-7-(naphthalen-1-yl)-6-oxo-8-(trifluoromethyl)-6,7-dihydro-1H-imidazo[4,5-c][1,7]naphthyridin-1-yl)piperidin-2-yl)acetonitrile;

2-((2S,4S)-1-acryloyl-4-(7-(3-chloro-2-methylphenyl)-4-((S)-1-((S)-1-methylpyrrolidin-2-yl)ethoxy)-6-oxo-8-(trifluoromethyl)-6,7-dihydro-1H-imidazo[4,5-c][1,7]naphthyridin-1-yl)piperidin-2-yl)acetonitrile;

2-((2S,4S)-1-(but-2-ynoyl)-4-(7-(3-chloro-2-methylphenyl)-4-((S)-1-((S)-1-methylpyrrolidin-2-yl)ethoxy)-6-oxo-8-(trifluoromethyl)-6,7-dihydro-1H-imidazo[4,5-c][1,7]naphthyridin-1-yl)piperidin-2-yl)acetonitrile;

2-((2S,4S)-4-(7-(3-chloro-2-methylphenyl)-4-((S)-1-((S)-1-methylpyrrolidin-2-yl)ethoxy)-6-oxo-8-(trifluoromethyl)-6,7-dihydro-1H-imidazo[4,5-c][1,7]naphthyridin-1-yl)-1-(2-fluoroacryloyl)piperidin-2-yl)acetonitrile;

2-((2S,4S)-1-acryloyl-4-(7-(3-chloro-2-methylphenyl)-4-(3-(dimethylamino)-3-methylazetidin-1-yl)-6-oxo-8-(trifluoromethyl)-6,7-dihydro-1H-[1,2,3]triazolo[4,5-c][1,7]naphthyridin-1-yl)piperidin-2-yl)acetonitrile; and 2-((2S,4S)-4-(7-(3-chloro-2-methylphenyl)-4-(3-(dimethylamino)-3-methylazetidin-1-yl)-6-oxo-8-(trifluoromethyl)-6,7-dihydro-1H-[1,2,3]triazolo[4,5-c][1,7]naphthyridin-1-yl)-1-((E)-4-fluorobut-2-enoyl)piperidin-2-yl)acetonitrile;

or a pharmaceutically acceptable salt thereof.

In another aspect, provided herein is a pharmaceutical composition comprising the compound of Formula I, or a pharmaceutically acceptable salt thereof, and a pharmaceutically acceptable carrier.

In an aspect, provided herein is a method of inhibiting a KRAS protein harboring a G12C mutation, said method comprising contacting a compound of the instant disclosure with KRAS.

In another aspect, provided herein is a method of inhibiting a KRAS protein harboring a G12D mutation, said method comprising contacting a compound of the instant disclosure with KRAS.

In yet another aspect, provided herein is a method of inhibiting a KRAS protein harboring a G12V mutation, said method comprising contacting a compound of the instant disclosure with KRAS.

In an embodiment, compounds of the Formulae herein are compounds of the Formulae or pharmaceutically acceptable salts thereof.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula I can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$— includes both —NR(CR'R")$_n$— and —(CR'R")$_n$—NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted," unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl," refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene," employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1,4-diyl, butan-1,3-diyl, butan-1,2-diyl, 2-methyl-propan-1,3-diyl and the like.

The term "alkoxy," employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms. The term "$C_{n-m}$ dialkoxy" refers to a linking group of formula —O—($C_{n-m}$ alkyl)-O—, the alkyl group of which has n to m carbons. Example dialkyoxy groups include —OCH$_2$CH$_2$O— and OCH$_2$CH$_2$CH$_2$O—. In some embodiments, the two O atoms of a $C_{n-m}$ dialkoxy group may be attached to the same B atom to form a 5- or 6-membered heterocycloalkyl group.

The term "alkylthio," employed alone or in combination with other terms, refers to a group of formula —S-alkyl, wherein the alkyl group is as defined above.

The term "amino," employed alone or in combination with other terms, refers to a group of formula —NH$_2$, wherein the hydrogen atoms may be substituted with a substituent described herein. For example, "alkylamino" can refer to —NH(alkyl) and —N(alkyl)$_2$.

The term "carbonyl," employed alone or in combination with other terms, refers to a —C(=O)— group, which also may be written as C(O).

The term "cyano" or "nitrile" refers to a group of formula —C≡N, which also may be written as —CN.

The term "carbamyl," as used herein, refers to a —NHC(O)O— or —OC(O)NH— group, wherein the carbon atom is doubly bound to one oxygen atom, and singly bound to a nitrogen and second oxygen atom.

The term "sulfonyl" refers to a —SO$_2$— group wherein a sulfur atom is doubly bound to two oxygen atoms.

The terms "halo" or "halogen," used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CH_2F$, $CCl_3$, $CHCl_2$, $C_2Cl_5$ and the like. In some embodiments, the haloalkyl group is a fluoroalkyl group.

The term "haloalkoxy," employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" or "oxy" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "oxidized" in reference to a ring-forming N atom refers to a ring-forming N-oxide.

The term "oxidized" in reference to a ring-forming S atom refers to a ring-forming sulfonyl or ring-forming sulfinyl.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments aryl groups have 6 carbon atoms. In some embodiments aryl groups have 10 carbon atoms. In some embodiments, the aryl group is phenyl. In some embodiments, the aryl group is naphthyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, isoxazolyl, thiazolyl, imidazolyl, furanyl, thiophenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, isoindolyl, benzothiophenyl, benzofuranyl, benzisoxazolyl, imidazo[1,2-b]thiazolyl, purinyl, and the like. In some embodiments, the heteroaryl group is pyridone (e.g., 2-pyridone).

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl, isoindolyl, and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 2,5-diazobicyclo[2.2.1]heptanyl; pyrrolidinyl; hexahydropyrrolo[3,4-b]pyrrol-1(2H)-yl; 1,6-dihydropyridinyl; morpholinyl; azetidinyl; piperazinyl; and 4,7-diazaspiro[2.5]octan-7-yl.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term "compound" as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17th Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups.

The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6th Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high-performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

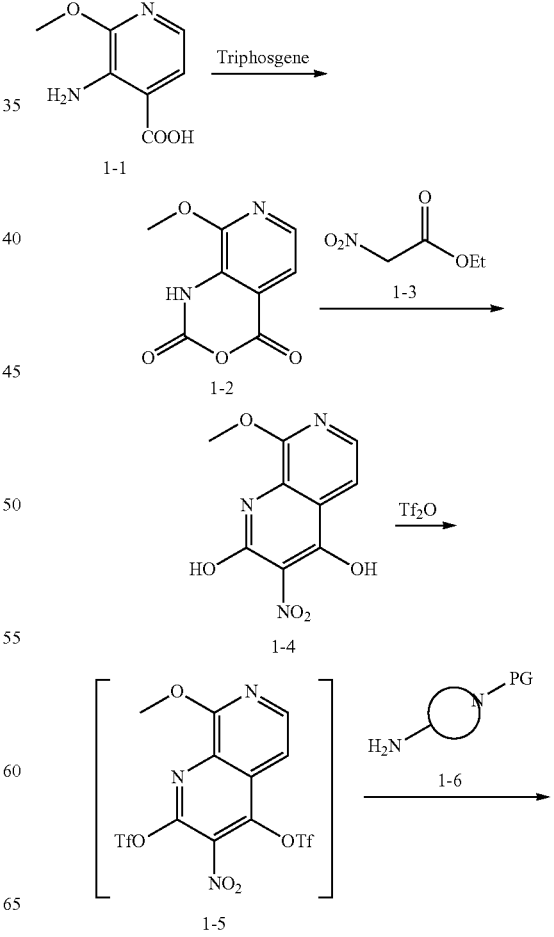

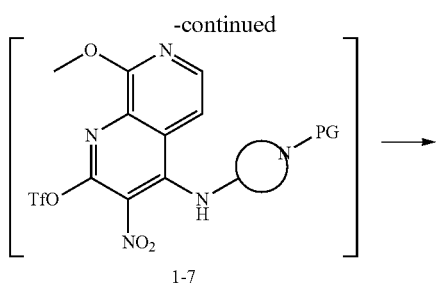

1-7

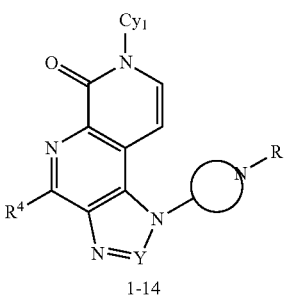

1-14

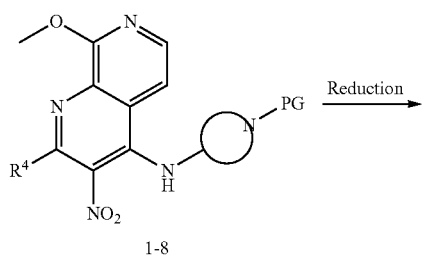

1-8

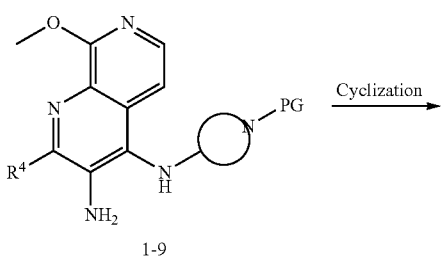

1-9

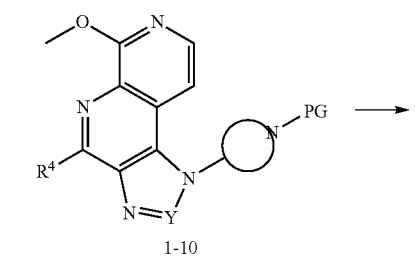

1-10

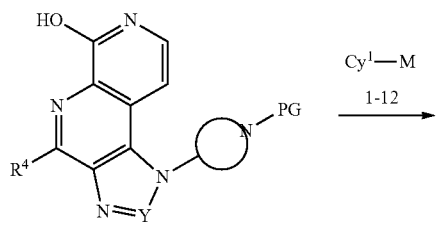

1-11

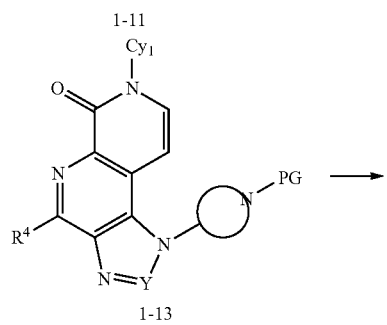

1-13

Compound 1-2 can be prepared by treating 1-1 with reagents such as triphosgene. Intermediate 1-2 can then react with ester 1-3 to deliver the nitro compound 1-4, which can be treated with an appropriate reagent (e.g. $Tf_2O$) to afford intermediate 1-5. A $S_NAr$ reaction of intermediate 1-5 with amine 1-6 (PG is an appropriate protecting group, such as Boc) can be carried out to generate intermediate 1-7. Another suitable reagent (such as alkylamine) was added in situ to install $R^4$. 1-8 can be reduced in the presence reducing agents (e.g. $H_2$ with Pd/C) to provide 1-9. Cyclization of 1-9 was performed with appropriate reagent (e.g. triethyl orthoformate, sodium nitrite) to form compound 1-10, which can be deprotected to afford 1-11. Intermediate 1-13 can be prepared by a cross coupling reaction between 1-11 and an adduct of formula 1-12, in which M is a boronic acid, under standard Chan Lam coupling conditions (e.g., in the presence of a Cu catalyst and a suitable base). Compound 1-13 can first undergo a deprotection of protecting group PG, followed by functionalization of the resulting amine (such as coupling with acid chloride, e.g. acryloyl chloride) then afford compound 1-14.

Scheme 2

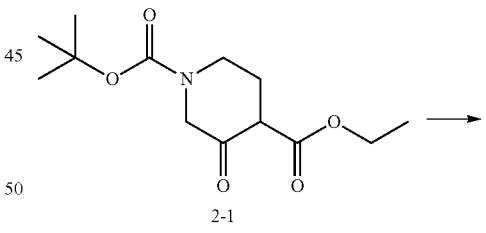

2-1

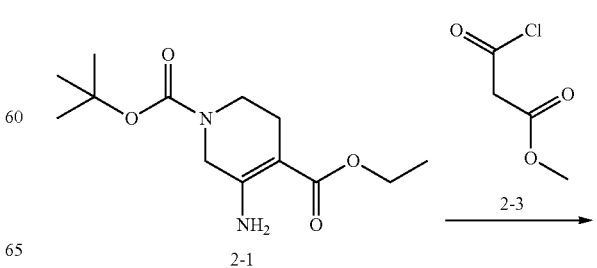

2-1

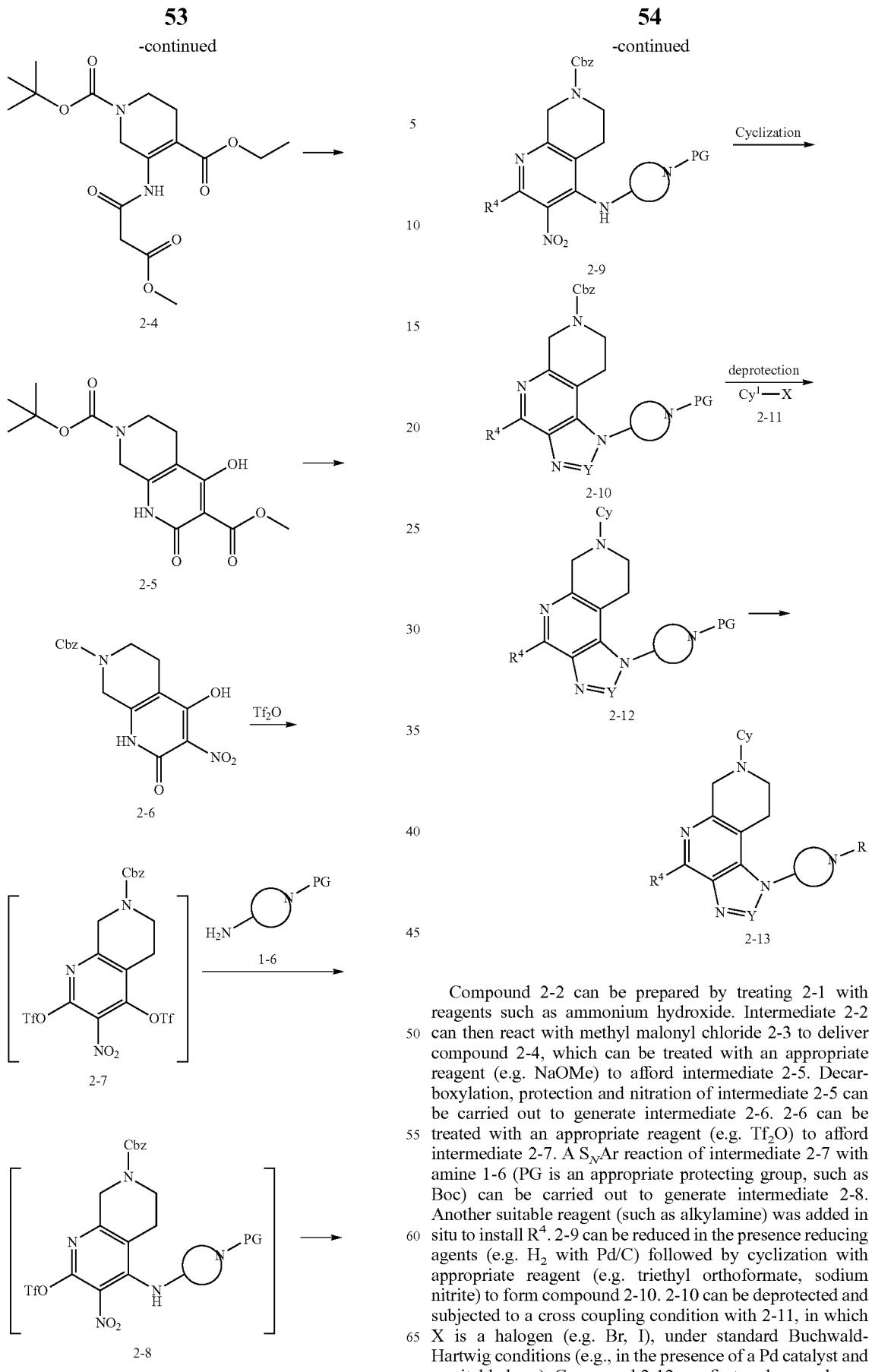

Compound 2-2 can be prepared by treating 2-1 with reagents such as ammonium hydroxide. Intermediate 2-2 can then react with methyl malonyl chloride 2-3 to deliver compound 2-4, which can be treated with an appropriate reagent (e.g. NaOMe) to afford intermediate 2-5. Decarboxylation, protection and nitration of intermediate 2-5 can be carried out to generate intermediate 2-6. 2-6 can be treated with an appropriate reagent (e.g. Tf$_2$O) to afford intermediate 2-7. A S$_N$Ar reaction of intermediate 2-7 with amine 1-6 (PG is an appropriate protecting group, such as Boc) can be carried out to generate intermediate 2-8. Another suitable reagent (such as alkylamine) was added in situ to install R$^4$. 2-9 can be reduced in the presence reducing agents (e.g. H$_2$ with Pd/C) followed by cyclization with appropriate reagent (e.g. triethyl orthoformate, sodium nitrite) to form compound 2-10. 2-10 can be deprotected and subjected to a cross coupling condition with 2-11, in which X is a halogen (e.g. Br, I), under standard Buchwald-Hartwig conditions (e.g., in the presence of a Pd catalyst and a suitable base). Compound 2-12 can first undergo a deprotection of protecting group PG, followed by functionalization of the resulting amine (such as coupling with acid chloride, e.g. acryloyl chloride) to afford compound 2-13.
Scheme 3
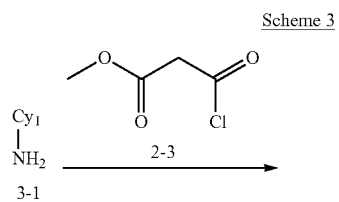
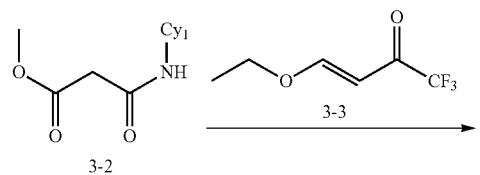
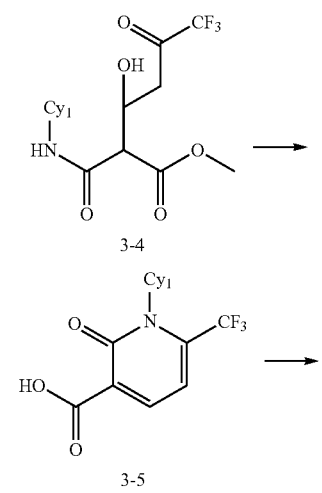
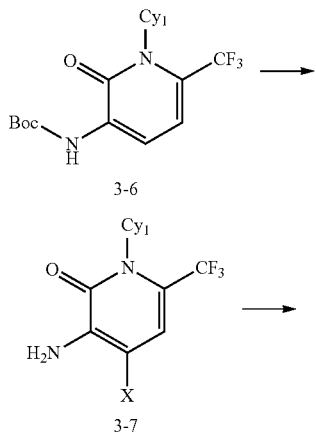
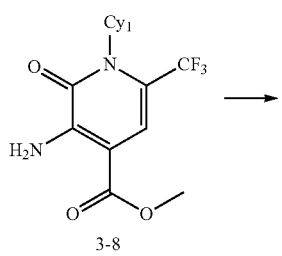
-continued
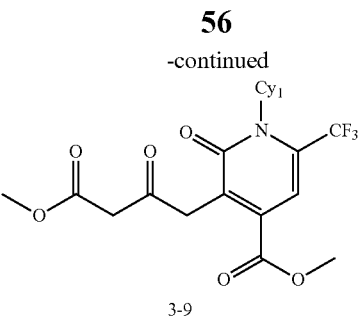
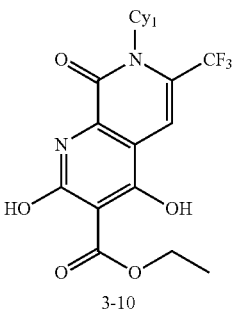
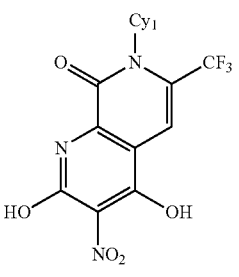
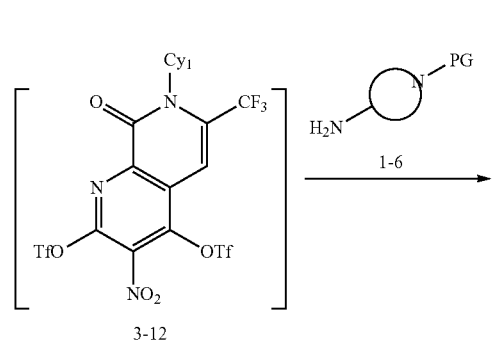
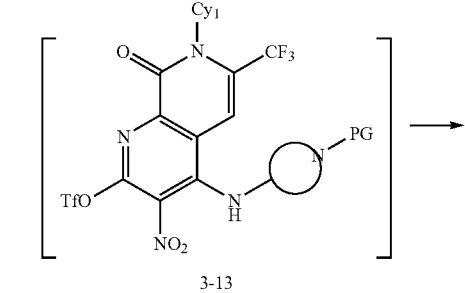

-continued

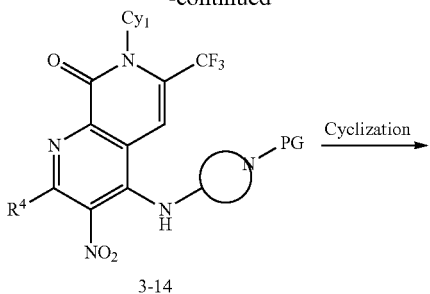
3-14

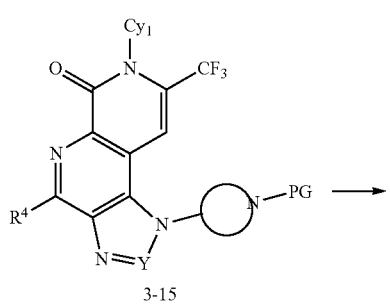
3-15

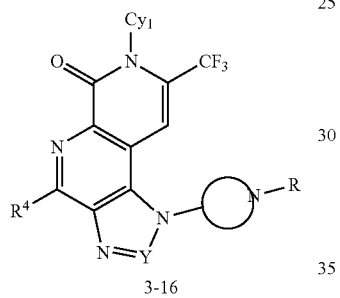
3-16

Scheme 4

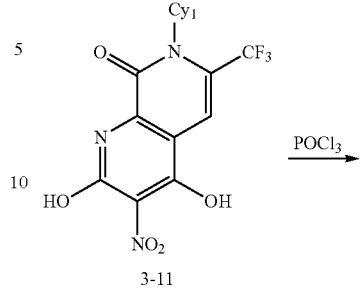
3-11

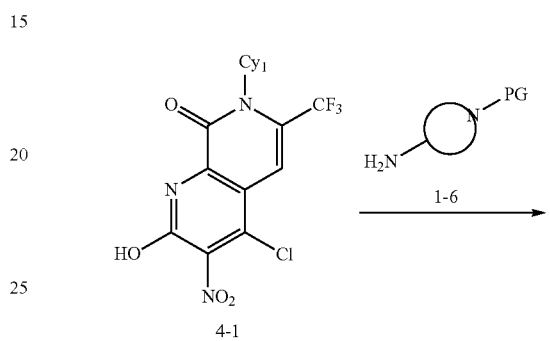
4-1

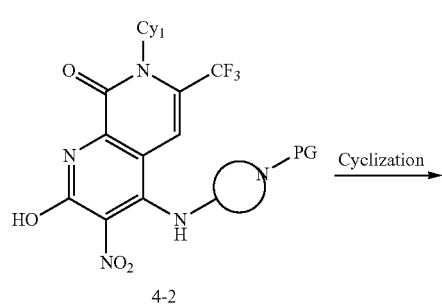
4-2

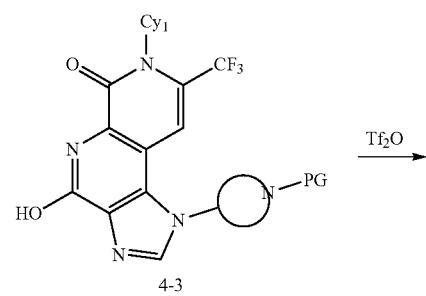
4-3

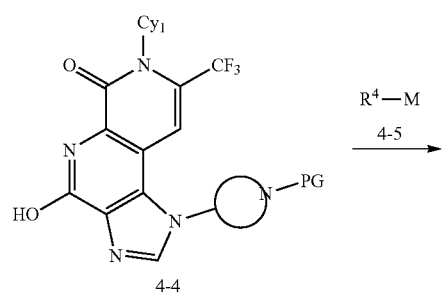
4-4

Compound 3-2 can be prepared by treating 3-1 with methyl malonyl chloride 2-3, which can be treated with 3-3 to afford intermediate 3-4. Condensation of intermediate 3-4 can be carried out with an acid catalyst such as p-toluenesulfonic acid monohydrate, followed by hydrolysis, to prepare compound 3-5. 3-5 can be treated with standard Curtius rearrangement conditions to afford 3-6, which was then deprotected and halogenated with an appropriate reagent, such as NIS, to afford compound 3-7. A carbonylation reaction (e.g., in the presence of a palladium catalyst) of 3-7 can deliver compound 3-8, which was then treated with 2-3 to deliver 3-9. Intermediate 3-9 can undergo a cyclization reaction under basic conditions (e.g. NaOEt in EtOH) to access compound 3-10. Decarboxylation, and nitration of intermediate 3-10 can be carried out to generate intermediate 3-11. 3-11 can be treated with an appropriate reagent (e.g. Tf$_2$O) to afford intermediate 3-12. A S$_N$Ar reaction of intermediate 3-12 with amine 1-6 (PG is an appropriate protecting group, such as Boc) can be carried out to generate intermediate 3-13. Another suitable reagent (such as alkylamine) was added in situ to install R$^4$. 3-14 can be reduced in the presence reducing agents (e.g. H$_2$ with Pd/C) followed by cyclization with appropriate reagent (e.g. triethyl orthoformate, sodium nitrite) to form compound 3-15. Compound 3-15 can first undergo a deprotection of protecting group PG, followed by functionalization of the resulting amine (such as coupling with acid chloride, e.g. acryloyl chloride) to afford compound 3-16.

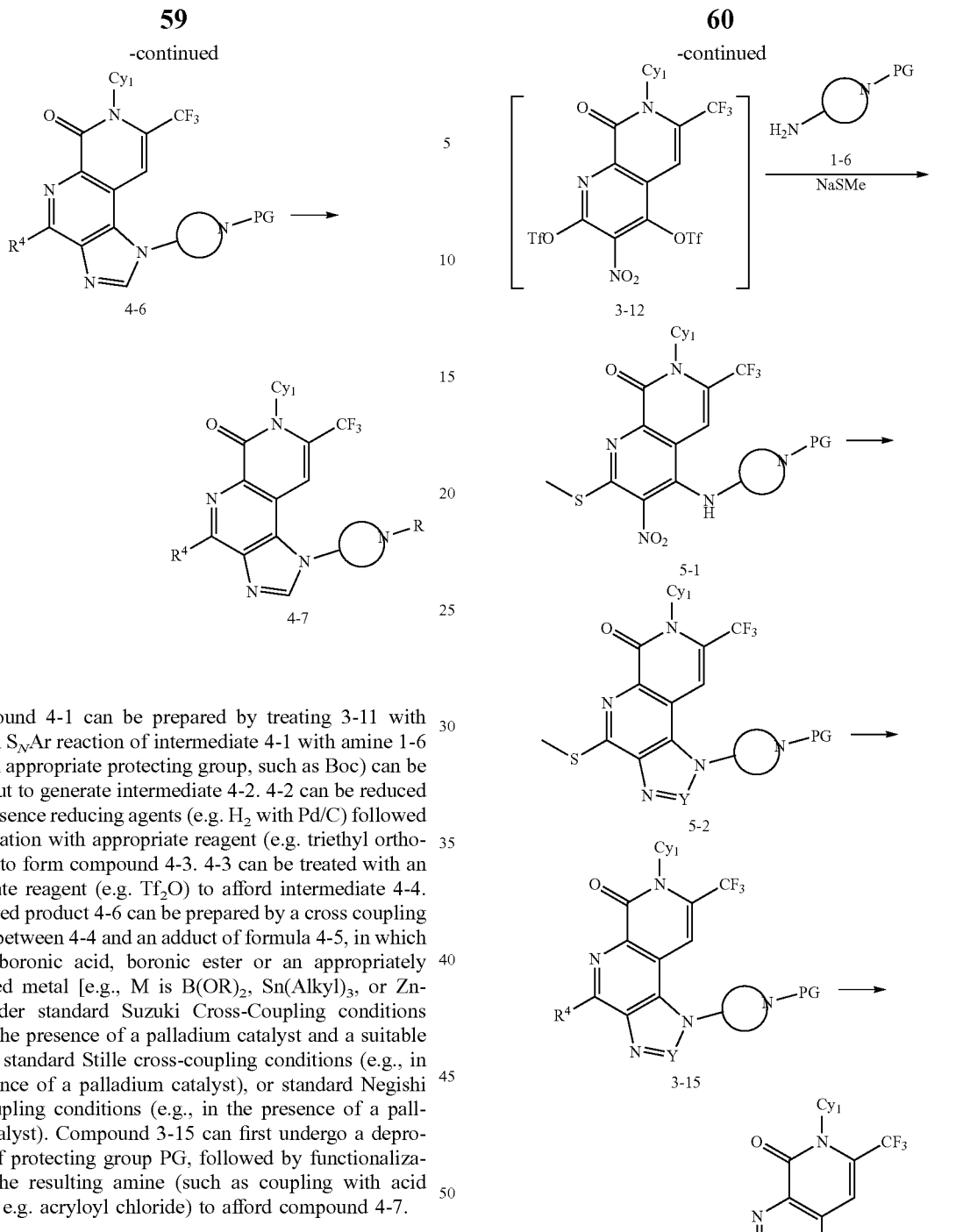

Compound 4-1 can be prepared by treating 3-11 with POCl₃, A S_NAr reaction of intermediate 4-1 with amine 1-6 (PG is an appropriate protecting group, such as Boc) can be carried out to generate intermediate 4-2. 4-2 can be reduced in the presence reducing agents (e.g. H₂ with Pd/C) followed by cyclization with appropriate reagent (e.g. triethyl orthoformate) to form compound 4-3. 4-3 can be treated with an appropriate reagent (e.g. Tf₂O) to afford intermediate 4-4. The desired product 4-6 can be prepared by a cross coupling reaction between 4-4 and an adduct of formula 4-5, in which M is a boronic acid, boronic ester or an appropriately substituted metal [e.g., M is B(OR)₂, Sn(Alkyl)₃, or Zn-Hal], under standard Suzuki Cross-Coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palldium catalyst). Compound 3-15 can first undergo a deprotection of protecting group PG, followed by functionalization of the resulting amine (such as coupling with acid chloride, e.g. acryloyl chloride) to afford compound 4-7.

Scheme 5

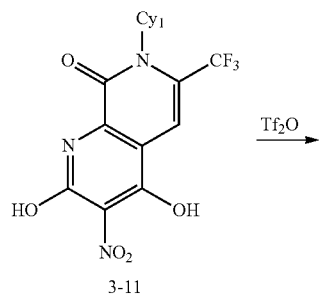

Compound 3-11 can be treated with Tf₂O, then a S_NAr reaction of intermediate 3-12 with amine 1-6 (PG is an appropriate protecting group, such as Boc) followed by a suitable reagent such as NaSMe can deliver compound 5-1. 5-1 can be reduced in the presence reducing agents (e.g. H₂ with Pd/C) followed by cyclization with appropriate reagent (e.g. triethyl orthoformate, sodium nitrite) to form compound 5-2. 5-2 can be treated with an appropriate oxidative reagent (e.g. mCPBA) followed by adding an appropriate reagent (e.g. alkylamine, alcohol) with base (such as LiHMDS) to afford intermediate 3-15. Compound 3-15 can first undergo a deprotection of protecting group PG, followed by functionalization of the resulting amine (such as coupling with acid chloride, e.g. acryloyl chloride) then afford compound 3-16.

KRAS Protein

The Ras family is comprised of three members; KRAS, NRAS and HRAS. RAS mutant cancers account for about 25% of human cancers. KRAS is the most frequently mutated isoform in human cancers: 85% of all RAS mutations are in KRAS, 12% in NRAS, and 3% in HRAS (Simanshu, D. et al. Cell 170.1 (2017):17-33). KRAS mutations are prevalent amongst the top three most deadly cancer types: pancreatic (97%), colorectal (44%), and lung (30%) (Cox, A. D. et al. Nat Rev Drug Discov (2014) 13:828-51). The majority of RAS mutations occur at amino acid residues/codons 12, 13, and 61; Codon 12 mutations are most frequent in KRAS. The frequency of specific mutations varied between RAS genes and G12D mutations are most predominant in KRAS whereas Q61R and G12R mutations are most frequent in NRAS and HRAS. Furthermore, the spectrum of mutations in a RAS isoform differs between cancer types. For example, KRAS G12D mutations predominate in pancreatic cancers (51%), followed by colorectal adenocarcinomas (45%) and lung cancers (17%) (Cox, A. D. et al. Nat Rev Drug Discov (2014) 13:828-51). In contrast, KRAS G12C mutations predominate in non-small cell lung cancer (NSCLC) comprising 11-16% of lung adenocarcinomas (nearly half of mutant KRAS is G12C), as well as 2-5% of pancreatic and colorectal adenocarcinomas, respectively (Cox, A. D. et al. Nat Rev Drug Discov (2014) 13:828-51). Genomic studies using shRNA knockdown thousands of genes across hundreds of cancer cell lines have demonstrated that cancer cells exhibiting KRAS mutations are highly dependent on KRAS function for cell growth (McDonald, R. et al. Cell 170 (2017): 577-592). Taken together, these findings suggested that KRAS mutations play a critical role in human cancers, therefore development of the inhibitors targeting mutant KRAS may be useful in the clinical treatment of diseases that have characterized by a KRAS mutation.

Methods of Use

The cancer types in which KRAS harboring G12C, G12V, and G12D mutations are implicated include, but are not limited to: carcinomas (e.g., pancreatic, colorectal, lung, bladder, gastric, esophageal, breast, head and neck, cervical skin, thyroid); hematopoietic malignancies (e.g., myeloproliferative neoplasms (MPN), myelodysplastic syndrome (MDS), chronic and juvenile myelomonocytic leukemia (CMML and JMML), acute myeloid leukemia (AML), acute lymphocytic leukemia (ALL) and multiple myeloma (MM)); and other neoplasms (e.g., glioblastoma and sarcomas). In addition, KRAS mutations were found in acquired resistance to anti-EGFR therapy (Knickelbein, K. et al. Genes & Cancer, (2015): 4-12). KRAS mutations were found in immunological and inflammatory disorders (Fernandez-Medarde, A. et al. Genes & Cancer, (2011): 344-358) such as Ras-associated lymphoproliferative disorder (RALD) or juvenile myelomonocytic leukemia (JMML) caused by somatic mutations of KRAS or NRAS.

Compounds of the present disclosure can inhibit the activity of KRAS. For example, compounds of the present disclosure can be used to inhibit activity of KRAS in a cell or in an individual or patient in need of inhibition of the enzyme by administering an inhibiting amount of one or more compounds of the present disclosure to the cell, individual, or patient.

In an aspect, provided herein is a method of inhibiting KRAS activity, said method comprising administering to a patient in need thereof a therapeutically effective amount of a compound of any of the formulae disclosed herein.

In another aspect, provided herein is a method of treating a KRAS-mediated disease or disorder in a subject in need thereof comprising administering to the subject a therapeutically effective amount of the compound of any of the formulae disclosed herein.

In an embodiment, the disease or disorder is an immunological or inflammatory disorder.

In another embodiment, the immunological or inflammatory disorder is Ras-associated lymphoproliferative disorder or juvenile myelomonocytic leukemia caused by somatic mutations of KRAS.

In an aspect, provided herein is a method of treating a disease or disorder associated with inhibiting a KRAS protein harboring a G12C mutation, said method comprising administering to a patient in need thereof a therapeutically effective amount of a compound of any of the formulae disclosed herein, or pharmaceutically acceptable salt thereof.

In another aspect, provided herein is a method of treating cancer in a subject in need thereof comprising administering to the subject a therapeutically effective amount of the compound of any of the formulae disclosed herein.

In an embodiment, the cancer is selected from carcinomas, hematological cancers, sarcomas, and glioblastoma.

In another embodiment, the hematological cancer is selected from myeloproliferative neoplasms, myelodysplastic syndrome, chronic and juvenile myelomonocytic leukemia, acute myeloid leukemia, acute lymphocytic leukemia, and multiple myeloma.

In yet another embodiment, the carcinoma is selected from pancreatic, colorectal, lung, bladder, gastric, esophageal, breast, head and neck, cervical, skin, and thyroid.

In still another aspect, provided herein is a method of treating a disease or disorder associated with inhibiting a KRAS protein harboring a G12C mutation, said method comprising administering to a patient in need thereof a therapeutically effective amount of the compound of any of the formulae disclosed herein, or a pharmaceutically acceptable salt thereof.

In another aspect, provided herein is a method of treating cancer in a patient in need thereof comprising administering to the patient a therapeutically effective amount of the compounds disclosed herein wherein the cancer is characterized by an interaction with a KRAS protein harboring a G12C mutation.

In another aspect, provided herein is a method for treating a disease or disorder associated with inhibition of KRAS interaction or a mutant thereof in a patient in need thereof comprising the step of administering to the patient a compound disclosed herein, or a pharmaceutically acceptable salt thereof, or a composition comprising a compound disclosed herein or a pharmaceutically acceptable salt thereof, in combination with another therapy or therapeutic agent as described herein.

In some embodiments, the compounds of the disclosure have selective inhibitory activity for KRAS over other RAS proteins. In some embodiments, the selectivity of the compounds of the disclosure for KRAS over other RAS proteins is 10-fold to 25-fold, or 25-fold to 50-fold.

As KRAS inhibitors, the compounds of the present disclosure are useful in the treatment of various diseases associated with abnormal expression or activity of KRAS. Compounds that inhibit KRAS will be useful in providing a means of preventing the growth or inducing apoptosis in tumors, particularly by inhibiting angiogenesis. It is therefore anticipated that compounds of the present disclosure will prove useful in treating or preventing proliferative disorders such as cancers. In particular, tumors with activating mutants of receptor tyrosine kinases or upregulation of receptor tyrosine kinases may be particularly sensitive to the inhibitors.

In certain embodiments, the disclosure provides a method for treating a KRAS-mediated disorder in a subject in need thereof, comprising the step of administering to said patient a compound according to the invention, or a pharmaceutically acceptable composition thereof.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET), myelodysplasia syndrome (MDS), T-cell acute lymphoblastic lymphoma (T-ALL), multiple myeloma, cutaneous T-cell lymphoma, adult T-cell leukemia, Waldenstrom's Macroglubulinemia, hairy cell lymphoma, marginal zone lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, lymphosarcoma, leiomyosarcoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, mesothelioma, pavicellular and non-pavicellular carcinoma, bronchial adenoma and pleuropulmonary blastoma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (exocrine pancreatic carcinoma, ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), colorectal cancer, gall bladder cancer and anal cancer.

Exemplary genitourinary tract cancers include cancers of the kidney (adenocarcinoma, Wilm's tumor [nephroblastoma], renal cell carcinoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma) and urothelial carcinoma.

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors, neuro-ectodermal tumors), and spinal cord (neurofibroma, meningioma, glioma, sarcoma), neuroblastoma, Lhermitte-Duclos disease and pineal tumors.

Exemplary gynecological cancers include cancers of the breast (ductal carcinoma, lobular carcinoma, breast sarcoma, triple-negative breast cancer, HER2-positive breast cancer, inflammatory breast cancer, papillary carcinoma), uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers, tumors of the eye, tumors of the lips and mouth and squamous head and neck cancer.

The compounds of the present disclosure can also be useful in the inhibition of tumor metastases.

In addition to oncogenic neoplasms, the compounds of the invention are useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes. In some embodiments, the present disclosure provides a method for treating a patient suffering from a skeletal and chondrocyte disorder.

In some embodiments, compounds described herein can be used to treat Alzheimer's disease, HIV, or tuberculosis.

As used herein, the term "8p11 myeloproliferative syndrome" is meant to refer to myeloid/lymphoid neoplasms associated with eosinophilia and abnormalities of FGFR1.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the KRAS enzyme with a compound described herein includes the administration of a compound described herein to an individual or patient, such as a human, having KRAS, as well as, for example, introducing a compound described herein into a sample containing a cellular or purified preparation containing the KRAS protein.

As used herein, the term "individual," "subject," or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

As used herein, the term "treating" or "treatment" refers to inhibiting a disease; for example, inhibiting a disease, condition, or disorder in an individual who is experiencing or displaying the pathology or symptomology of the disease, condition, or disorder (i.e., arresting further development of the pathology and/or symptomology) or ameliorating the disease; for example, ameliorating a disease, condition, or disorder in an individual who is experiencing or displaying the pathology or symptomology of the disease, condition, or disorder (i.e., reversing the pathology and/or symptomology) such as decreasing the severity of the disease.

The term "prevent," "preventing," or "prevention" as used herein, comprises the prevention of at least one symptom associated with or caused by the state, disease or disorder being prevented.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with compounds described herein for treatment of KRAS-associated diseases, disorders or conditions, or diseases or conditions as described herein. The agents can be combined with the present compounds in a single dosage form, or the agents can be administered simultaneously or sequentially as separate dosage forms.

Compounds described herein can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-βR, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the solid forms of the KRAS inhibitor as described herein can be combined with inhibitors of kinases associated with the PIK3/Akt/mTOR signaling pathway, such as PI3K, Akt (including Akt1, Akt2 and Akt3) and mTOR kinases.

In some embodiments, compounds described herein can be used in combination with one or more inhibitors of the enzyme or protein receptors such as HPK1, SBLB, TUT4, A2A/A2B, CD47, CDK2, STING, ALK2, LIN28, ADAR1, MAT2a, RIOK1, HDAC8, WDR5, SMARCA2, and DCLK1 for the treatment of diseases and disorders. Exemplary diseases and disorders include cancer, infection, inflammation and neurodegenerative disorders.

In some embodiments, compounds described herein can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat. For treating cancer and other proliferative diseases, compounds described herein can be used in combination with targeted therapies, including JAK kinase inhibitors (Ruxolitinib, additional JAK1/2 and JAK1-selective, baricitinib or INCB39110), Pim kinase inhibitors (e.g., LGH447, INCB053914 and SGI-1776), PI3 kinase inhibitors including PI3K-delta selective and broad spectrum PI3K inhibitors (e.g., INCB50465 and INCB54707), PI3K-gamma inhibitors such as PI3K-gamma selective inhibitors, MEK inhibitors, CSF1R inhibitors (e.g., PLX3397 and LY3022855), TAM receptor tyrosine kinases inhibitors (Tyro-3, Axl, and Mer; e.g., INCB81776), angiogenesis inhibitors, interleukin receptor inhibitors, Cyclin Dependent kinase inhibitors, BRAF inhibitors, mTOR inhibitors, proteasome inhibitors (Bortezomib, Carfilzomib), HDAC-inhibitors (panobinostat, vorinostat), DNA methyl transferase inhibitors, dexamethasone, bromo and extra terminal family members inhibitors (for example, bromodomain inhibitors or BET inhibitors, such as OTX015, CPI-0610, INCB54329 or INCB57643), LSD1 inhibitors (e.g., GSK2979552, INCB59872 and INCB60003), arginase inhibitors (e.g., INCB1158), indoleamine 2,3-dioxygenase inhibitors (e.g., epacadostat, NLG919 or BMS-986205), PARP inhibitors (e.g., olaparib or rucaparib), and inhibitors of BTK such as ibrutinib.

In addition, for treating cancer and other proliferative diseases, compounds described herein can be used in combination with targeted therapies such as, e.g., c-MET inhibitors (e.g., capmatinib), an anti-CD19 antibody (e.g., tafasitamab), an ALK2 inhibitor (e.g., INCB00928); or combinations thereof.

For treating cancer and other proliferative diseases, compounds described herein can be used in combination with chemotherapeutic agents, agonists or antagonists of nuclear receptors, or other anti-proliferative agents. Compounds described herein can also be used in combination with a medical therapy such as surgery or radiotherapy, e.g., gamma-radiation, neutron beam radiotherapy, electron beam radiotherapy, proton therapy, brachytherapy, and systemic radioactive isotopes.

Examples of suitable chemotherapeutic agents include any of: abarelix, abiraterone, afatinib, aflibercept, aldesleukin, alemtuzumab, alitretinoin, allopurinol, altretamine, amidox, amsacrine, anastrozole, aphidicolon, arsenic trioxide, asparaginase, axitinib, azacitidine, bevacizumab, bexarotene, baricitinib, bendamustine, bicalutamide, bleomycin, bortezombi, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, didox, docetaxel, doxorubicin, droloxafine, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lonafarnib, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, niraparib, nofetumomab, oserelin, oxaliplatin, paclitaxel, pamidronate, panitumumab, panobinostat, pazopanib, pegaspargase, pegfilgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafine, revlimid, rituximab, rucaparib, ruxolitinib, sorafenib, streptozocin, sunitinib, sunitinib maleate, tamoxifen, tegafur, temozolomide, teniposide, testolactone, tezacitabine, thalidomide, thioguanine, thiotepa, tipifarnib, topotecan, toremifene, tositumomab, trastuzumab, tretinoin, triapine, trimidox, triptorelin, uracil mustard, valrubicin, vandetanib, vinblastine, vincristine, vindesine, vinorelbine, vorinostat, veliparib, talazoparib, and zoledronate.

In some embodiments, compounds described herein can be used in combination with immune checkpoint inhibitors. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3 (e.g., INCAGN2385), TIM3 (e.g., INCB2390), VISTA, PD-1, PD-L1 and PD-L2. In some embodiments, the immune checkpoint molecule is a stimulatory checkpoint molecule selected from CD27, CD28, CD40, ICOS, OX40 (e.g., INCAGN1949), GITR (e.g., INCAGN1876) and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is a small molecule PD-L1 inhibitor. In some embodiments, the small molecule PD-L1 inhibitor has an IC50 less than 1 µM, less than 100 nM, less than 10 nM or less than 1 nM in a PD-L1 assay described in US Patent Publication Nos. US 20170107216, US 20170145025, US 20170174671, US 20170174679, US 20170320875, US 20170342060, US 20170362253, and US 20180016260, each of which is incorporated by reference in its entirety for all purposes.

In some embodiments, the inhibitor of an immune checkpoint molecule is an inhibitor of PD-1, e.g., an anti-PD-1 monoclonal antibody. In some embodiments, the anti-PD-1 monoclonal antibody is MGA012 (retifanlimab), nivolumab, pembrolizumab (also known as MK-3475), pidilizumab, SHR-1210, PDR001, ipilumimab or AMP-224. In some embodiments, the anti-PD-1 monoclonal antibody is nivolumab or pembrolizumab. In some embodiments, the anti-PD1 antibody is pembrolizumab. In some embodiments, the anti-PD1 antibody is nivolumab. In some embodiments, the anti-PD-1 monoclonal antibody is MGA012 (retifanlimab). In some embodiments, the anti-PD1 antibody is SHR-1210. Other anti-cancer agent(s) include antibody therapeutics such as 4-1BB (e.g. urelumab, utomilumab).

In some embodiments, the compounds of the disclosure can be used in combination with INCB086550.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MED14736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

In some embodiments, the compounds described herein can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Suitable antiviral agents contemplated for use in combination with compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2', 3'-dicleoxy-5-fluoro-cytidene); DAPD, ((−)-beta-D-2,6, -diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with compounds described herein for the treatment of cancer include chemotherapeutic agents, targeted cancer therapies, immunotherapies or radiation therapy. Compounds described herein may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds described herein. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

The compounds described herein may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with KRAS inhibitors. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with KRAS inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds described herein include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with KRAS inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds described herein. In some embodiments, the JAK inhibitor is selective for JAK1 over JAK2 and JAK3.

Other suitable agents for use in combination with compounds described herein include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with compounds described herein include steroids including 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

Other suitable agents for use in combination with compounds described herein include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds described herein may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-L1 and PD-1 antibodies, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of the present disclosure can be used in combination with bone marrow transplant for the treatment of a variety of tumors of hematopoietic origin.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

As provided throughout, the additional compounds, inhibitors, agents, etc. can be combined with the present compound in a single or continuous dosage form, or they can be administered simultaneously or sequentially as separate dosage forms.

Formulation, Dosage Forms and Administration

When employed as pharmaceuticals, the compounds of the present disclosure can be administered in the form of pharmaceutical compositions. Thus, the present disclosure provides a composition comprising a compound of Formula I, II, or any of the formulas as described herein, a compound as recited in any of the claims and described herein, or a pharmaceutically acceptable salt thereof, or any of the embodiments thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the present disclosure or a pharmaceutically acceptable salt thereof, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Labeled Compounds and Assay Methods

Another aspect of the present invention relates to labeled compounds of the disclosure (radio-labeled, fluorescent-labeled, etc.) that would be useful not only in imaging techniques but also in assays, both in vitro and in vivo, for localizing and quantitating KRAS protein in tissue samples, including human, and for identifying KRAS ligands by inhibition binding of a labeled compound. Substitution of one or more of the atoms of the compounds of the present disclosure can also be useful in generating differentiated ADME (Adsorption, Distribution, Metabolism and Excretion). Accordingly, the present invention includes KRAS binding assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula I or II can be optionally substituted with deuterium atoms, such as —$CD_3$ being substituted for —$CH_3$). In some embodiments, alkyl groups in Formula I or II can be perdeuterated.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro adenosine receptor labeling and competition assays, compounds that incorporate $^3$H, $^{14}$C, $^{82}$Br, $^{125}$I, $^{131}$I or $^{35}$S can be useful. For radio-imaging applications $^{11}$C, $^{18}$F, $^{125}$I, $^{123}$I, $^{124}$I, $^{131}$I, $^{75}$Br, $^{76}$Br or $^{77}$Br can be useful.

It is understood that a "radio-labeled" or "labeled compound" is a compound that has incorporated at least one radionuclide. In some embodiments, the radionuclide is selected from $^3$H, $^{14}$C, $^{125}$I, $^{35}$S and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the invention can be used in a screening assay to identify and/or evaluate compounds. For example, a newly synthesized or identified compound (i.e., test compound) which is labeled can be evaluated for its ability to bind a KRAS protein by monitoring its concentration variation when contacting with the KRAS, through tracking of the labeling. For example, a test compound (labeled) can be evaluated for its ability to reduce binding of another compound which is known to bind to a KRAS protein (i.e., standard compound). Accordingly, the ability of a test compound to compete with the standard compound for binding to the KRAS protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, e.g., in the treatment or prevention of diseases or disorders associated with the activity of KRAS, such as cancer or infections, which include one or more containers containing a pharmaceutical composition comprising a therapeutically effective amount of a compound of Formula I, II, or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of KRAS according to at least one assay described herein.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check.

The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 µm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 µm particle size, 19×100 mm column, eluting with mobile phase A: 0.15% NH₄OH in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute."

The following abbreviations may be used herein: AcOH (acetic acid); Ac₂O (acetic anhydride); aq. (aqueous); atm. (atmosphere(s)); Boc (t-butoxycarbonyl); BOP ((benzotriazol-1-yloxy)tris(dimethylamino)phosphonium hexafluorophosphate); br (broad); Cbz (carboxybenzyl); calc. (calculated); d (doublet); dd (doublet of doublets); DBU (1,8-diazabicyclo[5.4.0]undec-7-ene); DCM (dichloromethane); DIAD (N,N'-diisopropyl azidodicarboxylate); DIEA (N,N-diisopropylethylamine); DIPEA or DIEA (N,N-diisopropylethylamine); DIBAL (diisobutylaluminium hydride); DMF (N,N-dimethylformamide); Et (ethyl); EtOAc (ethyl acetate); FCC (flash column chromatography); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); IPA (isopropyl alcohol); J (coupling constant); LCMS (liquid chromatography—mass spectrometry); LDA (lithium diisopropylamide); m (multiplet); M (molar); mCPBA (3-chloroperoxybenzoic acid); MS (Mass spectrometry); Me (methyl); MeCN (acetonitrile); MeOH (methanol); mg (milligram(s)); min. (minutes(s)); mL (milliliter(s)); mmol (millimole(s)); N (normal); NCS (N-chlorosuccinimide); nM (nanomolar); NMP (N-methylpyrrolidinone); NMR (nuclear magnetic resonance spectroscopy); OTf (trifluoromethanesulfonate); Ph (phenyl); pM (picomolar); RP-HPLC (reverse phase high performance liquid chromatography); r.t. (room temperature), s (singlet); t (triplet or tertiary); TBS (tert-butyldimethylsilyl); tert (tertiary); tt (triplet of triplets); TFA (trifluoroacetic acid); THF (tetrahydrofuran); µg (microgram(s)); µL (microliter(s)); µM (micromolar); wt % (weight percent). Brine is saturated aqueous sodium chloride. In vacuo is under vacuum.

Example 1. 2-((2S,4S)-1-acryloyl-4-(4-(3-(dimethylamino)azetidin-1-yl)-7-(3-hydroxynaphthalen-1-yl)-6-oxo-6,7-dihydro-1H-imidazo[4,5-c][1,7]naphthyridin-1-yl)piperidin-2-yl)acetonitrile

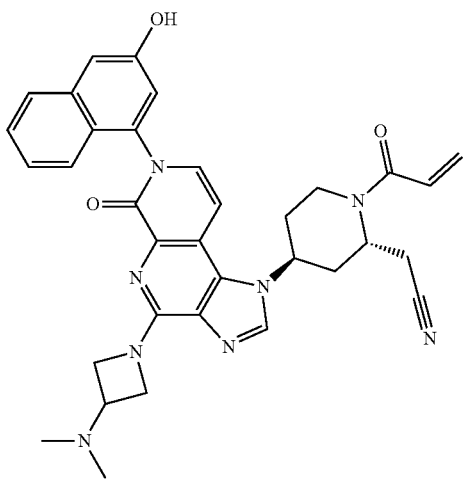 [SMILES: C=CC(=O)N1CC[C@H](n2cnc3c(N4CC(N(C)C)C4)nc4c(=O)n(-c5cc(O)cc6ccccc56)ccc4c32)C[C@H]1CC#N]

Step 1. 8-methoxy-2H-pyrido[3,4-d][1,3]oxazine-2,4(1H)-dione

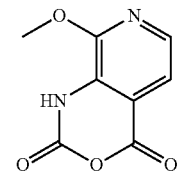

Triphosgene (4.41 g, 14.87 mmol) was added to a solution of 3-amino-2-methoxyisonicotinic acid (5.0 g, 29.7 mmol) in THF (100 ml) and then the reaction was stirred at 80° C. for 2 h. The reaction mixture was cooled with ice water and then hexanes was added and stirred for 10 min. The resulting solid was filtrated and washed with ethyl acetate to provide the desired product as a solid (5.0 g). LC-MS calculated for $C_8H_7N_2O_4$ (M+H)⁺: m/z=195.0; found 195.1.

Step 2. 8-methoxy-3-nitro-1,7-naphthyridine-2,4-diol

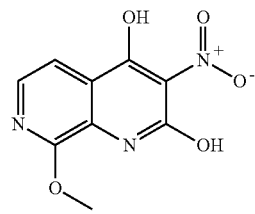

DIPEA (8.28 ml, 47.4 mmol) was added to a solution of ethyl 2-nitroacetate (5.30 mL, 47.4 mmol) in toluene (40.0 ml) at r.t. and stirred for 10 min. 8-methoxy-2H-pyrido[3,4-d][1,3]oxazine-2,4(1H)-dione (4.6 g, 23.69 mmol) was then added to the reaction mixture and the reaction was stirred at 100° C. for 12 h. The reaction was cooled with ice water and the resulting solid was filtered, then washed with small amount of ethyl acetate to provide the desired as a yellow solid (2.0 g, 36%). LC-MS calculated for $C_9H_8N_3O_5$ (M+H)$^+$: m/z=238.0; found 238.2.

Step 3. tert-butyl (2S,4S)-4-(((benzyloxy)carbonyl)amino)-2-(2-(tert-butoxy)-2-oxoethyl)piperidine-1-carboxylate

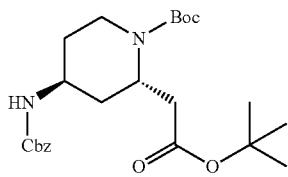 [SMILES: CC(C)(C)OC(=O)C[C@@H]1C[C@@H](NC(=O)OCc2ccccc2)CCN1C(=O)OC(C)(C)C]

To a solution of tert-butyl (2S,4S)-4-amino-2-(2-(tert-butoxy)-2-oxoethyl)piperidine-1-carboxylate (12.56 g, 39.9 mmol) in DCM (200 mL) was added N-(Benzyloxycarbonyloxy)succinimide (10.45 g, 41.9 mmol) followed by DIPEA (7.67 ml, 43.9 mmol). The mixture was stirred at r.t. overnight then diluted with EtOAc, washed with water, brine, then dried over $Na_2SO_4$. The organic layer was then concentrated and used in next step without further purification. LC-MS calculated for $C_{24}H_{37}N_2O_6$ (M+H)$^+$: m/z=449.3; found 349.2.

Step 4. 2-((2S,4S)-4-(((benzyloxy)carbonyl)amino)-1-(tert-butoxycarbonyl)piperidin-2-yl)acetic acid

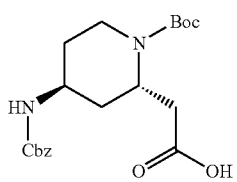 [SMILES: CC(C)(C)OC(=O)N1CC[C@H](NC(=O)OCc2ccccc2)C[C@H]1CC(=O)O]

tert-Butyl (2S,4S)-4-(((benzyloxy)carbonyl)amino)-2-(2-(tert-butoxy)-2-oxoethyl)piperidine-1-carboxylate (10.3 g, 22.96 mmol) in 500 mL of round bottom flask was added 50 mL of TFA. The reaction mixture was stirred at r.t. overnight. Solvent was removed under vacuum, the residue was dissolved in EtOAc, washed with sat. $NaHCO_3$ solution, brine, then dried over $Na_2SO_4$. The organic layer was then concentrated, the residue was dissolved in DCM (200 ml). To this solution TEA (15.96 ml, 115 mmol) was added, then di-tert-butyl dicarbonate (6.50 g, 29.8 mmol) was added. After full conversion, the reaction was acidified to pH=4 with 1N HCl. The mixture was extract with EtOAc, washed with brine, dried over $Na_2SO_4$. The organic layer was then concentrated and used in next step without further purification. LC-MS calculated for $C_{20}H_{28}N_2O_6Na$ (M+Na)$^+$: m/z=415.2; found 415.3.

Step 5. tert-butyl (2S,4S)-2-(2-amino-2-oxoethyl)-4-(((benzyloxy)carbonyl)amino)piperidine-1-carboxylate

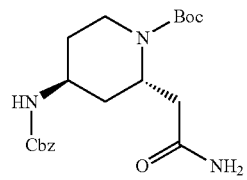 [SMILES: CC(C)(C)OC(=O)N1CC[C@H](NC(=O)OCc2ccccc2)C[C@H]1CC(N)=O]

To a THF (80 mL) solution of 2-((2S,4S)-4-(((benzyloxy)carbonyl)amino)-1-(tert-butoxycarbonyl)piperidin-2-yl)acetic acid (7.85 g, 20 mmol) was added DIPEA (13.97 ml, 80 mmol). The mixture was cooled to 0° C., then isobutyl chloroformate (5.78 ml, 44.0 mmol) was added dropwise. After stirring at 0° C. for 10 min, ammonium hydroxide (12.98 ml, 100 mmol) was added. The reaction mixture was stirred for 10 min before extracted with EtOAc. The organic layer was washed with water, brine and dried over $Na_2SO_4$. The organic layer was then concentrated and purified on silica gel (0-7% MeOH in $CH_2Cl_2$) to provide the desired product. LCMS calculated for $C_{20}H_{30}N_3O_5$ (M+H)$^+$: m/z=392.1; found 292.2.

Step 6. tert-butyl (2S,4S)-4-(((benzyloxy)carbonyl)amino)-2-(cyanomethyl)piperidine-1-carboxylate

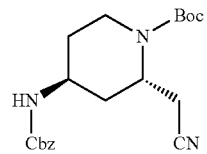

To a THF (80 mL) solution of tert-butyl (2S,4S)-2-(2-amino-2-oxoethyl)-4-(((benzyloxy)carbonyl)amino)piperidine-1-carboxylate (7.48 g, 19.1 mmol) was added TEA (5.32 ml, 38.2 mmol). The mixture was cooled to 0° C., then TFAA (3.24 ml, 22.92 mmol) was added dropwise. After stirring at 0° C. for 30 min, the reaction was quenched with sat. $NaHCO_3$. The reaction mixture was extracted with EtOAc. The organic layer was washed with water, brine and dried over $Na_2SO_4$. The organic layer was then concentrated and purified on silica gel (0-4% MeOH in $CH_2Cl_2$) to provide the desired product. LCMS calculated for $C_{20}H_{28}N_3O_4$ (M+H)$^+$: m/z=374.2; found 274.1.

Step 7. tert-butyl (2S,4S)-4-amino-2-(cyanomethyl)piperidine-1-carboxylate

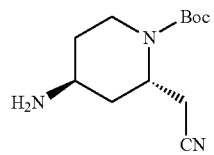

To a 250 mL round bottom flask was added tert-butyl (2S,4S)-4-(((benzyloxy)carbonyl)amino)-2-(cyanomethyl)

piperidine-1-carboxylate (5.76 g, 15.42 mmol) and Pd/C (0.820 g, 0.771 mmol). The flask was charged with nitrogen before MeOH (100 mL) was added. The reaction mixture was purged with hydrogen gas, and stirred for 30 min. After completion, the reaction was filtrated through a celite pad. The solvent was removed and the residue was used directly without further purification. LCMS calculated for $C_{12}H_{22}N_3O_2$ (M+H)$^+$: m/z=240.2; found 184.1.

Step 8. tert-butyl (2S,4S)-2-(cyanomethyl)-4-((2-(3-(dimethylamino)azetidin-1-yl)-8-methoxy-3-nitro-1,7-naphthyridin-4-yl)amino)piperidine-1-carboxylate

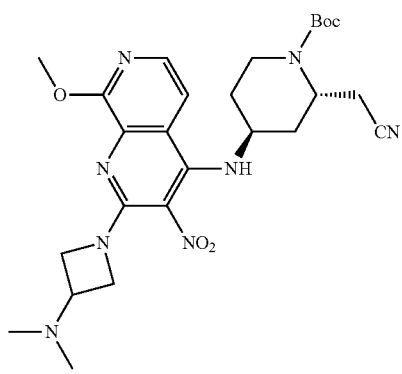 [SMILES: COc1nccc2c(N[C@H]3CCN(C(=O)OC(C)(C)C)[C@H](CC#N)C3)c([N+](=O)[O-])c(N3CC(N(C)C)C3)nc12]

To a DCM (100 mL) solution of 8-methoxy-3-nitro-1,7-naphthyridine-2,4-diol (1 g, 4.22 mmol) was added DIPEA (2.21 ml, 12.65 mmol) at −78° C. followed by adding triflate anhydride (1 mol DCM solution, 12.65 ml, 12.65 mmol). The mixture was warmed to 0° C., and stirred for 30 min before cooled to −78° C. again. A DCM solution of DIPEA (1.473 ml, 8.43 mmol), and tert-butyl (2S,4S)-4-amino-2-(cyanomethyl)piperidine-1-carboxylate (2.018 g, 8.43 mmol) was then added to the reaction mixture through syringe at −78° C. dropwise. The resulting solution was stirred for 30 min at −78° C. before N,N-dimethylazetidin-3-amine, 2HCl salt (1.095 g, 6.32 mmol) and DIPEA (2.95 ml, 16.87 mmol) were added. The reaction was then warmed to rt and stirred for another 30 min before quenched with sat. NaHCO$_3$ solution. The reaction mixture was extracted with DCM. The organic layer was washed with water, brine and dried over Na$_2$SO$_4$. The organic layer was then concentrated and purified on silica gel (0-10% MeOH in CH$_2$Cl$_2$) to provide the desired product. LCMS calculated for $C_{26}H_{37}N_8O_5$ (M+H)$^+$: m/z=541.3; found 541.2.

Step 9. tert-butyl (2S,4S)-2-(cyanomethyl)-4-(4-(3-(dimethylamino)azetidin-1-yl)-6-methoxy-1H-imidazo[4,5-c][1,7]naphthyridin-1-yl)piperidine-1-carboxylate

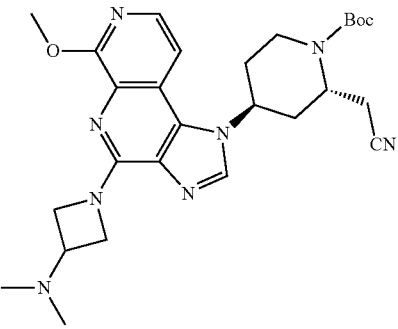 [SMILES: COc1nccc2c1nc(N1CC(N(C)C)C1)c1ncn([C@H]3CCN(C(=O)OC(C)(C)C)[C@H](CC#N)C3)c12]

To a 100 mL round bottom flask was added tert-butyl (2S,4S)-2-(cyanomethyl)-4-((2-(3-(dimethylamino)azetidin-1-yl)-8-methoxy-3-nitro-1,7-naphthyridin-4-yl)amino) piperidine-1-carboxylate (500 mg, 0.925 mmol) and Pd/C (98 mg, 0.093 mmol). The flask was charged with nitrogen before MeOH (20 mL) was added. The reaction mixture was purged with hydrogen gas, and stirred for 2 h. After completion, the reaction was filtrated through a celite pad. The solvent was removed and the residue was added toluene (2 mL), triethyl orthoformate (770 μl, 4.62 mmol), and acetic acid (106 μl, 1.850 mmol). The mixture was heated to 100° C. for 3 h till the starting material is consumed. The solvent was then removed, the residue was dissolved in DCM and washed 1N NaOH solution, brine and dried over Na$_2$SO$_4$. The organic layer was then concentrated and purified on silica gel (0-10% MeOH in CH$_2$Cl$_2$) to provide the desired product. LCMS calculated for $C_{27}H_{37}N_8O_3$ (M+H)$^+$: m/z=521.3; found 521.1.

Step 10. tert-butyl (2S,4S)-2-(cyanomethyl)-4-(4-(3-(dimethylamino)azetidin-1-yl)-6-hydroxy-1H-imidazo[4,5-c][1,7]naphthyridin-1-yl)piperidine-1-carboxylate

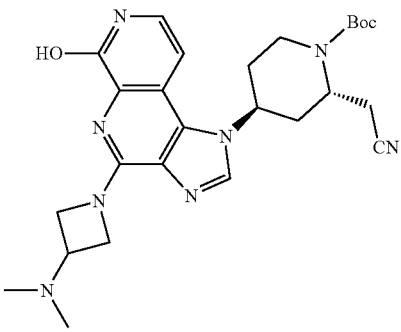 [SMILES: CN(C)C1CN(c2nc3c(O)nccc3c3c2ncn3[C@H]2CCN(C(=O)OC(C)(C)C)[C@H](CC#N)C2)C1]

To a EtOH (4 mL) solution of tert-butyl (2S,4S)-2-(cyanomethyl)-4-(4-(3-(dimethylamino)azetidin-1-yl)-6-methoxy-1H-imidazo[4,5-c][1,7]naphthyridin-1-yl)piperidine-1-carboxylate (600 mg, 1.152 mmol) was added 2 mL of 40% HBr solution. The reaction was heated to 80° C. for 30 min. The reaction was then neutralized with 4N NaOH solution. Sodium bicarbonate (290 mg, 3.46 mmol) and di-tert-butyl dicarbonate (377 mg, 1.729 mmol) and 4 mL of MeOH were added to the reaction. After stirring for 4 h, the reaction was extracted with DCM and the organic layer was washed with water, brine and dried over $Na_2SO_4$. The organic layer was then concentrated and purified on silica gel (0-30% MeOH in $CH_2Cl_2$) to provide the desired product. LCMS calculated for $C_{26}H_{35}N_8O_3$ (M+H)$^+$: m/z=507.3; found 507.1.

Step 11. tert-butyl (2S,4S)-2-(cyanomethyl)-4-(4-(3-(dimethylamino)azetidin-1-yl)-7-(3-(methoxymethoxy)naphthalen-1-yl)-6-oxo-6,7-dihydro-1H-imidazo[4,5-c][1,7]naphthyridin-1-yl)piperidine-1-carboxylate

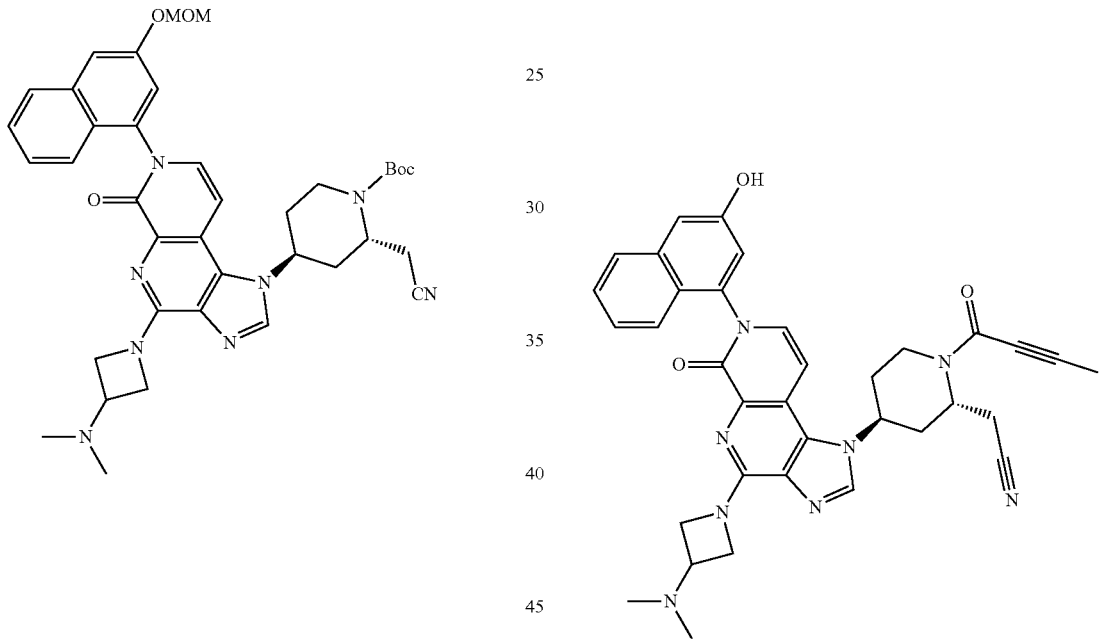

To a DCM (2 mL) solution of tert-butyl (2S,4S)-2-(cyanomethyl)-4-(4-(3-(dimethylamino)azetidin-1-yl)-6-hydroxy-1H-imidazo[4,5-c][1,7]naphthyridin-1-yl)piperidine-1-carboxylate (40 mg, 0.079 mmol) was added (3-(methoxymethoxy)naphthalen-1-yl)boronic acid (55.0 mg, 0.237 mmol), copper(II) trifluoromethanesulfonate (2.86 mg, 7.90 μmol), TMEDA (35.7 μl, 0.237 mmol), and DIEA (69.0 μl, 0.395 mmol). The reaction was stirred under air overnight before quenched with water. The mixture was then extracted with DCM, and the organic layer was washed with water, brine and dried over $Na_2SO_4$. The organic layer was then concentrated and purified on silica gel (0-7% MeOH in $CH_2Cl_2$) to provide the desired product. LCMS calculated for $C_{38}H_{45}N_8O_5$ (M+H)$^+$: m/z=693.3; found 693.3.

Step 12. 2-((2S,4S)-1-acryloyl-4-(4-(3-(dimethylamino)azetidin-1-yl)-7-(3-hydroxynaphthalen-1-yl)-6-oxo-6,7-dihydro-1H-imidazo[4,5-c][1,7]naphthyridin-1-yl)piperidin-2-yl)acetonitrile To a DCM (1 mL) solution of tert-butyl (2S,4S)-2-(cyanomethyl)-4-(4-(3-(dimethylamino)azetidin-1-yl)-7-(3-(methoxymethoxy)naphthalen-1-yl)-6-oxo-6,7-dihydro-1H-imidazo[4,5-c][1,7]naphthyridin-1-yl)piperidine-1-carboxylate (20 mg, 0.029 mmol) was added 1 mL of TFA. The reaction was stirred for 1 h before the solvent was removed under vacuum. The residue was dissolved in DCM again, DIPEA (7.56 μl, 0.043 mmol) and acryloyl chloride (3.92 mg, 0.043 mmol) were added sequentially at 0° C. After stirring for 10 min, the reaction was quenched by adding TFA. The mixture was diluted with acetonitrile/water and purified using prep-LCMS (XBridge C18 column, eluting with a gradient of acetonitrile/water containing 0.1% TFA, at flow rate of 60 mL/min) to afford the desired products as TFA salt. LCMS calculated for $C_{34}H_{35}N_8O_3$ (M+H)$^+$: m/z=603.3; found 603.3.

Example 2. 2-((2S,4S)-1-(but-2-ynoyl)-4-(4-(3-(dimethylamino)azetidin-1-yl)-7-(3-hydroxynaphthalen-1-yl)-6-oxo-6,7-dihydro-1H-imidazo[4,5-c][1,7]naphthyridin-1-yl)piperidin-2-yl)acetonitrile 2-((2S,4S)-4-(4-(3-(dimethylamino)azetidin-1-yl)-7-(3-hydroxynaphthalen-1-yl)-6-oxo-6,7-dihydro-1H-imidazo[4,5-c][1,7]naphthyridin-1-yl)piperidin-2-yl)acetonitrile (Example 1, step 12, 15.84 mg, 0.029 mmol) was dissolved in THF (0.5 mL), but-2-ynoic acid (2.427 mg, 0.029 mmol), HATU (16.46 mg, 0.043 mmol), and DIEA (7.56 μl, 0.043 mmol) were added sequentially. The reaction was stirred for 4 h before quenched by adding water. The mixture was diluted with acetonitrile/water and purified using prep-LCMS (XBridge C18 column, eluting with a gradient of acetonitrile/water containing 0.1% TFA, at flow rate of 60 mL/min) to afford the desired products as TFA salt. LCMS calculated for $C_{35}H_{35}N_8O_3$ (M+H)$^+$: m/z=615.3; found 615.3.

Example 3. 1-((1R,4R,5S)-2-azabicyclo[2.1.1]hexan-5-yl)-4-(3-(dimethylamino)azetidin-1-yl)-7-(3-hydroxynaphthalen-1-yl)-2-(2-(methylamino)ethyl)-1,7-dihydro-6H-imidazo[4,5-c][1,7]naphthyridin-6-one

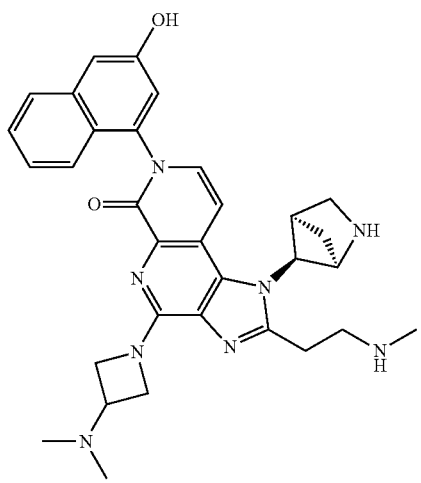 [SMILES: CNCCc1nc2c(N3CC(N(C)C)C3)nc3c(=O)n(-c4cc(O)cc5ccccc45)ccc3c2n1[C@H]1[C@H]2CN[C@@H]1C2]

Step 1. tert-butyl 5-((2-(3-(dimethylamino)azetidin-1-yl)-8-methoxy-3-nitro-1,7-naphthyridin-4-yl)amino)-2-azabicyclo[2.1.1]hexane-2-carboxylate

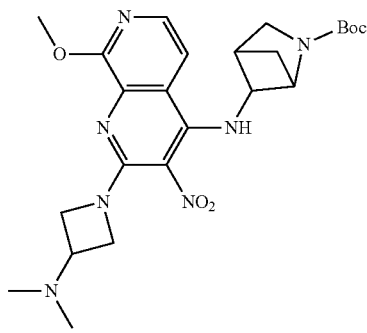 [SMILES: COc1nccc2c(NC3C4CC3N(C(=O)OC(C)(C)C)C4)c([N+](=O)[O-])c(N3CC(N(C)C)C3)nc12]

This compound was prepared according to the procedure described in Example 1, step 8 replacing tert-butyl (2S,4S)-4-amino-2-(cyanomethyl)piperidine-1-carboxylate with tert-butyl 5-amino-2-azabicyclo[2.1.1]hexane-2-carboxylate. The product was purified on silica gel (0-10% MeOH in CH$_2$Cl$_2$) to provide the desired product. LCMS calculated for C$_{24}$H$_{34}$N$_7$O$_5$ (M+H)$^+$ m/z=500.3; found 500.3.

Step 2. tert-butyl 5-(2-(2-((tert-butoxycarbonyl)(methyl)amino)ethyl)-4-(3-(dimethylamino)azetidin-1-yl)-6-methoxy-1H-imidazo[4,5-c][1,7]naphthyridin-1-yl)-2-azabicyclo[2.1.1]hexane-2-carboxylate

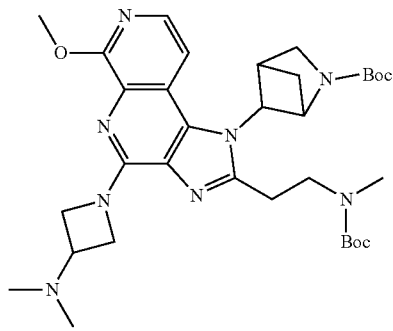

To a 100 mL round bottom flask was added tert-butyl 5-((2-(3-(dimethylamino)azetidin-1-yl)-8-methoxy-3-nitro-1,7-naphthyridin-4-yl)amino)-2-azabicyclo[2.1.1]hexane-2-carboxylate (1.958 g, 3.92 mmol) and Pd/C (420 mg, 0.39 mmol). The flask was charged with nitrogen before MeOH (20 mL) was added. The reaction mixture was purged with hydrogen gas, and stirred for 2 h. After completion, the reaction was filtrated through a celite pad. The solvent was removed and the residue was added EtOH (10 mL), tert-butyl methyl(3-oxopropyl)carbamate (0.909 g, 4.86 mmol), and acetic acid (0.347 ml, 6.07 mmol). The mixture was heated to 80° C. for 3 h till the starting material is consumed. The solvent was then removed, the residue was dissolved in DCM and washed 1N NaOH solution, brine and dried over Na$_2$SO$_4$. The organic layer was then concentrated and purified on silica gel (0-10% MeOH in CH$_2$Cl$_2$) to provide the desired product. LCMS calculated for C$_{33}$H$_{49}$N$_8$O$_5$ (M+H)$^+$: m/z=637.4 found 637.4.

Step 3. tert-butyl 5-(2-(2-((tert-butoxycarbonyl)(methyl)amino)ethyl)-4-(3-(dimethylamino)azetidin-1-yl)-6-hydroxy-1H-imidazo[4,5-c][1,7]naphthyridin-1-yl)-2-azabicyclo[2.1.1]hexane-2-carboxylate

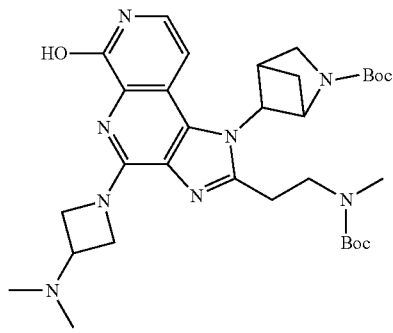

To a EtOH (4 mL) solution of tert-butyl 5-(2-(2-((tert-butoxycarbonyl)(methyl)amino)ethyl)-4-(3-(dimethylamino)azetidin-1-yl)-6-methoxy-1H-imidazo[4,5-c][1,7]naphthyridin-1-yl)-2-azabicyclo[2.1.1]hexane-2-carboxylate (360 mg, 0.565 mmol) was added 2 mL of 40% HBr solution. The reaction was heated to 80° C. for 30 min.

The reaction was then neutralized with 4N NaOH solution. Sodium bicarbonate (237 mg, 2.83 mmol) and di-tert-butyl dicarbonate (308 mg, 1.4 mmol) and 4 mL of MeOH were added to the reaction. After stirring for 4 h, the reaction was extracted with DCM and the organic layer was washed with water, brine and dried over $Na_2SO_4$. The organic layer was then concentrated and purified on silica gel (0-30% MeOH in $CH_2Cl_2$) to provide the desired product. LCMS calculated for $C_{32}H_{47}N_8O_5$ (M+H)$^+$: m/z=623.4; found 623.4.

Step 4. tert-butyl 5-(2-(2-((tert-butoxycarbonyl)(methyl)amino)ethyl)-4-(3-(dimethylamino)azetidin-1-yl)-7-(3-(methoxymethoxy)naphthalen-1-yl)-6-oxo-6,7-dihydro-1H-imidazo[4,5-c][1,7]naphthyridin-1-yl)-2-azabicyclo[2.1.1]hexane-2-carboxylate

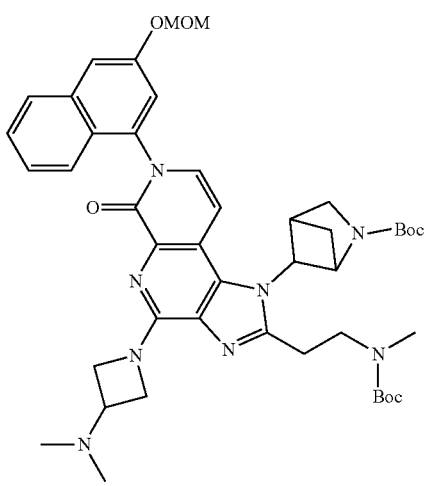

To a DCM (2 mL) solution of tert-butyl 5-(2-(2-((tert-butoxycarbonyl)(methyl)amino)ethyl)-4-(3-(dimethylamino)azetidin-1-yl)-6-hydroxy-1H-imidazo[4,5-c][1,7]naphthyridin-1-yl)-2-azabicyclo[2.1.1]hexane-2-carboxylate (80 mg, 0.128 mmol) was added (3-(methoxymethoxy)naphthalen-1-yl)boronic acid (89 mg, 0.38 mmol), copper(II) trifluoromethanesulfonate (4.6 mg, 12.8 μmol), TMEDA (57.8 μl, 0.38 mmol), and DIPEA (112 μl, 0.63 mmol). The reaction was stirred under air overnight before quenched with water. The mixture was then extracted with DCM, and the organic layer was washed with water, brine and dried over $Na_2SO_4$. The organic layer was then concentrated and purified on silica gel (0-7% MeOH in $CH_2Cl_2$) to provide the desired product. LCMS calculated for $C_{44}H_{57}N_8O_7$(M+H)$^+$: m/z=809.4; found 809.4.

Step 5. 1-((1R,4R,5S)-2-azabicyclo[2.1.1]hexan-5-yl)-4-(3-(dimethylamino)azetidin-1-yl)-7-(3-hydroxynaphthalen-1-yl)-2-(2-(methylamino)ethyl)-1,7-dihydro-6H-imidazo[4,5-c][1,7]naphthyridin-6-one To a DCM (1 mL) solution of tert-butyl 5-(2-(2-((tert-butoxycarbonyl)(methyl)amino)ethyl)-4-(3-(dimethylamino)azetidin-1-yl)-7-(3-(methoxymethoxy)naphthalen-1-yl)-6-oxo-6,7-dihydro-1H-imidazo[4,5-c][1,7]naphthyridin-1-yl)-2-azabicyclo[2.1.1]hexane-2-carboxylate (20 mg, 0.025 mmol) was added 1 mL of TFA. The reaction was stirred for 1 h before the solvent was removed under vacuum. The mixture was diluted with acetonitrile/water and purified using prep-LCMS (XBridge C18 column, eluting with a gradient of acetonitrile/water containing 0.1% TFA, at flow rate of 60 mL/min) to afford the desired products as a racemic TFA salt. LCMS calculated for $C_{32}H_{37}N_8O_2$ (M+H)$^+$: m/z=565.3; found 565.3.

Example 4. 2-((2S,4S)-1-acryloyl-4-(4-(3-(dimethylamino)azetidin-1-yl)-7-(naphthalen-1-yl)-6,7,8,9-tetrahydro-1H-imidazo[4,5-c][1,7]naphthyridin-1-yl)piperidin-2-yl)acetonitrile

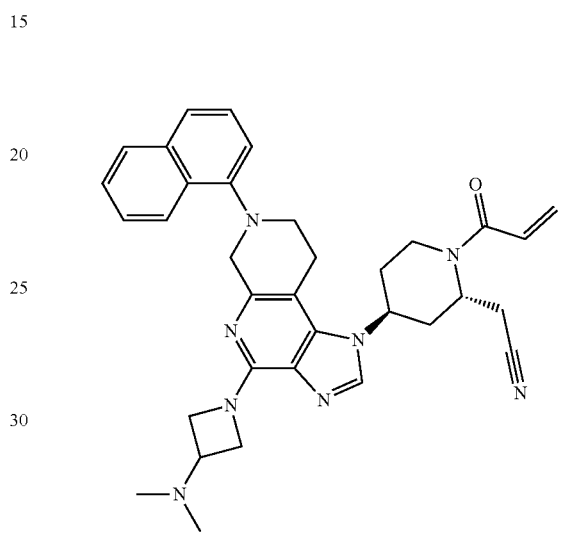

Step 1. 1-(tert-butyl) 4-ethyl 3-iminopiperidine-1,4-dicarboxylate

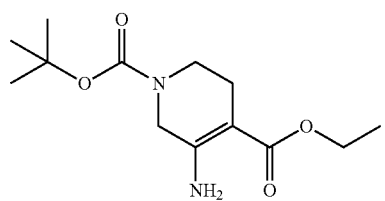 [SMILES: CCOC(=O)C1=C(N)CN(C(=O)OC(C)(C)C)CC1]

To a solution of 1-(tert-butyl) 4-ethyl 3-oxopiperidine-1,4-dicarboxylate (50 g, 184 mmol) was added ammonium in EtOH (100 mL, 2M solution). The reaction mixture was heated to 60° C. for 3 h. The solvent was evaporated under reduced pressure to afford a yellow solid (47 g). LCMS calculated for $C_{13}H_{23}N_2O_4$ (M+H)$^+$: m/z=271.2; found 271.2.

Step 2. 1-(tert-butyl) 4-ethyl 5-(3-methoxy-3-oxo-propanamido)-3,6-dihydropyridine-1,4(2H)-dicarboxylate

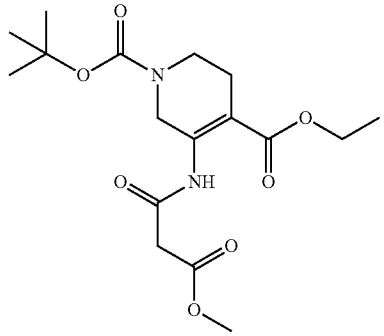 [SMILES: CCOC(=O)C1=C(NC(=O)CC(=O)OC)CN(C(=O)OC(C)(C)C)CC1]

To a stirred solution of 1-(tert-butyl) 4-ethyl 5-amino-3,6-dihydropyridine-1,4(2H)-dicarboxylate (45 g, 166 mmol) in dichloromethane (300 mL) was added TEA (25.5 ml, 183 mmol), followed by methyl malonyl chloride methyl (20.42 ml, 191 mmol) portionwise at 0° C. under $N_2$ atmosphere. The reaction mixture was stirred for further 12 h at rt, then diluted with 250 mL dichloromethane. The organic solution was washed with water and brine, dried over $Na_2SO_4$. The solvent was then removed to give the title compound as a yellow solid. The material was used without further purification in the next step. LCMS calculated for $C_{17}H_{27}N_2O_7$ $(M+H)^+$: m/z=371.2; found 371.2.

Step 3. 7-(tert-butyl) 3-methyl 4-hydroxy-2-oxo-2,5,6,8-tetrahydro-1,7-naphthyridine-3,7(1H)-dicarboxylate

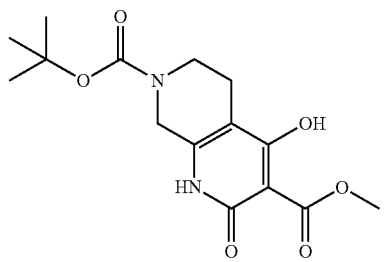 [SMILES: COC(=O)c1c(O)c2c([nH]c1=O)CN(C(=O)OC(C)(C)C)CC2]

To a stirred solution of 1-(tert-butyl) 4-ethyl 5-(3-methoxy-3-oxopropanamido)-3,6-dihydropyridine-1,4(2H)-dicarboxylate (68.2 g, 184 mmol) in anhydrous MeOH (200 mL) was added sodium methoxide (126 ml, 552 mmol) under $N_2$ atmosphere, and the resulting mixture was refluxed for 3 h. The mixture was cooled and the insoluble salt was filtered and dissolved in 500 mL water. The aqueous solution was adjusted to pH 2 with 1 N HCl and extracted with EtOAc. The organic phase was combined, dried over $Na_2SO_4$, and concentrated. The crude material was recrystallized from isopropanol to afford the title compound as an off white solid. LCMS calculated for $C_{15}H_{21}N_2O_6$ $(M+H)^+$: m/z=325.1; found 325.2.

Step 4. 4-hydroxy-5,6,7,8-tetrahydro-1,7-naphthyridin-2(1H)-one

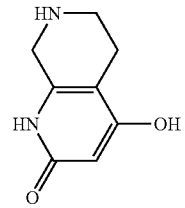

To a 500 mL round bottom flask charged with 7-(tert-butyl) 3-methyl 4-hydroxy-2-oxo-2,5,6,8-tetrahydro-1,7-naphthyridine-3,7(1H)-dicarboxylate (21 g, 64.7 mmol) was added 100 mL of concentrated HCl solution. The reaction mixture was stirred for 3 h at 100° C. The solvent was removed under vacuum. The resulting solid was collected and washed with acetone to afford the desired product as HCl salt. LCMS calculated for $C_8H_{11}N_2O_2$ $(M+H)^+$: m/z=167.1; found 167.1.

Step 5. benzyl 4-hydroxy-3-nitro-2-oxo-2,5,6,8-tetrahydro-1,7-naphthyridine-7(1H)-carboxylate

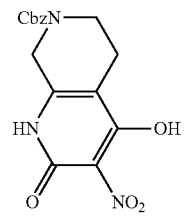

To 4-hydroxy-5,6,7,8-tetrahydro-1,7-naphthyridin-2(1H)-one hydrochloride (10 g, 49.3 mmol) in a vial was added 5 mL conc. $H_2SO_4$ (caution: gas evolution, HCl), and $KNO_3$ (5.0 g, 50 mmol) at rt. After stirring at 50° C. for 1 h, the reaction was cooled to 0° C. and neutralized with 4N NaOH solution. $NaHCO_3$ (10.36 g, 123 mmol), benzyl (2,5-dioxopyrrolidin-1-yl) carbonate (24.60 g, 99 mmol), and THF (200 mL) were added to the reaction, the reaction were stirred vigorously overnight. The reaction was quenched by 1N HCl to pH 4 before extracted with 3:1 DCM:IPA, the organic phase was combined, dried over $Na_2SO_4$, and concentrated. The crude material was recrystallized from isopropanol to afford the title compound as a yellow solid. LCMS calculated for $C_{16}H_{16}N_3O_6$ $(M+H)^+$: m/z=346.1; found 346.2.

Step 6. benzyl 4-(((2S,4S)-1-(tert-butoxycarbonyl)-2-(cyanomethyl)piperidin-4-yl)amino)-2-(3-(dimethylamino)azetidin-1-yl)-3-nitro-5,8-dihydro-1,7-naphthyridine-7(6H)-carboxylate

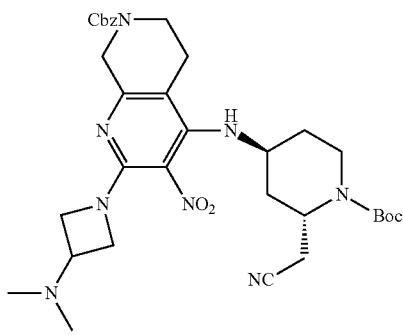 [SMILES: CN(C)C1CN(c2nc3c(c(N[C@H]4CCN(C(=O)OC(C)(C)C)[C@H](CC#N)C4)c2[N+](=O)[O-])CCN(C(=O)OCc2ccccc2)C3)C1]

To a DCM (100 mL) solution of benzyl 2,4-dihydroxy-3-nitro-5,8-dihydro-1,7-naphthyridine-7(6H)-carboxylate (1 g, 2.90 mmol) was added DIPEA (1.113 ml, 6.37 mmol) at −78° C. followed by adding triflate anhydride (1 mol DCM solution, 6.37 ml, 6.37 mmol). The mixture was warmed to 0° C., and stirred for 30 min before cooled to −78° C. again. A DCM solution of DIPEA (1.113 ml, 6.37 mmol), and tert-butyl (2S,4S)-4-amino-2-(cyanomethyl)piperidine-1-carboxylate (0.693 g, 2.90 mmol) was then added to the reaction mixture through syringe at −78° C. dropwise. The resulting solution was stirred for 30 min at −78° C. before N,N-dimethylazetidin-3-amine, 2HCl (0.752 g, 4.34 mmol) and DIPEA (1.517 ml, 8.69 mmol) were added. The reaction was then warmed to rt and stirred for another 30 min before quenched with sat. NaHCO$_3$ solution. The reaction mixture was extracted with DCM. The organic layer was washed with water, brine and dried over Na$_2$SO$_4$. The organic layer was then concentrated and purified on silica gel (0-10% MeOH in CH$_2$Cl$_2$) to provide the desired product. LCMS calculated for C$_{33}$H$_{45}$N$_8$O$_6$ (M+H)$^+$: m/z=649.3; found 649.3.

Step 7. benzyl 1-((2S,4S)-1-(tert-butoxycarbonyl)-2-(cyanomethyl)piperidin-4-yl)-4-(3-(dimethylamino)azetidin-1-yl)-1,6,8,9-tetrahydro-7H-imidazo[4,5-c][1,7]naphthyridine-7-carboxylate

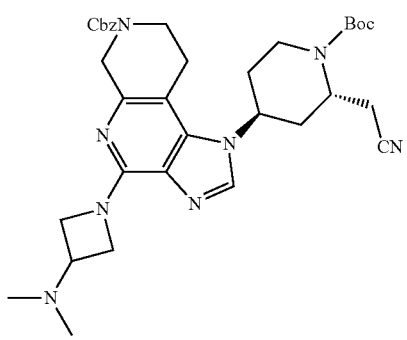 [SMILES: CN(C)C1CN(c2nc3c(c4c2ncn4[C@H]2CCN(C(=O)OC(C)(C)C)[C@H](CC#N)C2)CCN(C(=O)OCc2ccccc2)C3)C1]

To a MeOH (30 mL) solution of benzyl 4-(((2S,4S)-1-(tert-butoxycarbonyl)-2-(cyanomethyl)piperidin-4-yl)amino)-2-(3-(dimethylamino)azetidin-1-yl)-3-nitro-5,8-dihydro-1,7-naphthyridine-7(6H)-carboxylate (1.879 g, 2.90 mmol) was added water solution of Na$_2$S$_2$O$_4$ (2.017 g, 11.58 mmol) in one portion. The reaction was stirred for 20 min before diluted with water and extracted with DCM. The organic layer was washed with water, brine and dried over Na$_2$SO$_4$. The organic layer was then concentrated and dissolved in toluene (5 mL), triethyl orthoformate (1.54 mL, 9.24 mmol), and acetic acid (212 µl, 3.70 mmol). The mixture was heated to 100° C. for 3 h till the starting material is consumed. The solvent was then removed, the residue was dissolved in DCM and washed 1N NaOH solution, brine and dried over Na$_2$SO$_4$. The organic layer was then concentrated and purified on silica gel (0-10% MeOH in CH$_2$Cl$_2$) to provide the desired product. LCMS calculated for C$_{34}$H$_{45}$N$_8$O$_4$ (M+H)$^+$: m/z=629.4; found 629.4.

Step 8. tert-butyl (2S,4S)-2-(cyanomethyl)-4-(4-(3-(dimethylamino)azetidin-1-yl)-6,7,8,9-tetrahydro-1H-imidazo[4,5-c][1,7]naphthyridin-1-yl)piperidine-1-carboxylate

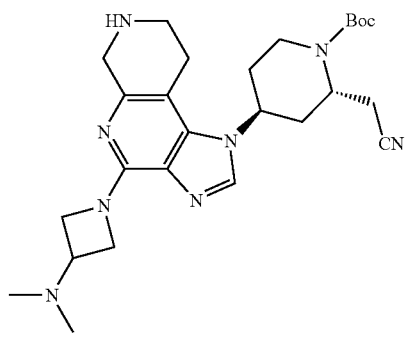 [SMILES: CN(C)C1CN(c2nc3c(c4c2ncn4[C@H]2CCN(C(=O)OC(C)(C)C)[C@H](CC#N)C2)CCNC3)C1]

To a 100 mL round bottom flask was added benzyl 1-((2S,4S)-1-(tert-butoxycarbonyl)-2-(cyanomethyl)piperidin-4-yl)-4-(3-(dimethylamino)azetidin-1-yl)-1,6,8,9-tetrahydro-7H-imidazo[4,5-c][1,7]naphthyridine-7-carboxylate (240 mg, 0.382 mmol) and Pd/C (40.6 mg, 0.038 mmol). The flask was charged with nitrogen before MeOH (20 mL) was added. The reaction mixture was purged with hydrogen gas, and stirred for 2 h. After completion, the reaction was filtrated through a celite pad. The solvent was removed and the residue was used directly in next step without further purification. LCMS calculated for C$_{26}$H$_{39}$N$_8$O$_2$ (M+H)$^+$: m/z=495.3; found 495.2.

Step 9. tert-butyl (2S,4S)-2-(cyanomethyl)-4-(4-(3-(dimethylamino)azetidin-1-yl)-7-(naphthalen-1-yl)-6,7,8,9-tetrahydro-1H-imidazo[4,5-c][1,7]naphthyridin-1-yl)piperidine-1-carboxylate

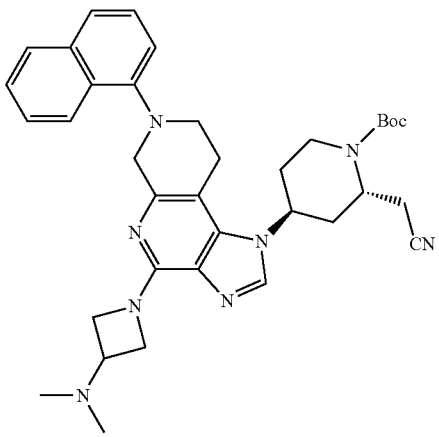 [SMILES: CN(C)C1CN(c2nc3c(c4c2ncn4[C@H]2CCN(C(=O)OC(C)(C)C)[C@H](CC#N)C2)CCN(c2cccc4ccccc24)C3)C1]

To a dioxane (2 mL) solution of tert-butyl (2S,4S)-2-(cyanomethyl)-4-(4-(3-(dimethylamino)azetidin-1-yl)-6,7,8,9-tetrahydro-1H-imidazo[4,5-c][1,7]naphthyridin-1-yl)piperidine-1-carboxylate (40 mg, 0.081 mmol) was added 1-bromonaphthalene (33.5 mg, 0.162 mmol), RuPhos Pd G2 (6.28 mg, 8.09 μmol) and $Cs_2CO_3$ (52.7 mg, 0.162 mmol). The reaction was stirred for 12 h, after completion, the reaction was filtrated through a celite pad. The solvent was removed and the residue was used directly in next step without further purification. LCMS calculated for $C_{36}H_{45}N_8O_2$ $(M+H)^+$: m/z=621.4; found 621.4.

Step 10. 2-((2S,4S)-1-acryloyl-4-(4-(3-(dimethylamino)azetidin-1-yl)-7-(naphthalen-1-yl)-6,7,8,9-tetrahydro-1H-imidazo[4,5-c][1,7]naphthyridin-1-yl)piperidin-2-yl)acetonitrile To a DCM (1 mL) solution of tert-butyl (2S,4S)-2-(cyanomethyl)-4-(4-(3-(dimethylamino)azetidin-1-yl)-7-(naphthalen-1-yl)-6-oxo-6,7-dihydro-1H-imidazo[4,5-c][1,7]naphthyridin-1-yl)piperidine-1-carboxylate (20 mg, 0.032 mmol) was added 1 mL of TFA. The reaction was stirred for 1 h before the solvent was removed under vacuum. The residue was dissolved in DCM again, DIEA (8.28 μl, 0.047 mmol) and acryloyl chloride (4.29 mg, 0.047 mmol) were added sequentially at 0° C. After stirring for 10 min, the reaction was quenched by adding TFA. The mixture was diluted with acetonitrile/water and purified using prep-LCMS (XBridge C18 column, eluting with a gradient of acetonitrile/water containing 0.1% TFA, at flow rate of 60 mL/min) to afford the desired products as TFA salt. LCMS calculated for $C_{34}H_{39}N_8O$ $(M+H)^+$: m/z=575.3; found 575.3.

Example 5. 2-((2S,4S)-1-acryloyl-4-(4-(3-(dimethylamino)azetidin-1-yl)-7-(3-hydroxynaphthalen-1-yl)-6,7,8,9-tetrahydro-1H-imidazo[4,5-c][1,7]naphthyridin-1-yl)piperidin-2-yl)acetonitrile

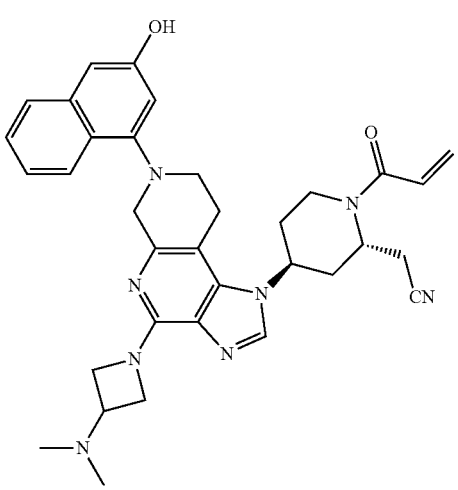 [SMILES: C=CC(=O)N1CC[C@H](n2cnc3c(N4CC(N(C)C)C4)nc4c(c32)CCN(c2cc(O)cc3ccccc23)C4)C[C@H]1CC#N]

This compound was prepared according to the procedure described in Example 4, in step 9 replacing 1-bromonaphthalene with 1-bromo-3-(methoxymethoxy)naphthalene. The final product was purified with acetonitrile/water and purified using prep-LCMS (XBridge C18 column, eluting with a gradient of acetonitrile/water containing 0.1% TFA, at flow rate of 60 mL/min) to afford the desired products as TFA salt. LCMS calculated for $C_{34}H_{39}N_8O_2$ $(M+H)^+$: m/z=591.3; found 591.3.

Example 6. 2-((2S,4S)-1-acryloyl-4-(4-(3-(dimethylamino)azetidin-1-yl)-7-(naphthalen-1-yl)-6-oxo-8-(trifluoromethyl)-6,7-dihydro-1H-imidazo[4,5-c][1,7]naphthyridin-1-yl)piperidin-2-yl)acetonitrile

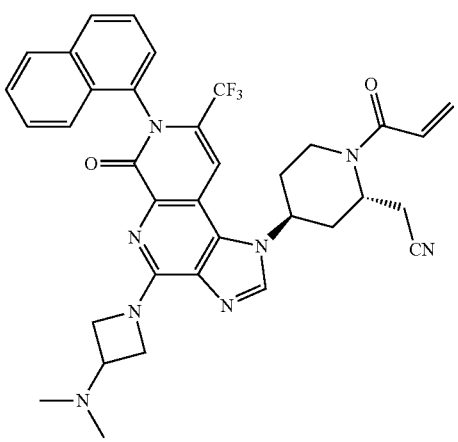 [SMILES: C=CC(=O)N1CC[C@H](n2cnc3c(N4CC(N(C)C)C4)nc4c(=O)n(-c5cccc6ccccc56)c(C(F)(F)F)cc4c32)C[C@H]1CC#N]

Step 1. methyl 3-(naphthalen-1-ylamino)-3-oxopropanoate

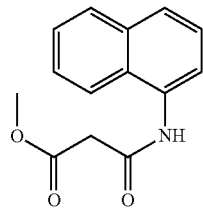 [SMILES: COC(=O)CC(=O)Nc1cccc2ccccc12]

To a DCM (500 mL) solution of naphthalen-1-amine (45 g, 314 mmol) was added TEA (52.6 ml, 377 mmol) and methyl 3-chloro-3-oxopropanoate (47.2 g, 346 mmol) sequentially at 0° C. The reaction was stirred for 30 min before quenched with 2% HCl solution. The mixture was then extracted with DCM, and the organic layer was washed with water, brine and dried over $Na_2SO_4$. The organic layer was then concentrated and used directly in next step without further purification. LCMS calculated for $C_{14}H_{14}NO_3$ $(M+H)^+$: m/z=244.1; found 244.1.

Step 2. methyl 6,6,6-trifluoro-3-hydroxy-2-(naphthalen-1-ylcarbamoyl)-5-oxohexanoate

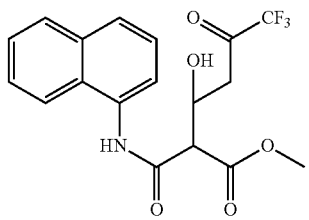 [SMILES: COC(=O)C(C(=O)Nc1cccc2ccccc12)C(O)CC(=O)C(F)(F)F]

To a dry THF (500 mL) solution of methyl 3-(naphthalen-1-ylamino)-3-oxopropanoate (76 g, 314 mmol) was added (E)-1,1,1-trifluoro-4-methoxybut-3-en-2-one (48.4 g, 314 mmol) and DBU (52.1 ml, 345 mmol) at 0° C. After addition, reaction was warmed to rt and stirred for 2 h before quenched with 2% HCl. The mixture was then extracted with DCM, and the organic layer was washed with water, brine and dried over $Na_2SO_4$. The organic layer was then concentrated and used directly in next step without further purification. LCMS calculated for $C_{18}H_{17}F_3NO_5$ $(M+H)^+$: m/z=384.1; found 384.1.

Step 3. 1-(naphthalen-1-yl)-2-oxo-6-(trifluoromethyl)-1,2-dihydropyridine-3-carboxylic acid

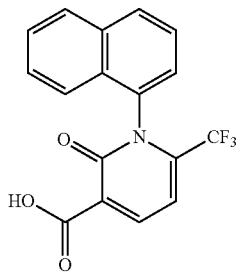 [SMILES: O=C(O)c1ccc(C(F)(F)F)n(-c2cccc3ccccc23)c1=O]

To a dry toluene (500 mL) solution of methyl 6,6,6-trifluoro-3-hydroxy-2-(naphthalen-1-ylcarbamoyl)-5-oxohexanoate (50 g, 130 mmol) was added p-toluenesulfonic acid monohydrate (1.241 g, 6.52 mmol). The reaction was heated at 110° C. for 20 min. After completion, reaction diluted with EtOAc. The mixture was then washed with sat. $NaHCO_3$, brine and dried over $Na_2SO_4$. The organic layer was then concentrated to dryness, then dissolved in THF (200 mL). 4N NaOH (200 mL) was then added to the solution and the reaction was stirred for 1 h before neutralized with 4N HCl. The mixture was then extracted with EtOAc, and the organic layer was washed with water, brine and dried over $Na_2SO_4$. The organic layer was then concentrated and used directly in next step without further purification. LCMS calculated for $C_{17}H_{11}F_3NO_3$ $(M+H)^+$: m/z=334.1; found 334.1.

Step 4. tert-butyl (1-(naphthalen-1-yl)-2-oxo-6-(trifluoromethyl)-1,2-dihydropyridin-3-yl)carbamate

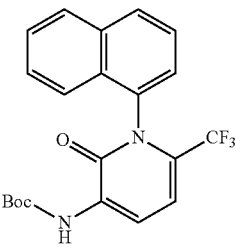

To a dry tert-butanol (300 mL) solution of 1-(naphthalen-1-yl)-2-oxo-6-(trifluoromethyl)-1,2-dihydropyridine-3-carboxylic acid (49 g, 147 mmol) was added diphenyl phosphorazidate (31.9 ml, 147 mmol) and TEA (26.6 ml, 191 mmol). The reaction mixture was heated at 75° C. for 12 h. The reaction was then cooled to rt, most of solvent was removed under vacuum. The resulting solid was filtrated, and washed with IPA to afford the title compound as light brown solid. LCMS calculated for $C_{21}H_{20}F_3N_2O_3$ $(M+H)^+$: m/z=405.1; found 405.1.

Step 5. 3-amino-4-iodo-1-(naphthalen-1-yl)-6-(trifluoromethyl)pyridin-2(1H)-one

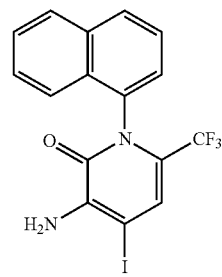 [SMILES: Nc1c(I)cc(C(F)(F)F)n(-c2cccc3ccccc23)c1=O]

In a 500 mL round bottom flask, tert-butyl (1-(naphthalen-1-yl)-2-oxo-6-(trifluoromethyl)-1,2-dihydropyridin-3-yl) carbamate (36.4 g, 90 mmol) was dissolved in DCM (100 mL) and TFA (100 mL). The mixture was stirred for 4 h before solvent was removed. The residue was taken in EtOAc and washed with sat. $NaHCO_3$. The organic layer was then concentrated to dryness and dissolved in 300 mL of MeCN, to this solution p-toluenesulfonic acid monohydrate (4.28 g, 22.50 mmol) and NIS (20.25 g, 90 mmol) were added at 0° C. The mixture was stirred for 20 min before quenched by diluting with water, then extracted with EtOAc. The organic layer was then concentrated and the residue was purified on silica gel to afford desired product as light brown solid. LCMS calculated for $C_{16}H_{11}F_3IN_2O$ $(M+H)^+$: m/z=431.0; found 431.1.

Step 6. methyl 3-amino-1-(naphthalen-1-yl)-2-oxo-6-(trifluoromethyl)-1,2-dihydropyridine-4-carboxylate

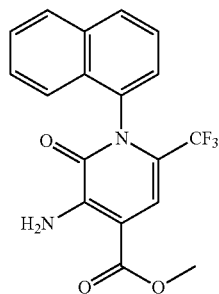 [SMILES: COC(=O)c1cc(C(F)(F)F)n(-c2cccc3ccccc23)c(=O)c1N]

To a 500 mL round bottom flask was added 3-amino-4-iodo-1-(naphthalen-1-yl)-6-(trifluoromethyl)pyridin-2(1H)-one (17 g, 39.5 mmol), bis(triphenylphosphine)palladium (II) chloride (2.77 g, 3.95 mmol), triethylamine (11.02 ml, 79 mmol), and MeOH (250 mL). The flask was purged with carbon monoxide gas, and stirred at 65° C. for 2 days. After completion, the solvent was removed, the residue was purified on silica gel (0-100% EtOAc in hexanes) to provide the desired product. LCMS calculated for $C_{18}H_{14}F_3N_2O_3$ $(M+H)^+$: m/z=363.1 found 363.1.

Step 7. methyl 3-(3-ethoxy-3-oxopropanamido)-1-(naphthalen-1-yl)-2-oxo-6-(trifluoromethyl)-1,2-dihydropyridine-4-carboxylate

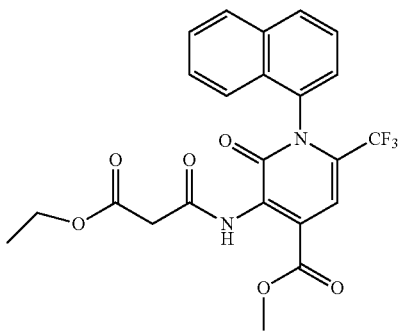 [SMILES: CCOC(=O)CC(=O)Nc1c(C(=O)OC)cc(C(F)(F)F)n(-c2cccc3ccccc23)c1=O]

To a vigorously stirred DCM (300 mL) solution of methyl 3-amino-1-(naphthalen-1-yl)-2-oxo-6-(trifluoromethyl)-1,2-dihydropyridine-4-carboxylate (8 g, 22.08 mmol) and pyridine (1.965 ml, 24.29 mmol) was added ethyl 3-chloro-3-oxopropanoate (3.11 ml, 24.29 mmol) in one portion at rt. The reaction was stirred for 10 min before quenched with 2% HCl solution. The mixture was then extracted with DCM, and the organic layer was washed with water, brine and dried over $Na_2SO_4$. The organic layer was then concentrated and the residue was purified on silica gel (0-100% EtOAc in hexanes) to provide the desired product. LCMS calculated for $C_{23}H_{20}F_3N_2O_6$ $(M+H)^+$: m/z=477.1 found 477.1.

Step 8. ethyl 2,4-dihydroxy-7-(naphthalen-1-yl)-8-oxo-6-(trifluoromethyl)-7,8-dihydro-1,7-naphthyridine-3-carboxylate

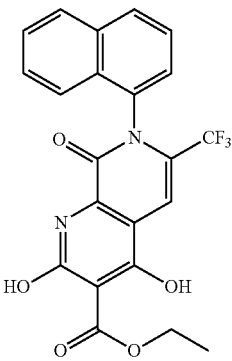 [SMILES: CCOC(=O)c1c(O)nc2c(=O)n(-c3cccc4ccccc34)c(C(F)(F)F)cc2c1O]

To an EtOH (200 mL) solution of methyl 3-(3-ethoxy-3-oxopropanamido)-1-(naphthalen-1-yl)-2-oxo-6-(trifluoromethyl)-1,2-dihydropyridine-4-carboxylate (15 g, 31.5 mmol) was added sodium ethoxide (20.41 g, 63.0 mmol, 21% wt) dropwise. After addition, the reaction was stirred at rt for 30 min, then concentrated and diluted with 50 mL of water. The mixture was then acidified with 1N HCl to pH=4. The precipitated product was collected and air dried overnight, and used in next reaction without further purification. LCMS calculated for $C_{22}H_{16}F_3N_2O_5$ $(M+H)^+$: m/z=445.1 found 445.1.

Step 9. 2,4-dihydroxy-7-(naphthalen-1-yl)-3-nitro-6-(trifluoromethyl)-1,7-naphthyridin-8(7H)-one

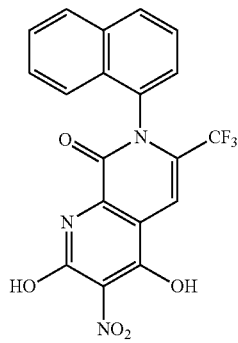 [SMILES: O=c1c2nc(O)c([N+](=O)[O-])c(O)c2cc(C(F)(F)F)n1-c1cccc2ccccc12]

Ethyl 2,4-dihydroxy-7-(naphthalen-1-yl)-8-oxo-6-(trifluoromethyl)-7,8-dihydro-1,7-naphthyridine-3-carboxylate (13.99 g, 31.5 mmol) was dissolved in TFA (50 mL) and concentrated HCl (50 mL). The mixture was heated at 100° C. overnight. The reaction was then diluted with water, the precipitated product was collected and air dried overnight. Acetic acid suspension of 2,4-dihydroxy-7-(naphthalen-1-yl)-6-(trifluoromethyl)-1,7-naphthyridin-8(7H)-one (500 mg, 1.343 mmol) was added fuming nitric acid (600 μl, 9.40 mmol) dropwise at 0° C. The reaction was then warmed to Step 10. tert-butyl (2S,4S)-2-(cyanomethyl)-4-((2-(3-(dimethylamino)azetidin-1-yl)-7-(naphthalen-1-yl)-3-nitro-8-oxo-6-(trifluoromethyl)-7,8-dihydro-1,7-naphthyridin-4-yl)amino)piperidine-1-carboxylate

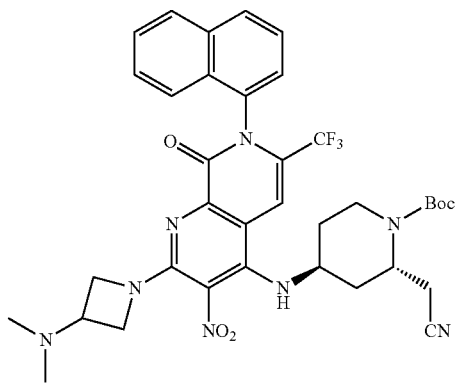 [SMILES: CN(C)C1CN(c2nc3c(=O)n(-c4cccc5ccccc45)c(C(F)(F)F)cc3c(N[C@H]3CCN(C(=O)OC(C)(C)C)[C@H](CC#N)C3)c2[N+](=O)[O-])C1]

To a DCM (100 mL) solution of 2,4-dihydroxy-7-(naphthalen-1-yl)-3-nitro-6-(trifluoromethyl)-1,7-naphthyridin-8(7H)-one (210 mg, 0.503 mmol) was added DIPEA (193 µl, 1.107 mmol) at −78° C. followed by adding triflate anhydride (1 M DCM solution, 1107 µl, 1.107 mmol). The mixture was warmed to 0° C., and stirred for 30 min before cooled to −78° C. again. A DCM solution of DIPEA (193 µl, 1.107 mmol), and tert-butyl (2S,4S)-4-amino-2-(cyanomethyl)piperidine-1-carboxylate (120 mg, 0.503 mmol) was then added to the reaction mixture through syringe at −78° C. dropwise. The resulting solution was stirred for 30 min at −78° C. before N,N-dimethylazetidin-3-amine, 2HCl (105 mg, 0.604 mmol) and DIPEA (400 µl, 2.2 mmol) were added. The reaction was then warmed to rt and stirred for another 30 min before quenched with sat. NaHCO₃ solution. The reaction mixture was extracted with DCM. The organic layer was washed with water, brine and dried over Na₂SO₄. The organic layer was then concentrated and purified on silica gel (0-10% MeOH in CH₂Cl₂) to provide the desired product. LCMS calculated for $C_{36}H_{40}F_3N_8O_5$ (M+H)⁺: m/z=721.3; found 721.3.

rt and stirred for 30 min. After completion, the reaction was diluted with water the precipitated product was collected and air dried overnight. LCMS calculated for $C_{19}H_{11}F_3N_3O_5$ (M+H)⁺: m/z=418.1; found 418.1.

Step 11. tert-butyl (2S,4S)-2-(cyanomethyl)-4-(4-(3-(dimethylamino)azetidin-1-yl)-7-(naphthalen-1-yl)-6-oxo-8-(trifluoromethyl)-6,7-dihydro-1H-imidazo[4,5-c][1,7]naphthyridin-1-yl)piperidine-1-carboxylate

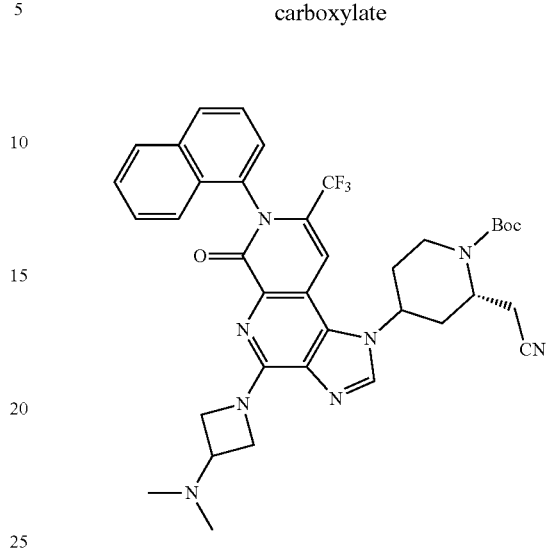

To a 100 mL round bottom flask was added tert-butyl (2S,4S)-2-(cyanomethyl)-4-((2-(3-(dimethylamino)azetidin-1-yl)-7-(naphthalen-1-yl)-3-nitro-8-oxo-6-(trifluoromethyl)-7,8-dihydro-1,7-naphthyridin-4-yl)amino)piperidine-1-carboxylate (401 mg, 0.503 mmol) and Pd/C (53.6 mg, 0.050 mmol). The flask was charged with nitrogen before MeOH (10 mL) was added. The reaction mixture was purged with hydrogen gas, and stirred for 2 h. After completion, the reaction was filtrated through a celite pad. The solvent was removed and the residue was added toluene (2 mL), triethyl orthoformate (385 µl, 2.31 mmol), and acetic acid (53 µl, 0.925 mmol). The mixture was heated to 100° C. for 3 h till the starting material is consumed. The solvent was then removed, the residue was dissolved in DCM and washed 1N NaOH solution, brine and dried over Na₂SO₄. The organic layer was then concentrated and purified on silica gel (0-10% MeOH in CH₂Cl₂) to provide the desired product. LCMS calculated for $C_{37}H_{40}F_3N_8O_3$ (M+H)⁺: m/z=701.3; found 701.3.

Step 12. 2-((2S,4S)-1-acryloyl-4-(4-(3-(dimethylamino)azetidin-1-yl)-7-(naphthalen-1-yl)-6-oxo-8-(trifluoromethyl)-6,7-dihydro-1H-imidazo[4,5-c][1,7]naphthyridin-1-yl)piperidin-2-yl)acetonitrile To a DCM (1 mL) solution of tert-butyl (2S,4S)-2-(cyanomethyl)-4-(4-(3-(dimethylamino)azetidin-1-yl)-7-(naphthalen-1-yl)-6-oxo-8-(trifluoromethyl)-6,7-dihydro-1H-imidazo[4,5-c][1,7]naphthyridin-1-yl)piperidine-1-carboxylate (20 mg, 0.029 mmol) was added 1 mL of TFA. The reaction was stirred for 1 h before the solvent was removed under vacuum. The residue was dissolved in DCM again, DIEA (7.56 µl, 0.043 mmol) and acryloyl chloride (3.92 mg, 0.043 mmol) were added sequentially at 0° C. After stirring for 10 min, the reaction was quenched by adding TFA. The mixture was diluted with acetonitrile/water and purified using prep-LCMS (XBridge C18 column, eluting with a gradient of acetonitrile/water containing 0.1% TFA, at flow rate of 60 mL/min) to afford the desired products as TFA salt. LCMS calculated for $C_{35}H_{34}F_3N_8O_2$ (M+H)⁺: m/z=655.3; found 655.3.

Example 7. 2-((2S)-1-acryloyl-4-(4-(2-methylpyridin-3-yl)-7-(naphthalen-1-yl)-6-oxo-8-(trifluoromethyl)-6,7-dihydro-1H-imidazo[4,5-c][1,7]naphthyridin-1-yl)piperidin-2-yl)acetonitrile

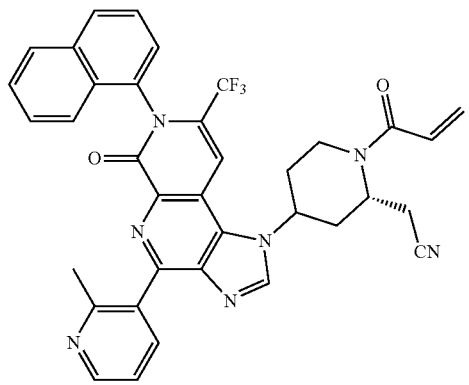 [SMILES: C=CC(=O)N1CCC(n2cnc3c(-c4cccnc4C)nc4c(=O)n(-c5cccc6ccccc56)c(C(F)(F)F)cc4c32)C[C@H]1CC#N]

Step 1. 4-chloro-2-hydroxy-7-(naphthalen-1-yl)-3-nitro-6-(trifluoromethyl)-1,7-naphthyridin-8(7H)-one

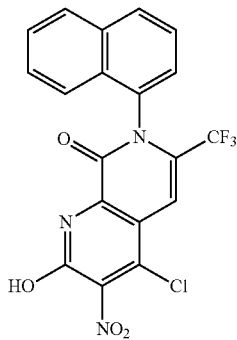

To a 100 mL round bottom flask was added 2,4-dihydroxy-7-(naphthalen-1-yl)-3-nitro-6-(trifluoromethyl)-1,7-naphthyridin-8(7H)-one (1.0 g, 2.396 mmol) and POCl$_3$ (1.117 ml, 11.98 mmol) was added DIEA (0.837 ml, 4.79 mmol) at 0° C. dropwise. The reaction mixture was then heated at 100° C. for 10 min before cooled to rt and poured on ice. The solid product was then collected and washed with water, air dried overnight. LCMS calculated for C$_{19}$H$_{10}$ClF$_3$N$_3$O$_4$ (M+H)$^+$: m/z=436.0; found 436.0.

Step 2. tert-butyl (2S,4S)-2-(cyanomethyl)-4-((2-hydroxy-7-(naphthalen-1-yl)-3-nitro-8-oxo-6-(trifluoromethyl)-7,8-dihydro-1,7-naphthyridin-4-yl)amino)piperidine-1-carboxylate

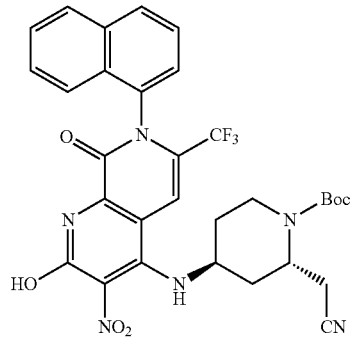 [SMILES: CC(C)(C)OC(=O)N1CC[C@H](Nc2c([N+](=O)[O-])c(O)nc3c(=O)n(-c4cccc5ccccc45)c(C(F)(F)F)cc23)C[C@H]1CC#N]

To a DMSO (5 mL) solution of 4-chloro-2-hydroxy-7-(naphthalen-1-yl)-3-nitro-6-(trifluoromethyl)-1,7-naphthyridin-8(7H)-one (1.044 g, 2.396 mmol) was added tert-butyl (2S,4S)-4-amino-2-(cyanomethyl)piperidine-1-carboxylate (0.602 g, 2.52 mmol), and DIPEA (0.837 ml, 4.79 mmol). The reaction was heated at 100° C. for 30 min before quenched by diluting with water, and extracted with EtOAc. The organic layer was washed with water, brine and dried over Na$_2$SO$_4$. The organic layer was then concentrated and purified on silica gel (0-10% MeOH in CH$_2$Cl$_2$) to provide the desired product. LCMS calculated for C$_{31}$H$_{30}$F$_3$N$_6$O$_6$ (M+H)$^+$: m/z=639.2; found 639.2.

Step 3. tert-butyl (2S)-2-(cyanomethyl)-4-(4-hydroxy-7-(naphthalen-1-yl)-6-oxo-8-(trifluoromethyl)-6,7-dihydro-1H-imidazo[4,5-c][1,7]naphthyridin-1-yl)piperidine-1-carboxylate

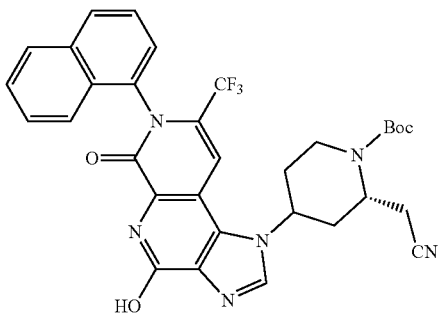 [SMILES: CC(C)(C)OC(=O)N1CCC(n2cnc3c(O)nc4c(=O)n(-c5cccc6ccccc56)c(C(F)(F)F)cc4c32)C[C@H]1CC#N]

To a 100 mL round bottom flask was added tert-butyl (2S,4S)-2-(cyanomethyl)-4-((2-hydroxy-7-(naphthalen-1-yl)-3-nitro-8-oxo-6-(trifluoromethyl)-7,8-dihydro-1,7-naphthyridin-4-yl)amino)piperidine-1-carboxylate (765 mg, 1.198 mmol) and Pd/C (128 mg, 0.1198 mmol). The flask was charged with nitrogen before MeOH (10 mL) was added. The reaction mixture was purged with hydrogen gas, and stirred for 2 h. After completion, the reaction was filtrated through a celite pad. The solvent was removed and the residue was added toluene (5 mL), triethyl orthoformate (770 μl, 4.6 mmol), and acetic acid (106 μl, 1.85 mmol). The mixture was heated to 100° C. for 3 h till the starting material is consumed. The solvent was then removed, the residue was dissolved in DCM and washed 1N NaOH solution, brine and dried over Na$_2$SO$_4$. The organic layer was then concentrated and purified on silica gel (0-10% MeOH in CH$_2$Cl$_2$) to provide the desired product. LCMS calculated for C$_{32}$H$_{30}$F$_3$N$_6$O$_4$ (M+H)$^+$: m/z=619.2; found 619.2.

Step 4. tert-butyl (2S)-2-(cyanomethyl)-4-(4-(2-methylpyridin-3-yl)-7-(naphthalen-1-yl)-6-oxo-8-(trifluoromethyl)-6,7-dihydro-1H-imidazo[4,5-c][1,7]naphthyridin-1-yl)piperidine-1-carboxylate

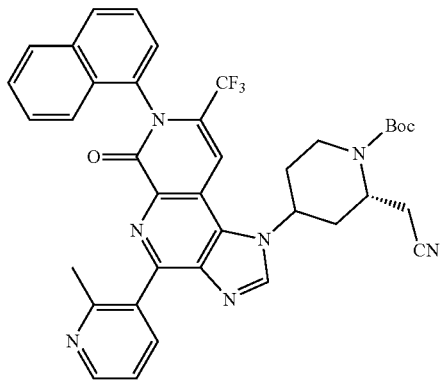 [SMILES: Cc1ncccc1-c1nc2c(=O)n(-c3cccc4ccccc34)c(C(F)(F)F)cc2c2c1ncn2C1CCN(C(=O)OC(C)(C)C)[C@H](CC#N)C1]

To a DCM (10 mL) solution of tert-butyl (2S)-2-(cyanomethyl)-4-(4-hydroxy-7-(naphthalen-1-yl)-6-oxo-8-(trifluoromethyl)-6,7-dihydro-1H-imidazo[4,5-c][1,7]naphthyridin-1-yl)piperidine-1-carboxylate (70 mg, 0.113 mmol) was added DIPEA (39.5 µl, 0.226 mmol) at 0° C. followed by adding triflate anhydride (1 M DCM solution, 0.147 µl, 0.147 mmol). The mixture was stirred for 30 min before quenched with sat. NaHCO$_3$ solution. The reaction mixture was extracted with DCM. The organic layer was washed with water, brine and dried over Na$_2$SO$_4$. The organic layer was then concentrated to dryness and dissolved in dioxane (1 mL)/H$_2$O (0.1 mL), Cs$_2$CO$_3$ (73.7 mg, 0.226 mmol), tetrakis(triphenylphosphine)palladium(0) (130 mg, 0.113 mmol) and (3-methylpyridin-2-yl)boronic acid (23.24 mg, 0.170 mmol) were then added to the reaction mixture. The reaction was then heated at 100° C. for 1 h, before quenched with adding DCM. The reaction mixture was then concentrated and purified on silica gel (0-10% MeOH in CH$_2$Cl$_2$) to provide the desired product. LCMS calculated for C$_{38}$H$_{35}$F$_3$N$_7$O$_3$ (M+H)$^+$: m/z=694.3; found 694.3.

Step 5. 2-((2S,4S)-1-acryloyl-4-(4-(2-methylpyridin-3-yl)-7-(naphthalen-1-yl)-6-oxo-8-(trifluoromethyl)-6,7-dihydro-1H-imidazo[4,5-c][1,7]naphthyridin-1-yl)piperidin-2-yl)acetonitrile

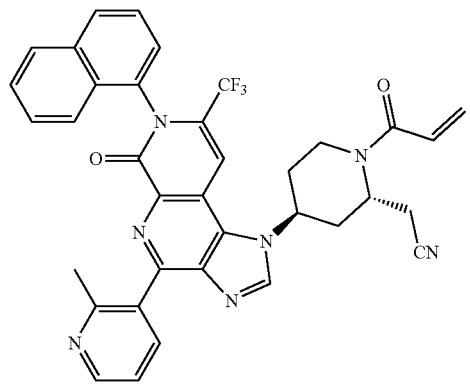 [SMILES: C=CC(=O)N1CC[C@H](n2cnc3c(-c4cccnc4C)nc4c(=O)n(-c5cccc6ccccc56)c(C(F)(F)F)cc4c32)C[C@H]1CC#N]

To a DCM (1 mL) solution of tert-butyl (2S,4S)-2-(cyanomethyl)-4-(4-(2-methylpyridin-3-yl)-7-(naphthalen-1-yl)-6-oxo-8-(trifluoromethyl)-6,7-dihydro-1H-imidazo[4,5-c][1,7]naphthyridin-1-yl)piperidine-1-carboxylate (20 mg, 0.029 mmol) was added 1 mL of TFA. The reaction was stirred for 1 h before the solvent was removed under vacuum. The residue was dissolved in DCM again, DIEA (7.56 µl, 0.043 mmol) and acryloyl chloride (3.92 mg, 0.043 mmol) were added sequentially at 0° C. After stirring for 10 min, the reaction was quenched by adding TFA. The mixture was diluted with acetonitrile/water and purified using prep-LCMS (XBridge C18 column, eluting with a gradient of acetonitrile/water containing 0.1% TFA, at flow rate of 60 mL/min) to afford the desired products as TFA salt. LCMS calculated for C$_{36}$H$_{29}$F$_3$N$_7$O$_2$ (M+H)$^+$: m/z=648.2; found 648.2.

Example 8. 2-((2S,4S)-1-acryloyl-4-(7-(3-chloro-2-methylphenyl)-4-((S)-1-((S)-1-methylpyrrolidin-2-yl)ethoxy)-6-oxo-8-(trifluoromethyl)-6,7-dihydro-1H-imidazo[4,5-c][1,7]naphthyridin-1-yl)piperidin-2-yl)acetonitrile

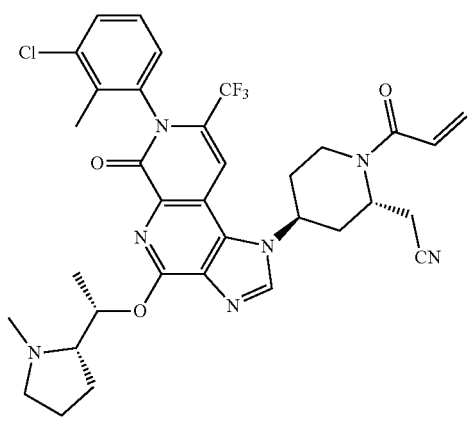 [SMILES: C=CC(=O)N1CC[C@H](n2cnc3c(O[C@@H](C)[C@@H]4CCCN4C)nc4c(=O)n(-c5cccc(Cl)c5C)c(C(F)(F)F)cc4c32)C[C@H]1CC#N]

Step 1. tert-butyl (2S,4S)-4-((7-(3-chloro-2-methylphenyl)-2-(methylthio)-3-nitro-8-oxo-6-(trifluoromethyl)-7,8-dihydro-1,7-naphthyridin-4-yl)amino)-2-(cyanomethyl)piperidine-1-carboxylate

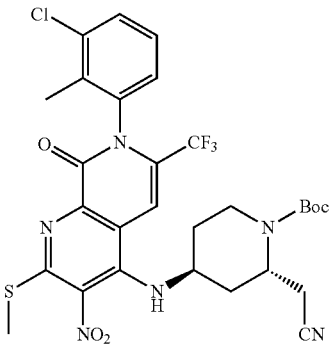 [SMILES: CSc1nc2c(=O)n(-c3cccc(Cl)c3C)c(C(F)(F)F)cc2c(N[C@H]2CCN(C(=O)OC(C)(C)C)[C@H](CC#N)C2)c1[N+](=O)[O-]]

To a DCM (100 mL) solution of 7-(3-chloro-2-methylphenyl)-2,4-dihydroxy-3-nitro-6-(trifluoromethyl)-1,7-naphthyridin-8(7H)-one (1.0 g, 2.406 mmol) was added DIPEA (1.260 ml, 7.22 mmol) at −78° C. followed by adding triflate anhydride (1 M DCM solution, 7.22 ml, 7.22 mmol). The mixture was warmed to 0° C., and stirred for 30 min before cooled to −78° C. again. A DCM solution of DIPEA (0.840 ml, 4.81 mmol), and tert-butyl (2S,4S)-4-amino-2-(cyanomethyl)piperidine-1-carboxylate (1.151 g, 4.81 mmol) was then added to the reaction mixture through syringe at −78° C. dropwise. The resulting solution was stirred for 30 min at −78° C. before sodium thiomethoxide (0.253 g, 3.61 mmol) was added. The reaction was then warmed to rt and stirred for another 30 min before quenched with sat. NaHCO$_3$ solution. The reaction mixture was extracted with DCM. The organic layer was washed with water, brine and dried over Na$_2$SO$_4$. The organic layer was then concentrated and purified on silica gel (0-10% MeOH in CH$_2$Cl$_2$) to provide the desired product. LCMS calculated for C$_{29}$H$_{31}$ClF$_3$N$_6$O$_5$S (M+H)$^+$: m/z=667.2; found 667.2.

Step 2. tert-butyl (2S,4S)-4-(7-(3-chloro-2-methylphenyl)-4-(methylthio)-6-oxo-8-(trifluoromethyl)-6,7-dihydro-1H-imidazo[4,5-c][1,7]naphthyridin-1-yl)-2-(cyanomethyl)piperidine-1-carboxylate

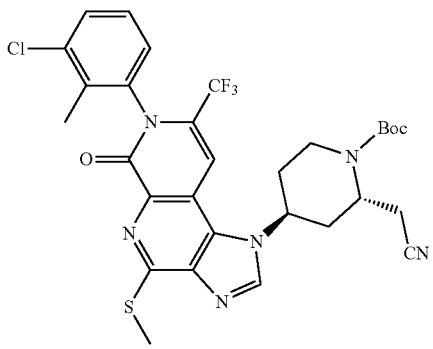 [SMILES: CSc1nc2c(=O)n(-c3cccc(Cl)c3C)c(C(F)(F)F)cc2c2c1ncn2[C@H]1CCN(C(=O)OC(C)(C)C)[C@H](CC#N)C1]

To a 100 mL round bottom flask was added tert-butyl (2S,4S)-4-((7-(3-chloro-2-methylphenyl)-2-(methylthio)-3-nitro-8-oxo-6-(trifluoromethyl)-7,8-dihydro-1,7-naphthyridin-4-yl)amino)-2-(cyanomethyl)piperidine-1-carboxylate (802 mg, 1.203 mmol) and Pd/C (128 mg, 0.120 mmol). The flask was charged with nitrogen before MeOH (10 mL) was added. The reaction mixture was purged with hydrogen gas, and stirred for 2 h. After completion, the reaction was filtrated through a celite pad. The solvent was removed and the residue was added toluene (5 mL), triethyl orthoformate (770 μl, 4.62 mmol), and acetic acid (106 μl, 1.85 mmol). The mixture was heated to 100° C. for 3 h till the starting material is consumed. The solvent was then removed, the residue was dissolved in DCM and washed 1N NaOH solution, brine and dried over Na$_2$SO$_4$. The organic layer was then concentrated and purified on silica gel (0-10% MeOH in CH$_2$Cl$_2$) to provide the desired product. LCMS calculated for C$_{30}$H$_{31}$ClF$_3$N$_6$O$_3$S (M+H)$^+$: m/z=647.2; found 647.2.

Step 3. tert-butyl (2S,4S)-4-(7-(3-chloro-2-methylphenyl)-4-((S)-1-((S)-1-methylpyrrolidin-2-yl)ethoxy)-6-oxo-8-(trifluoromethyl)-6,7-dihydro-1H-imidazo[4,5-c][1,7]naphthyridin-1-yl)-2-(cyanomethyl)piperidine-1-carboxylate

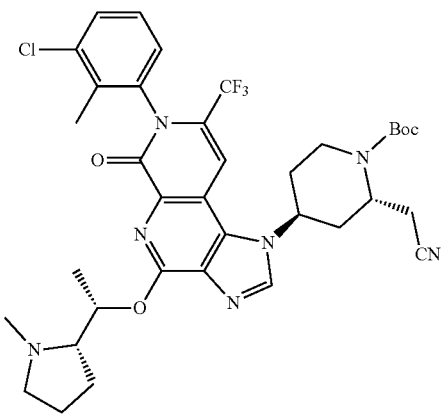 [SMILES: Cc1c(Cl)cccc1-n1c(C(F)(F)F)cc2c(nc(O[C@@H](C)[C@@H]3CCCN3C)c3ncn([C@H]4CCN(C(=O)OC(C)(C)C)[C@H](CC#N)C4)c32)c1=O]

tert-Butyl (2S,4S)-4-(7-(3-chloro-2-methylphenyl)-4-(methylthio)-6-oxo-8-(trifluoromethyl)-6,7-dihydro-1H-imidazo[4,5-c][1,7]naphthyridin-1-yl)-2-(cyanomethyl)piperidine-1-carboxylate (100 mg, 0.154 mmol) was dissolved in DCM (2 mL) and cooled to 0° C. mCPBA (45.0 mg, 0.201 mmol) was added in one portion and the mixture was stirred for 10 min before washed with sat. NaHCO$_3$. The organic layers were dried over MgSO$_4$, filtered, and concentrated. The concentrated crude was dissolved in THF (1.0 mL) and added to a pre-stirred solution of (S)-1-((S)-1-methylpyrrolidin-2-yl)ethan-1-ol (100 mg, 0.771 mmol) and LiHMDS in THF (771 μl, 0.771 mmol) in THF (1.000 ml) at 0° C. The mixture was quenched by sat. NH$_4$Cl and extracted with EtOAc. The organic layers were dried over MgSO$_4$, filtered, concentrated, and purified on silica gel (0-10% MeOH in CH$_2$Cl$_2$) to provide the desired product. LCMS calculated for C$_{36}$H$_{42}$ClF$_3$N$_7$O$_4$ (M+H)$^+$: m/z=728.3; found 728.3.

Step 4. 2-((2S,4S)-1-acryloyl-4-(7-(3-chloro-2-methylphenyl)-4-((S)-1-((S)-1-methylpyrrolidin-2-yl)ethoxy)-6-oxo-8-(trifluoromethyl)-6,7-dihydro-1H-imidazo[4,5-c][1,7]naphthyridin-1-yl)piperidin-2-yl)acetonitrile To a DCM (1 mL) solution of tert-butyl (2S,4S)-4-(7-(3-chloro-2-methylphenyl)-4-((S)-1-((S)-1-methylpyrrolidin- 2-yl)ethoxy)-6-oxo-8-(trifluoromethyl)-6,7-dihydro-1H-imidazo[4,5-c][1,7]naphthyridin-1-yl)-2-(cyanomethyl)piperidine-1-carboxylate (22.47 mg, 0.031 mmol) was added 1 mL of TFA. The reaction was stirred for 1 h before the solvent was removed under vacuum. The residue was dissolved in DCM again, DIPEA (7.56 µl, 0.043 mmol) and acryloyl chloride (3.92 mg, 0.043 mmol) were added sequentially at 0° C. After stirring for 10 min, the reaction was quenched by adding TFA. The mixture was diluted with acetonitrile/water and purified using prep-LCMS (XBridge C18 column, eluting with a gradient of acetonitrile/water containing 0.1% TFA, at flow rate of 60 mL/min) to afford the desired products as TFA salt. LCMS calculated for $C_{34}H_{36}ClF_3N_7O_3$ (M+H)$^+$: m/z=682.2; found 682.2.

Example 9. 2-((2S,4S)-1-(but-2-ynoyl)-4-(7-(3-chloro-2-methylphenyl)-4-((S)-1-((S)-1-methylpyrrolidin-2-yl)ethoxy)-6-oxo-8-(trifluoromethyl)-6,7-dihydro-1H-imidazo[4,5-c][1,7]naphthyridin-1-yl)piperidin-2-yl)acetonitrile

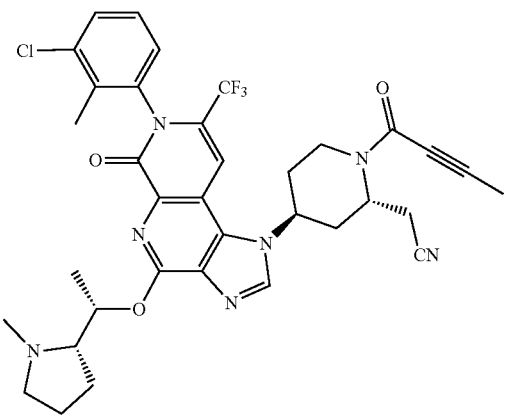 [SMILES: CC#CC(=O)N1CC[C@H](n2cnc3c(O[C@@H](C)[C@@H]4CCCN4C)nc4c(=O)n(-c5cccc(Cl)c5C)c(C(F)(F)F)cc4c32)C[C@H]1CC#N]

2-((2S,4S)-4-(7-(3-chloro-2-methylphenyl)-4-((S)-1-((S)-1-methylpyrrolidin-2-yl)ethoxy)-6-oxo-8-(trifluoromethyl)-6,7-dihydro-1H-imidazo[4,5-c][1,7]naphthyridin-1-yl)piperidin-2-yl)acetonitrile (From example 8, step 4, 19.38 mg, 0.031 mmol) was dissolved in THF (0.5 mL), but-2-ynoic acid (4.8 mg, 0.05 mmol), HATU (32.9 mg, 0.086 mmol), and DIPEA (15.0 µl, 0.086 mmol) were added sequentially. The reaction was stirred for 4 h before quenched by adding water. The mixture was diluted with acetonitrile/water and purified using prep-LCMS (XBridge C18 column, eluting with a gradient of acetonitrile/water containing 0.1% TFA, at flow rate of 60 mL/min) to afford the desired products as TFA salt. LCMS calculated for $C_{35}H_{36}ClF_3N_7O_3$ (M+H)$^+$: m/z=694.2; found 694.2.

Example 10. 2-((2S,4S)-4-(7-(3-chloro-2-methylphenyl)-4-((S)-1-((S)-1-methylpyrrolidin-2-yl)ethoxy)-6-oxo-8-(trifluoromethyl)-6,7-dihydro-1H-imidazo[4,5-c][1,7]naphthyridin-1-yl)-1-(2-fluoroacryloyl)piperidin-2-yl)acetonitrile

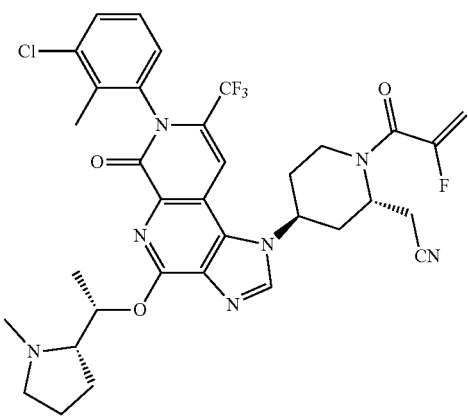 [SMILES: C=C(F)C(=O)N1CC[C@H](n2cnc3c(O[C@@H](C)[C@@H]4CCCN4C)nc4c(=O)n(-c5cccc(Cl)c5C)c(C(F)(F)F)cc4c32)C[C@H]1CC#N]

This compound was prepared according to the procedure described in Example 9, replacing but-2-ynoic acid with 2-fluoroacrylic acid. The reaction was diluted with acetonitrile/water and purified using prep-LCMS (XBridge C18 column, eluting with a gradient of acetonitrile/water containing 0.1% TFA, at flow rate of 60 mL/min) to afford the desired products as TFA salt. LCMS calculated for $C_{34}H_{35}ClF_4N_7O_3$ (M+H)$^+$: m/z=700.2; found 700.2.

Example 11. 2-((2S,4S)-1-acryloyl-4-(7-(3-chloro-2-methylphenyl)-4-(3-(dimethylamino)-3-methylazetidin-1-yl)-6-oxo-8-(trifluoromethyl)-6,7-dihydro-1H-[1,2,3]triazolo[4,5-c][1,7]naphthyridin-1-yl)piperidin-2-yl)acetonitrile

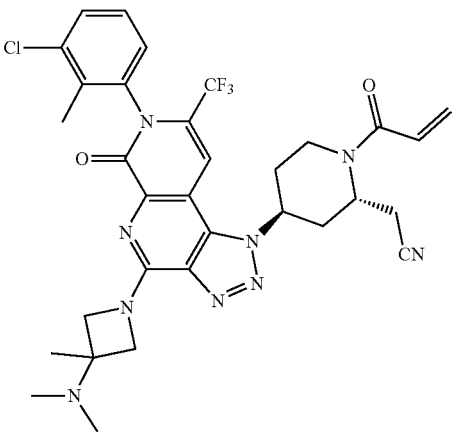 [SMILES: C=CC(=O)N1CC[C@H](n2nnc3c(N4CC(C)(N(C)C)C4)nc4c(=O)n(-c5cccc(Cl)c5C)c(C(F)(F)F)cc4c32)C[C@H]1CC#N]

Step 1. 7-(3-chloro-2-methylphenyl)-2,4-dihydroxy-3-nitro-6-(trifluoromethyl)-1,7-naphthyridin-8(7H)-one

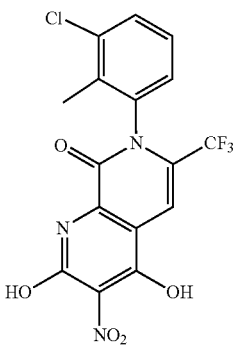 [SMILES: Cc1c(Cl)cccc1-n1c(C(F)(F)F)cc2c(O)c([N+](=O)[O-])c(O)nc2c1=O]

This compound was prepared according to the procedure described in Example 6, replacing naphthalen-1-amine with 3-chloro-2-methylaniline in step 1. The reaction was diluted with water the precipitated product was collected and air dried overnight. LCMS calculated for $C_{16}H_{10}ClF_3N_3O_5$ (M+H)$^+$: m/z=416.1; found 416.1.

Step 2. tert-butyl (2S,4S)-4-((7-(3-chloro-2-methylphenyl)-2-(3-(dimethylamino)-3-methylazetidin-1-yl)-3-nitro-8-oxo-6-(trifluoromethyl)-7,8-dihydro-1,7-naphthyridin-4-yl)amino)-2-(cyanomethyl)piperidine-1-carboxylate

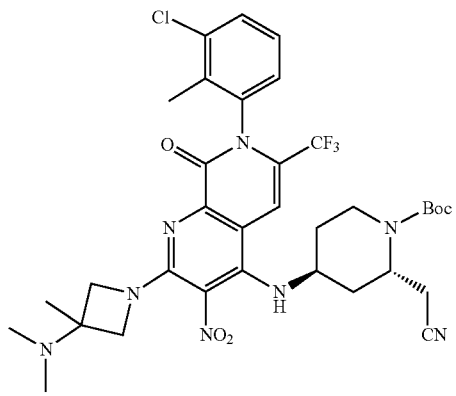 [SMILES: Cc1c(Cl)cccc1-n1c(C(F)(F)F)cc2c(N[C@H]3CCN(C(=O)OC(C)(C)C)[C@H](CC#N)C3)c([N+](=O)[O-])c(N3CC(C)(N(C)C)C3)nc2c1=O]

To a DCM (100 mL) solution of 7-(3-chloro-2-methylphenyl)-2,4-dihydroxy-3-nitro-6-(trifluoromethyl)-1,7-naphthyridin-8(7H)-one (500 mg, 1.203 mmol) was added DIPEA (630 µl, 3.61 mmol) at −78° C. followed by adding triflate anhydride(1 M DCM solution, 3610 µl, 3.61 mmol). The mixture was warmed to 0° C., and stirred for 30 min before cooled to −78° C. again. A DCM solution of DIPEA (420 µl, 2.406 mmol), and tert-butyl (2S,4S)-4-amino-2-(cyanomethyl)piperidine-1-carboxylate (576 mg, 2.406 mmol) was then added to the reaction mixture through syringe at −78° C. dropwise. The resulting solution was stirred for 30 min at −78° C. before N,N,3-trimethylazetidin-3-amine, 2HCl (450 mg, 2.406 mmol) and DIPEA (1050 µl, 6.01 mmol) were added. The reaction was then warmed to rt and stirred for another 30 min before quenched with sat. NaHCO₃ solution. The reaction mixture was extracted with DCM. The organic layer was washed with water, brine and dried over Na₂SO₄. The organic layer was then concentrated and purified on silica gel (0-10% MeOH in CH₂Cl₂) to provide the desired product. LCMS calculated for $C_{34}H_{41}ClF_3N_8O_5$ (M+H)$^+$: m/z=733.3; found 733.3.

Step 3. tert-butyl (2S)-4-(7-(3-chloro-2-methylphenyl)-4-(3-(dimethylamino)-3-methylazetidin-1-yl)-6-oxo-8-(trifluoromethyl)-6,7-dihydro-1H-[1,2,3]triazolo[4,5-c][1,7]naphthyridin-1-yl)-2-(cyanomethyl)piperidine-1-carboxylate

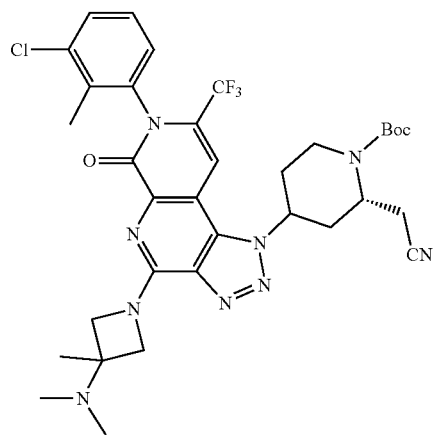 [SMILES: Cc1c(Cl)cccc1-n1c(C(F)(F)F)cc2c(nc(N3CC(C)(N(C)C)C3)c3nnn(C4CCN(C(=O)OC(C)(C)C)[C@H](CC#N)C4)c32)c1=O]

To a 100 mL round bottom flask was added tert-butyl (2S,4S)-4-((7-(3-chloro-2-methylphenyl)-2-(3-(dimethylamino)-3-methylazetidin-1-yl)-3-nitro-8-oxo-6-(trifluoromethyl)-7,8-dihydro-1,7-naphthyridin-4-yl)amino)-2-(cyanomethyl)piperidine-1-carboxylate (882 mg, 1.203 mmol) and Pd/C (107.2 mg, 0.10 mmol). The flask was charged with nitrogen before MeOH (10 mL) was added. The reaction mixture was purged with hydrogen gas, and stirred for 2 h. After completion, the reaction was filtrated through a celite pad. The solvent was removed and the residue was added acetic acid (2 mL), sodium nitrite (0.124 g, 1.800 mmol). The mixture was stirred for 30 min till the starting material is consumed. The solvent was then removed, the residue was dissolved in DCM and washed 1N NaOH solution, brine and dried over Na₂SO₄. The organic layer was then concentrated and purified on silica gel (0-10% MeOH in CH₂Cl₂) to provide the desired product. LCMS calculated for $C_{34}H_{40}ClF_3N_9O_3$ (M+H)$^+$: m/z=714.3; found 714.3.

Step 4. 2-((2S,4S)-1-acryloyl-4-(7-(3-chloro-2-methylphenyl)-4-(3-(dimethylamino)-3-methylazetidin-1-yl)-6-oxo-8-(trifluoromethyl)-6,7-dihydro-1H-[1,2,8]triazolo[4,5-c][1,7]naphthyridin-1-yl)piperidin-2-yl)acetonitrile To a DCM (1 mL) solution of tert-butyl (2S)-4-(7-(3-chloro-2-methylphenyl)-4-(3-(dimethylamino)-3-methylazetidin-1-yl)-6-oxo-8-(trifluoromethyl)-6,7-dihydro-1H-[1,2,3]triazolo[4,5-c][1,7]naphthyridin-1-yl)-2-(cyanomethyl)piperidine-1-carboxylate (20 mg, 0.029 mmol) was added 1 mL of TFA. The reaction was stirred for 1 h before the solvent was removed under vacuum. The residue was dissolved in DCM again, DIPEA (7.56 µl, 0.043 mmol) and acryloyl chloride (3.92 mg, 0.043 mmol) were added sequentially at 0° C. After stirring for 10 min, the reaction was quenched by adding TFA. The mixture was diluted with acetonitrile/water and purified using prep-LCMS (XBridge C18 column, eluting with a gradient of acetonitrile/water containing 0.1% TFA, at flow rate of 60 mL/min) to afford the desired products as TFA salt. LCMS calculated for $C_{32}H_{34}ClF_3N_9O_2$ (M+H)$^+$: m/z=668.3; found 668.3.

Example 12. 2-((2S,4S)-4-(7-(3-chloro-2-methylphenyl)-4-(3-(dimethylamino)-3-methylazetidin-1-yl)-6-oxo-8-(trifluoromethyl)-6,7-dihydro-1H-[1,2,3]triazolo[4,5-c][1,7]naphthyridin-1-yl)-1-((E)-4-fluorobut-2-enoyl)piperidin-2-yl)acetonitrile

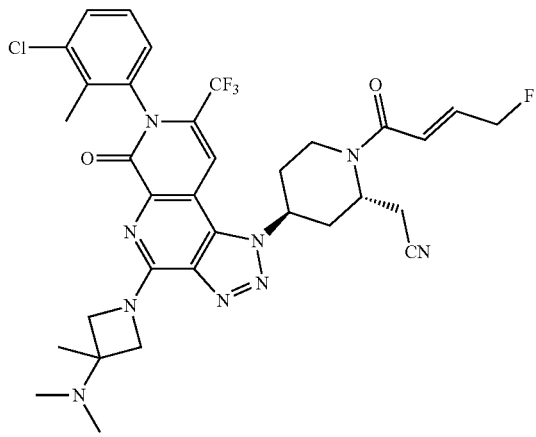 [SMILES: Cc1c(Cl)cccc1-n1c(C(F)(F)F)cc2c(nc(N3CC(C)(N(C)C)C3)c3nnn([C@H]4CCN(C(=O)/C=C/CF)[C@H](CC#N)C4)c32)c1=O]

2-((2S,4S)-4-(7-(3-chloro-2-methylphenyl)-4-(3-(dimethylamino)-3-methylazetidin-1-yl)-6-oxo-8-(trifluoromethyl)-6,7-dihydro-1H-[1,2,3]triazolo[4,5-c][1,7]naphthyridin-1-yl)piperidin-2-yl)acetonitrile (From example 11, step 4, 20 mg, 0.033 mmol) was dissolved in THF (0.5 mL), (E)-4-fluorobut-2-enoic acid (5.08 mg, 0.049 mmol), HATU (32.9 mg, 0.086 mmol), and DIPEA (15.0 µl, 0.086 mmol) were added sequentially. The reaction was stirred for 4 h before quenched by adding water. The mixture was diluted with acetonitrile/water and purified using prep-LCMS (XBridge C18 column, eluting with a gradient of acetonitrile/water containing 0.1% TFA, at flow rate of 60 mL/min) to afford the desired products as TFA salt. LCMS calculated for $C_{33}H_{35}ClF_4N_9O_2$ (M+H)$^+$: m/z=700.3; found 700.2.

Example A. GDP-GTP Exchange Assay

The inhibitor potency of the exemplified compounds was determined in a fluorescence based guanine nucleotide exchange assay, which measures the exchange of bodipy-GDP (fluorescently labeled GDP) for GppNHp (Non-hydrolyzable GTP analog) to generate the active state of KRAS in the presence of SOS1 (guanine nucleotide exchange factor). Inhibitors were serially diluted in DMSO and a volume of 0.1 µL was transferred to the wells of a black low volume 384-well plate. 5 µL/well volume of bodipy-loaded KRAS G12C diluted to 5 nM in assay buffer (25 mM Hepes pH 7.5, 50 mM NaCl, 10 mM MgCl2 and 0.01% Brij-35) was added to the plate and pre-incubated with inhibitor for 2 hours at ambient temperature. Appropriate controls (enzyme with no inhibitor or with a G12C inhibitor (AMG-510)) were included on the plate. The exchange was initiated by the addition of a 5 µL/well volume containing 1 mM GppNHp and 300 nM SOS1 in assay buffer. The 10 µL/well reaction concentration of the bodipy-loaded KRAS G12C, GppNHp, and SOS1 were 2.5 nM, 500 uM, and 150 nM, respectively. The reaction plates were incubated at ambient temperature for 2 hours, a time estimated for complete GDP-GTP exchange in the absence of inhibitor. For the KRAS G12D and G12V mutants, similar guanine nucleotide exchange assays were used with 2.5 nM as final concentration for the bodipy loaded KRAS proteins and with 4 hours and 3 hours incubation after adding GppNHp-SOS1 mixture for G12D and G12V respectively. A cyclic peptide described to selectively bind G12D mutant (Sakamoto et al., BBRC 484.3 (2017), 605-611) or internal compounds with confirmed binding were used as positive controls in the assay plates. Fluorescence intensities were measured on a PheraStar plate reader instrument (BMG Labtech) with excitation at 485 nm and emission at 520 nm.

Either GraphPad prism or XLfit was used to analyze the data. The $IC_{50}$ values were derived by fitting the data to a four parameter logistic equation producing a sigmoidal dose-response curve with a variable Hill coefficient. Prism equation: Y=Bottom+(Top−Bottom)/(1+10^((Log $IC_{50}$−X)*Hill slope)); XLfit equation: Y=(A+((B−A)/(1+((X/C)^D)))) where X is the logarithm of inhibitor concentration and Y is the response.

The KRAS_G12C exchange assay $IC_{50}$ data and KRAS_G12C pERK assay $IC_{50}$ data are provided in Table 1 below. The symbol "†" indicates $IC_{50}$≤100 nM, "††" indicates $IC_{50}$>100 nM but ≤1 µM; and "†††" indicates $IC_{50}$ is >1 µM but ≤5 µM, "††††" indicates $IC_{50}$ is >5 µM but ≤10 µM. "NA" indicates $IC_{50}$ not available.

TABLE 1

| Ex. No. | G12C_exchange | G12C_pERK |
|---|---|---|
| 1 | † | ††† |
| 2 | † | ††† |
| 4 | †† | NA |
| 5 | † | ††† |
| 6 | † | † |
| 7 | † | † |
| 8 | † | † |
| 9 | † | † |
| 10 | † | †† |
| 11 | † | † |
| 12 | † | † |

The KRAS_G12D exchange assay $IC_{50}$ data are provided in Table 2 below. The symbol "†" indicates $IC_{50}$≤100 nM, "††" indicates $IC_{50}$>100 nM but ≤1 µM; and "†††" indicates $IC_{50}$ is >1 µM but ≤5 µM, "††††" indicates $IC_{50}$ is >5 µM but ≤10 µM. "NA" indicates $IC_{50}$ not available.

TABLE 2

| Ex. No. | G12D_exchange |
|---|---|
| 3 | †† |

Example B: Luminescent Viability Assay

MIA PaCa-2 (KRAS G12C; ATCC® CRL-1420), A427 (KRAS G12D; ATCC® HTB53) and NCI-H838 (KRAS WT; ATCC® CRL-5844) cells are cultured in RPMI 1640 media supplemented with 10% FBS (Gibco/Life Technologies). The cells are seeded ($5 \times 10^3$ cells/well/in 50 uL) into black, clear bottomed 96-well Greiner tissue culture plates and cultured overnight at 37° C., 5% $CO_2$. After overnight culture, 50 uL per well of serially diluted test compounds (2× final concentration) are added to the plates and incubated for 3 days. At the end of the assay, 100 ul/well of CellTiter-Glo reagent (Promega) is added. Luminescence is read after 15 minutes with a TopCount (PerkinElmer). $IC_{50}$ determination is performed by fitting the curve of percent inhibition versus the log of the inhibitor concentration using the GraphPad Prism 7 software.

Example C: Cellular pERK HTRF Assay

MIA PaCa-2 (KRAS G12C; ATCC® CRL-1420), A427 (KRAS G12D; ATCC® HTB53), HPAF-II (KRAS G12D; ATCC® CRL-1997) and NCI-H838 (KRAS WT; ATCC® CRL-5844) cells are purchased from ATCC and maintained in RPMI 1640 media supplemented with 10% FBS (Gibco/Life Technologies). The cells are plated at 5000 cells per well (8 uL) into Greiner 384-well low volume, flat-bottom, tissue culture treated white plates and incubated overnight at 37° C., 5% $CO_2$. The next morning, test compound stock solutions are diluted in media at 3× the final concentration, and 4 uL are added to the cells. The plate is mixed by gentle rotation for 30 seconds (250 rpm) at room temperature. The cells are incubated with the KRAS G12C and G12D compounds for 4 hours or 2 hours respectively at 37° C., 5% $CO_2$.

4 uL of 4× lysis buffer with blocking reagent (1:25) (Cisbio) are added to each well and plates are rotated gently (300 rpm) for 30 minutes at room temperature. 4 uL per well of Cisbio anti Phospho-ERK 1/2 d2 is mixed with anti Phospho-ERK 1/2 Cryptate (1:1) are added to each well, mixed by rotation and incubated overnight in the dark at room temperature. Plates are read on the Pherastar plate reader at 665 nm and 620 nm wavelengths. $IC_{50}$ determination is performed by fitting the curve of inhibitor percent inhibition versus the log of the inhibitor concentration using the GraphPad Prism 7 software.

Example D: Whole Blood pERK1/2 HTRF Assay

MIA PaCa-2 cells (KRAS G12C; ATCC® CRL-1420) and HPAF-II (KRAS G12D; ATCC® CRL-1997) are maintained in RPMI 1640 with 10% FBS (Gibco/Life Technologies). The cells are seeded into 96 well tissue culture plates (Corning #3596) at 25000 cells per well in 100 uL media and cultured for 2 days at 37° C., 5% $CO_2$ so that they are approximately 80% confluent at the start of the assay. Whole Blood are added to the 1 uL dots of compounds (prepared in DMSO) in 96 well plates and mixed gently by pipetting up and down so that the concentration of the compound in blood is 1× of desired concentration. The media is aspirated from the cells and 50 uL per well of whole blood with G12C or G12D compound is added and incubated for 4 or 2 hours respectively at 37° C., 5% $CO_2$. After dumping the blood, the plates are gently washed twice by adding PBS to the side of the wells and dumping the PBS from the plate onto a paper towel, tapping the plate to drain well. 50 ul/well of 1× lysis buffer #1 (Cisbio) with blocking reagent (1:25) (Cisbio) is then added and incubated at room temperature for 30 minutes with shaking (250 rpm). Following lysis, 16 uL of lysate is transferred into 384-well Greiner small volume white plate using an Assist Plus (Integra Biosciences, NH). 4 uL of 1:1 mixture of anti Phospho-ERK 1/2 d2 and anti Phospho-ERK 1/2 Cryptate (Cisbio) is added to the wells using the Assist Plus and incubated at room temperature overnight in the dark. Plates are read on the Pherastar plate reader at 665 nm and 620 nm wavelengths. $IC_{50}$ determination is performed by fitting the curve of inhibitor percent inhibition versus the log of the inhibitor concentration using the GraphPad Prism 7 software.

Example E: Ras Activation Elisa

The 96-Well Ras Activation ELISA Kit (Cell Biolabs Inc; #STA441) uses the Raf1 RBD (Rho binding domain) bound to a 96-well plate to selectively pull down the active form of Ras from cell lysates. The captured GTP-Ras is then detected by a pan-Ras antibody and HRP-conjugated secondary antibody.

MIA PaCa-2 cells (KRAS G12C; ATCC® CRL-1420) and HPAF-II (KRAS G12D; ATCC® CRL-1997) are maintained in RPMI 1640 with 10% FBS (Gibco/Life Technologies). The cells are seeded into 96 well tissue culture plates (Corning #3596) at 25000 cells per well in 100 uL media and cultured for 2 days at 37° C., 5% $CO_2$ so that they are approximately 80% confluent at the start of the assay. The cells are treated with compounds for either 2 hours or overnight at 37° C., 5% $CO_2$. At the time of harvesting, the cells are washed with PBS, drained well and then lysed with 50 uL of the 1× Lysis buffer (provided by the kit) plus added Halt Protease and Phosphatase inhibitors (1:100) for 1 hour on ice.

The Raf-1 RBD is diluted 1:500 in Assay Diluent (provided in kit) and 100 µL of the diluted Raf-1 RBD is added to each well of the Raf-1 RBD Capture Plate. The plate is covered with a plate sealing film and incubated at room temperature for 1 hour on an orbital shaker. The plate is washed 3 times with 250 µL 1× Wash Buffer per well with thorough aspiration between each wash. 50 µL of Ras lysate sample (10-100 µg) is added per well in duplicate. A "no cell lysate" control is added in a couple of wells for background determination. 50 µL of Assay Diluent is added to all wells immediately to each well and the plate is incubated at room temperature for 1 hour on an orbital shaker. The plate is washed 5 times with 250 µL 1× Wash Buffer per well with thorough aspiration between each wash. 100 µL of the diluted Anti-pan-Ras Antibody is added to each well and the plate is incubated at room temperature for 1 hour on an orbital shaker. The plate is washed 5 times as previously. 100 µL of the diluted Secondary Antibody, HRP Conjugate is added to each well and the plate is incubated at room temperature for 1 hour on an orbital shaker. The plate is washed 5 times as previously and drained well. 100 µL of Chemiluminescent Reagent (provided in the kit) is added to each well, including the blank wells. The plate is incubated at room temperature for 5 minutes on an orbital shaker before the luminescence of each microwell is read on a plate luminometer. The % inhibition is calculated relative to the DMSO control wells after a background level of the "no lysate control" is subtracted from all the values. $IC_{50}$ determination is performed by fitting the curve of inhibitor percent inhibition versus the log of the inhibitor concentration using the GraphPad Prism 7 software.

Example F: Inhibition of RAS-RAF and PI3K-AKT Pathways

The cellular potency of compounds is determined by measuring phosphorylation of KRAS downstream effectors extracellular-signal-regulated kinase (ERK), ribosomal S6 kinase (RSK), AKT (also known as protein kinase B, PKB) and downstream substrate S6 ribosomal protein.

To measure phosphorylated extracellular-signal-regulated kinase (ERK), ribosomal S6 kinase (RSK), AKT and S6 ribosomal protein, cells (details regarding the cell lines and types of data produced are further detailed in Table 4) are seeded overnight in Corning 96-well tissue culture treated plates in RPMI medium with 10% FBS at $4 \times 10^4$ cells/well. The following day, cells are incubated in the presence or absence of a concentration range of test compounds for 4 hours at 37° C., 5% $CO_2$. Cells were washed with PBS and lysed with 1× lysis buffer (Cisbio) with protease and phosphatase inhibitors. 10 μg of total protein lysates are subjected to SDS-PAGE and immunoblot analysis using following antibodies: phospho-ERK1/2-Thr202/Tyr204 (#9101L), total-ERK1/2 (#9102L), phosphor-AKT-Ser473 (#4060L), phospho-p90RSK-Ser380 (#11989S) and phospho-S6 ribosomal protein-Ser235/Ser236 (#2211S) are from Cell Signaling Technologies (Danvers, MA).

TABLE 3

| Cell Line | Histology | KRAS alteration | Readout |
|---|---|---|---|
| H358 | Lung | G12C | pERK, pAKT |
| MIA PaCa-2 | Pancreas | G12C | pERK, pAKT |
| HPAF II | Pancreas | G12D | pERK, pAKT |
| SU.86.86 | Pancreas | G12D | pERK, pAKT |
| PaTu 8988s | Pancreas | G12V | pERK, pAKT |
| H441 | Lung | G12V | pERK, pAKT |

Example G: In Vivo Efficacy Studies

Mia-Paca-2 human pancreatic cancer cells are obtained from the American Type Culture Collection and maintained in RPMI media supplemented with 10% FBS. For efficacy studies experiments, $5 \times 10^6$ Mia-Paca-2 cells are inoculated subcutaneously into the right hind flank of 6- to 8-week-old BALB/c nude mice (Charles River Laboratories, Wilmington, MA, USA). When tumor volumes are approximately 150-250 mm3, mice are randomized by tumor volume and compounds are orally administered. Tumor volume is calculated using the formula $(L \times W^2)/2$, where L and W refer to the length and width dimensions, respectively. Tumor growth inhibition is calculated using the formula $(1-(V_T/V_C)) \times 100$, where $V_T$ is the tumor volume of the treatment group on the last day of treatment, and $V_C$ is the tumor volume of the control group on the last day of treatment. Two-way analysis of variance with Dunnett's multiple comparisons test is used to determine statistical differences between treatment groups (GraphPad Prism). Mice are housed at 10-12 animals per cage, and are provided enrichment and exposed to 12-hour light/dark cycles. Mice whose tumor volumes exceeded limits (10% of body weight) are humanely euthanized by $CO_2$ inhalation. Animals are maintained in a barrier facility fully accredited by the Association for Assessment and Accreditation of Laboratory Animal Care, International. All of the procedures are conducted in accordance with the US Public Service Policy on Human Care and Use of Laboratory Animals and with Incyte Animal Care and Use Committee Guidelines.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:
1. A compound having Formula (I):

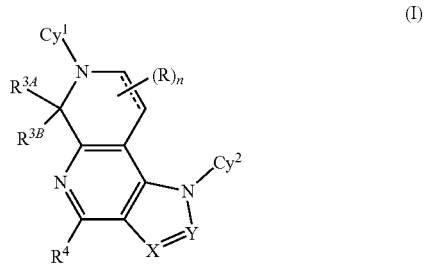

or a pharmaceutically acceptable salt thereof, wherein:
represents a single bond or a double bond;
X is N or $CR^5$;
Y is N or $CR^6$;
each R is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NOR^a)R^b$, $C(=NR^e)NR^cR^d$, $NR^cC(=NR^e)NR^cR^d$, $NR^cC(=NR^e)R^b$, $NR^cS(O)R^b$, $NR^cS(O)_2R^b$, $NR^cS(O)_2NR^cR^d$, $S(O)R^b$, $S(O)NR^cR^d$, $S(O)_2R^b$, $S(O)_2NR^cR^d$, and $BR^hR^i$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;
n is 0, 1, 2, 3, or 4;
$Cy^1$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;
$R^{3A}$ and $R^{3B}$ are each independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)$ OR$^{a3}$, NR$^{c3}$C(O)NR$^{c3}$R$^{d3}$, C(=NR$^{e3}$)R$^{b3}$, C(=NOR$^{a3}$)R$^{b3}$, C(=NR$^{e3}$)NR$^{c3}$R$^{d3}$, NR$^{c3}$C(=NR$^{e3}$)NR$^{c3}$R$^{d3}$, NR$^{c3}$C(=NR$^{e3}$)R$^{b3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, S(O)$_2$NR$^{c3}$R$^{d3}$, and BR$^{h3}$R$^{i3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from R$^{30}$;

or R$^{3A}$ and R$^{3B}$ can be taken together with the carbon atom to which they are attached to form a C=O;

R$^4$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{e4}$)R$^{b4}$, C(=NOR$^{a4}$)R$^{b4}$, C(=NR$^{e4}$)NR$^{c4}$R$^{d4}$, NR$^{c4}$C(=NR$^{e4}$)NR$^{c4}$R$^{d4}$, NR$^{c4}$C(=NR$^{e4}$)R$^{b4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, S(O)$_2$NR$^{c4}$R$^{d4}$, and BR$^{h4}$R$^{i4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from R$^{40}$;

R$^5$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NOR$^{a5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$C(=NR$^{e5}$)R$^{b5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, S(O)$_2$NR$^{c5}$R$^{d5}$, and BR$^{h5}$R$^{i5}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from R$^{50}$;

R$^6$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, NO$_2$, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)OR$^{a6}$, NR$^{c6}$C(O)NR$^{c6}$R$^{d6}$, C(=NR$^{e6}$)R$^{b6}$, C(=NOR$^{a6}$)R$^{b6}$, C(=NR$^{e6}$)NR$^{c6}$R$^{d6}$, NR$^{c6}$C(=NR$^{e6}$)NR$^{c6}$R$^{d6}$, NR$^{c6}$C(=NR$^{e6}$)R$^{b6}$, NR$^{c6}$S(O)R$^{b6}$, NR$^{c6}$S(O)$_2$R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, S(O)$_2$NR$^{c6}$R$^{d6}$, and BR$^{h6}$R$^{i6}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from R$^{60}$;

Cy$^2$ is selected from $C_{3-10}$ cycloalkyl, 4-14 membered heterocycloalkyl, $C_{6-10}$ aryl and 5-10 membered heteroaryl; wherein the 4-14 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-14 membered heterocycloalkyl is optionally substituted by oxo to form a carbonyl group; and wherein the $C_{3-10}$ cycloalkyl, 4-14 membered heterocycloalkyl, $C_{6-10}$ aryl and 5-10 membered heteroaryl are each optionally substituted with 1, 2, 3 or 4 substituents independently selected from R$^{20}$;

each R$^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, NO$_2$, OR$^{a10}$, SR$^{a10}$, C(O)R$^{b10}$, C(O)NR$^{c10}$R$^{d10}$, C(O)OR$^{a10}$, OC(O)R$^{b10}$, OC(O)NR$^{c10}$R$^{d10}$, NR$^{c10}$R$^{d10}$, NR$^{c10}$C(O)R$^{b10}$, NR$^{c10}$C(O)OR$^{a10}$, NR$^{c10}$C(O)NR$^{c10}$R$^{d10}$, C(=NR$^{e10}$)R$^{b10}$, C(=NOR$^{a10}$)R$^{b10}$, C(=NR$^{e10}$)NR$^{c10}$R$^{d10}$ NR$^{c10}$C(=NR$^{e10}$)NR$^{c10}$R$^{d10}$, NR$^{c10}$S(O)R$^{b10}$, NR$^{c10}$S(O)$_2$R$^{b10}$, NR$^{c10}$S(O)$_2$NR$^{c10}$R$^{d10}$S(O)R$^{b10}$, S(O)NR$^{c10}$R$^{d10}$, S(O)$_2$R$^{b10}$, S(O)$_2$NR$^{c10}$R$^{d10}$, and BR$^{h10}$R$^{i10}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from R$^{11}$;

each R$^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$alkylene, halo, D, CN, OR$^{a11}$, SR$^{a11}$, C(O)R$^{b11}$, C(O)NR$^{c11}$R$^{d11}$, C(O)OR$^{a11}$, OC(O)R$^{b11}$, OC(O)NR$^{c11}$R$^{d11}$, NR$^{c11}$R$^{d11}$, NR$^{c11}$C(O)R$^{b11}$, NR$^{c11}$C(O)OR$^{a11}$, NR$^{c11}$C(O)NR$^{c11}$R$^{d11}$, NR$^{c11}$S(O)R$^{b11}$, NR$^{c11}$S(O)$_2$R$^{b11}$, NR$^{c11}$S(O)$_2$NR$^{c11}$R$^{d11}$, S(O)R$^{b11}$, S(O)NR$^{c11}$R$^{d11}$, S(O)$_2$R$^{b11}$, S(O)$_2$NR$^{c11}$R$^{d11}$, and BR$^{h11}$R$^{i11}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from R$^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a12}$, $SR^{a12}$, $C(O)R^{b12}$, $C(O)NR^{c12}R^{d12}$, $C(O)OR^{a12}$, $O(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$, and $BR^{h12}R^{i12}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a20}$, $SR^{a20}$, $C(O)R^{b20}$, $C(O)NR^{c20}R^{d20}$, $C(O)OR^{a20}$, $OC(O)R^{b20}$, $OC(O)NR^{c20}R^{d20}$, $NR^{c20}R^{d20}$, $NR^{c20}C(O)R^{b20}$, $OC(O)OR^{a20}$, $NR^{c20}C(O)NR^{c20}R^{d20}$, $C(=NR^{e20})R^{b20}$, $C(=NOR^{a20})R^{b20}$, $C(=NR^{e20})NR^{c20}R^{d20}$, $NR^{c20}C(=NR^{e20})NR^{c20}R^{d20}$, $NR^{c20}S(O)R^{b20}$, $NR^{c20}S(O)_2R^{b20}$, $NR^{c20}S(O)_2NR^{c20}R^{d20}$, $S(O)R^{b20}$, $S(O)NR^{c20}R^{d20}$, $S(O)_2R^{b20}$, $S(O)_2NR^{c20}R^{d20}$, and $BR^{h20}R^{i20}$; wherein said $C_{1-6}$ alkyl, $C_{2-6}$ alkenyl, $C_{2-6}$ alkynyl, $C_{3-10}$ cycloalkyl, 4-10 membered heterocycloalkyl, O6-10 aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$alkylene, halo, D, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, and $BR^{h21}R^{i21}$; wherein said $C_{1-6}$ alkyl, $C_{2-6}$ alkenyl, $C_{2-6}$ alkynyl, $C_{3-10}$ cycloalkyl, 4-10 membered heterocycloalkyl, O6-10 aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^g$;

each $R^{22}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$alkylene, halo, D, CN, $NO_2$, $OR^{a22}$, $SR^{a22}$, $C(O)R^{b22}$, $C(O)NR^{c22}R^{d22}$, $C(O)OR^{a22}$, $OC(O)R^{b22}$, $OC(O)NR^{c22}R^{d22}$, $NR^{c22}R^{d22}$, $NR^{c22}C(O)R^{b22}$, $NR^{c22}C(O)OR^{a22}$, $NR^{c22}C(O)NR^{c22}R^{d22}$, $NR^{c22}S(O)R^{b22}$, $NR^{c22}S(O)_2R^{b22}$, $NR^{c22}S(O)_2NR^{c22}R^{d22}$ $S(O)R^{b22}$, $S(O)NR^{c22}R^{d22}$, $S(O)_2R^{b22}$, $S(O)_2NR^{c22}R^{d22}$, and $BR^{h22}R^{i22}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{23}$;

each $R^{23}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$alkylene, halo, D, CN, $OR^{a23}$, $SR^{a23}$, $C(O)R^{b23}$, $C(O)NR^{c23}R^{d23}$, $C(O)OR^{a23}$, $OC(O)R^{b23}$, $OC(O)NR^{c23}R^{d23}$, $NR^{c23}R^{d23}$, $NR^{c23}C(O)R^{b23}$, $NR^{c23}C(O)OR^{a23}$, $NR^{c23}C(O)NR^{c23}R^{d23}$, $NR^{c23}S(O)R^{b23}$, $NR^{c23}S(O)_2R^{b23}$, $NR^{c23}S(O)_2NR^{c23}R^{d23}$ $S(O)R^{b23}$, $S(O)NR^{c23}R^{d23}$, $S(O)_2R^{b23}$, $S(O)_2NR^{c23}R^{d23}$, and $BR^{h23}R^{i23}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{24}$;

each $R^{24}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a24}$, $SR^{a24}$, $C(O)R^{b24}$, $C(O)NR^{c24}R^{d24}$, $C(O)OR^{a24}$, $OC(O)R^{b24}$, $OC(O)NR^{c24}R^{d24}$, $NR^{c24}R^{d24}$, $NR^{c24}C(O)R^{b24}$, $NR^{c24}C(O)OR^{a24}$, $NR^{c24}C(O)NR^{c24}R^{d24}$, $NR^{c24}S(O)R^{b24}$, $NR^{c24}S(O)_2R^{b24}$, $NR^{c24}S(O)_2NR^{c24}R^{d24}$, $S(O)R^{b24}$, $S(O)NR^{c24}R^{d24}$, $S(O)_2R^{b24}$, $S(O)_2NR^{c24}R^{d24}$, and $BR^{h24}R^{i24}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{30}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$alkylene, halo, D, CN, $NO_2$, $OR^{a30}$, $SR^{a30}$, $C(O)R^{b30}$, $C(O)NR^{c30}R^{d30}$, $C(O)OR^{a30}$, $OC(O)R^{b30}$, $OC(O)NR^{c30}R^{d30}$, $NR^{c30}R^{d30}$, $NR^{c30}C(O)R^{b30}$, $NR^{c30}C(O)OR^{a30}$, $NR^{c30}C(O)NR^{c30}R^{d30}$, $NR^{c30}S(O)R^{b30}$, $NR^{c30}S(O)_2R^{b30}$, $NR^{c30}S(O)_2NR^{c30}R^{d30}$, $S(O)R^{b30}$, $S(O)NR^{c30}R^{d30}$, $S(O)_2R^{b30}$, $S(O)_2NR^{c30}R^{d30}$, and $BR^{h30}R^{i30}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{31}$;

each $R^{31}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)OR^{a31}$, $NR^{c31}C(O)NR^{c31}R^{d31}$, $NR^{c31}S(O)R^{b31}$, $NR^{c31}S(O)_2R^{b31}$, $NR^{c31}S(O)_2NR^{c31}R^{d31}$, $S(O)R^{b31}$, $S(O)NR^{c31}R^{d31}$, $S(O)_2R^{b31}$, $S(O)_2NR^{c31}R^{d31}$, and $BR^{h31}R^{i31}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{32}$;

each $R^{32}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a32}$, $SR^{a32}$, $C(O)R^{b32}$, $C(O)NR^{c32}R^{d32}$, $C(O)OR^{a32}$, $OC(O)R^{b32}$, $OC(O)NR^{c32}R^{d32}$, $NR^{32}R^{d32}$, $NR^{32}C(O)R^{b32}$, $NR^{c32}C(O)OR^{a32}$, $NR^{c32}C(O)NR^{c32}R^{d32}$, $NR^{c32}S(O)R^{b32}$, $NR^{c32}S(O)_2R^{b32}$, $NR^{c32}S(O)_2NR^{c32}R^{d32}$, $S(O)R^{b32}$, $S(O)NR^{c32}R^{d32}$, $S(O)_2R^{b32}$, $S(O)_2NR^{c32}R^{d32}$, and $BR^{h32}R^{i32}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{40}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a40}$, $SR^{a40}$, $C(O)R^{b40}$, $C(O)NR^{c40}R^{d40}$, $C(O)OR^{a40}$, $OC(O)R^{b40}$, $OC(O)NR^{c40}R^{d40}$, $NR^{c40}R^{d40}$, $NR^{c40}C(O)R^{b40}$, $NR^{c40}C(O)OR^{a40}$, $NR^{c40}C(O)NR^{c40}R^{d40}$, $NR^{c40}S(O)R^{b40}$, $NR^{c40}S(O)_2R^{b40}$, $NR^{c40}S(O)_2NR^{c40}R^{d40}$, $S(O)R^{b40}$, $S(O)NR^{c40}R^{d40}$, $S(O)_2R^{b40}$, $S(O)_2NR^{c40}R^{d40}$, and $BR^{h40}R^{i40}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{41}$;

each $R^{41}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d41}$, $NR^{c41}S(O)R^{b41}$, $NR^{c41}S(O)_2R^{b41}$, $NR^{c41}S(O)_2NR^{c41}R^{d41}$, $S(O)R^{b41}$, $S(O)NR^{c41}R^{d41}$, $S(O)_2R^{b41}$, $S(O)_2NR^{c41}R^{d41}$, and $BR^{h41}R^{i41}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{42}$;

each $R^{42}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a42}$, $SR^{a42}$, $C(O)R^{b42}$, $C(O)NR^{c42}R^{d42}$, $C(O)OR^{a42}$, $OC(O)R^{b42}$, $OC(O)NR^{c42}R^{d42}$, $NR^{c42}R^{d42}$, $NR^{c42}C(O)R^{b42}$, $NR^{c42}C(O)OR^{a42}$, $NR^{c42}C(O)NR^{c42}R^{d42}$, $NR^{c42}S(O)R^{b42}$, $NR^{c42}S(O)_2R^{b42}$, $NR^{c42}S(O)_2NR^{c42}R^{d42}$, $S(O)R^{b42}$, $S(O)NR^{c42}R^{d42}$, $S(O)_2R^{b42}$, $S(O)_2NR^{c42}R^{d42}$, and $BR^{h42}R^{i42}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{50}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a50}$, $SR^{a50}$, $C(O)R^{b50}$, $C(O)NR^{c50}R^{d50}$, $C(O)OR^{a50}$, $OC(O)R^{b50}$, $OC(O)NR^{c50}R^{d50}$, $NR^{c50}R^{d50}$, $NR^{c50}C(O)R^{b50}$, $NR^{c50}C(O)OR^{a50}$, $NR^{c50}C(O)NR^{c50}R^{d50}$, $NR^{c50}S(O)R^{b50}$, $NR^{c50}S(O)_2R^{b50}$, $NR^{c50}S(O)_2NR^{c50}R^{d50}$, $S(O)R^{b50}$, $S(O)NR^{c50}R^{d50}$, $S(O)_2R^{b50}$, $S(O)_2NR^{c50}R^{d50}$, and $BR^{h50}R^{i50}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{51}$;

each $R^{51}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a51}$, $SR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, and $BR^{h51}R^{i51}$; wherein said $C_{1-6}$ alkyl, $C_{2-6}$ alkenyl, $C_{2-6}$ alkynyl, $C_{3-6}$ cycloalkyl, $C_{6-10}$ aryl, 5-6 membered heteroaryl and 4-7 membered heterocycloalkyl, are each optionally substituted with 1, 2, 3, or 4 substituents independently selected from $R^{52}$;

each $R^{52}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a52}$, $SR^{a52}$, $C(O)R^{b52}$, $C(O)NR^{c52}R^{d52}$, $C(O)OR^{a52}$, $C(O)R^{b52}$, $OC(O)NR^{c52}R^{d52}$, $NR^{c52}R^{d52}$, $NR^{c52}C(O)R^{b52}$, $NR^{c52}C(O)OR^{a52}$, $NR^{c52}C(O)NR^{c52}R^{d52}$, $NR^{c52}S(O)R^{b52}$, $NR^{c52}S(O)_2R^{b52}$, $NR^{c52}S(O)_2NR^{c52}R^{d52}$, $S(O)R^{b52}$, $S(O)NR^{c52}R^{d52}$, $S(O)_2R^{b52}$, $S(O)_2NR^{c52}R^{d52}$, and $BR^{h52}R^{i52}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^{60}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$alkylene, halo, D, CN, $NO_2$, $OR^{a60}$, $SR^{a60}$, $C(O)R^{b60}$, $C(O)NR^{c60}R^{d60}$, $C(O)OR^{a60}$, $OC(O)R^{b60}$, $OC(O)NR^{c60}R^{d60}$, $NR^{c60}R^{d60}$, $NR^{c60}C(O)R^{b60}$, $NR^{c60}C(O)OR^{a60}$, $NR^{c60}C(O)NR^{c60}R^{d60}$, $NR^{c60}S(O)R^{b60}$, $NR^{c60}S(O)_2R^{b60}$, $NR^{c60}S(O)_2NR^{c60}R^{d60}$, $S(O)R^{b60}$, $S(O)NR^{c60}R^{d60}$, $S(O)_2R^{b60}$, $S(O)_2NR^{c60}R^{d60}$, and $BR^{h60}R^{i60}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{61}$;

each $R^{61}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$alkylene, halo, D, CN, $OR^{a61}$, $SR^{a61}$, $C(O)R^{b61}$, $C(O)NR^{c61}R^{d61}$, $C(O)OR^{a61}$, $OC(O)R^{b61}$, $OC(O)NR^{c61}R^{d61}$, $NR^{c61}R^{d61}$, $NR^{c61}C(O)R^{b61}$, $NR^{c61}C(O)OR^{a61}$, $NR^{c61}C(O)NR^{c61}R^{d61}$, $NR^{c61}S(O)R^{b61}$, $NR^{c61}S(O)_2R^{b61}$, $NR^{c61}S(O)_2NR^{c61}R^{d61}S(O)R^{b61}$, $S(O)NR^{c61}R^{d61}$, $S(O)_2R^{b61}$, $S(O)_2NR^{c61}R^{d61}$, and $BR^{h61}R^{i61}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $O6-10$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{62}$;

each $R^{62}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a62}$, $SR^{a62}$, $C(O)R^{b62}$, $C(O)NR^{c62}R^{d62}$, $C(O)OR^{a62}$, $OC(O)R^{b62}$, $OC(O)NR^{c62}R^{d62}$, $NR^{c62}R^{d62}$, $NR^{c62}C(O)R^{b62}$, $NR^{c62}C(O)OR^{a62}$, $NR^{c62}C(O)NR^{c62}R^{d62}$, $NR^{c62}S(O)R^{b62}$, $NR^{c62}S(O)_2R^{b62}$, $NR^{c62}S(O)_2NR^{c62}R^{d62}$, $S(O)R^{b62}$, $S(O)NR^{c62}R^{d62}$, $S(O)_2R^{b62}$, $S(O)_2NR^{c62}R^{d62}$, and $BR^{h62}R^{i62}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^g$;

each $R^a$, $R^b$, $R^c$ and $R^d$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{22}$;

or any $R^c$ and $R^d$ attached to the same N atom, together with the N atom to which they are attached, form a 4-, 5-, 6- or 7-membered heterocycloalkyl group optionally substituted with 1, 2, 3, or 4 substituents independently selected from $R^{22}$;

each $R^e$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^h$ and $R^i$ is independently selected from OH, $C_{1-6}$ alkoxy, and $C_{1-6}$ haloalkoxy; or any $R^h$ and $R^i$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a3}$, $R^{b3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{30}$;

or any $R^{c3}$ and $R^{d3}$ attached to the same N atom, together with the N atom to which they are attached, form a 4-, 5-, 6- or 7-membered heterocycloalkyl group optionally substituted with 1, 2, 3, or 4 substituents independently selected from $R^{30}$;

each $R^{e3}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h3}$ and $R^{i3}$ is independently selected from OH, $C_{1-6}$ alkoxy, and $C_{1-6}$ haloalkoxy; or any $R^{h3}$ and $R^{i3}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a4}$, $R^{b4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c4}$ and $R^{d4}$ attached to the same N atom, together with the N atom to which they are attached, form a 4-, 5-, 6- or 7-membered heterocycloalkyl group optionally substituted with 1, 2, 3, or 4 substituents independently selected from $R^{40}$;

each $R^{e4}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h4}$ and $R^4$ is independently selected from OH, $C_{1-6}$ alkoxy, and $C_{1-6}$ haloalkoxy; or any $R^{h4}$ and $R^{i4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{j4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c4}$ and $R^{j4}$ attached to the same N atom, together with the N atom to which they are attached, form a 4-, 5-, 6- or 7-membered heterocycloalkyl group optionally substituted with 1, 2, 3, or 4 substituents independently selected from $R^{40}$;

each $R^{a5}$, $R^{b5}$, $R^{c5}$, and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{50}$;

or any $R^{c5}$ and $R^{d5}$ attached to the same N atom, together with the N atom to which they are attached, form a 4-, 5-, 6- or 7-membered heterocycloalkyl group optionally substituted with 1, 2 or 3 substituents independently selected from $R^{50}$;

each $R^{e5}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h5}$ and $R^{i5}$ is independently selected from OH, $C_{1-6}$ alkoxy, and $C_{1-6}$ haloalkoxy; or any $R^{h5}$ and $R^{i5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a6}$, $R^{b6}$, $R^{c6}$, and $R^{d6}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^{60}$;

each $R^{e6}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h6}$ and $R^{i6}$ is independently selected from OH, $C_{1-6}$ alkoxy, and $C_{1-6}$ haloalkoxy; or any $R^{h6}$ and $R^{i6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a10}$, $R^{b10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

or any $R^{c10}$ and $R^{d10}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{e10}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h10}$ and $R^{i10}$ is independently selected from OH, $C_{1-6}$ alkoxy, and $C_{1-6}$ haloalkoxy; or any $R^{h10}$ and $R^{i10}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a11}$, $R^{b11}$, $R^{c11}$ and $R^{d11}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

or any $R^{c11}$ and $R^{d11}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{h11}$ and $R^{i11}$ is independently selected from OH, $C_{1-6}$ alkoxy, and $C_{1-6}$ haloalkoxy; or any $R^{h11}$ and $R^{i11}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a12}$, $R^{b12}$, $R^{c12}$ and $R^{d12}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{h12}$ and $R^{i12}$ is independently selected from OH, $C_{1-6}$ alkoxy, and $C_{1-6}$ haloalkoxy; or any $R^{h12}$ and $R^{i12}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a20}$, $R^{b20}$, $R^{c20}$ and $R^{d20}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{21}$;

or any $R^{c20}$ and $R^{d20}$ attached to the same N atom, together with the N atom to which they are attached, form a 4-, 5-, 6- or 7-membered heterocycloalkyl group optionally substituted with 1, 2, 3, or 4 substituents independently selected from $R^{21}$;

each $R^{e20}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h20}$ and $R^{i20}$ is independently selected from OH, $C_{1-6}$ alkoxy, and $C_{1-6}$ haloalkoxy; or any $R^{h20}$ and $R^{i20}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a21}$, $R^{b21}$, $R^{c21}$ and $R^{d21}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

or any $R^{c21}$ and $R^{d21}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{h21}$ and $R^{i21}$ is independently selected from OH, $C_{1-6}$ alkoxy, and $C_{1-6}$ haloalkoxy; or any $R^{h21}$ and $R^{i21}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a22}$, $R^{b22}$, $R^{c22}$ and $R^{d22}$ is independently selected from H, $C_{1-6}$ alkyl, $C_{2-6}$ alkenyl, $C_{2-6}$ alkynyl, $C_{1-6}$ haloalkyl, $C_{3-10}$cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{23}$;

or any $R^{c22}$ and $R^{d22}$ attached to the same N atom, together with the N atom to which they are attached, form a 4-, 5-, 6- or 7-membered heterocycloalkyl group optionally substituted with 1, 2, 3, or 4 substituents independently selected from $R^{23}$;

each $R^{h22}$ and $R^{i22}$ is independently selected from OH, $C_{1-6}$ alkoxy, and $C_{1-6}$ haloalkoxy; or any $R^{h22}$ and $R^{i22}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a23}$, $R^{b23}$, $R^{c23}$ and $R^{d23}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$cycloalkyl, phenyl, 5-6 membered heteroaryl and 4-7 membered heterocycloalkyl are each optionally substituted with 1, 2, 3, or 4 substituents independently selected from $R^{24}$;

or any $R^{c23}$ and $R^{d23}$ attached to the same N atom, together with the N atom to which they are attached, form a 4-, 5-, 6- or 7-membered heterocycloalkyl group optionally substituted with 1, 2 or 3 substituents independently selected from $R^{24}$;

each $R^{h23}$ and $R^{i23}$ is independently selected from OH, $C_{1-6}$ alkoxy, and $C_{1-6}$ haloalkoxy; or any $R^{h23}$ and $R^{i23}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a24}$, $R^{b24}$, $R^{c24}$ and $R^{d24}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{h24}$ and $R^{i24}$ is independently selected from OH, $C_{1-6}$ alkoxy, and $C_{1-6}$ haloalkoxy; or any $R^{h24}$ and $R^{i24}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a30}$, $R^{b30}$, $R^{c30}$ and $R^{d30}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{31}$;

or any $R^{c30}$ and $R^{d30}$ attached to the same N atom, together with the N atom to which they are attached, form a 4-, 5-, 6- or 7-membered heterocycloalkyl group optionally substituted with 1, 2, 3, or 4 substituents independently selected from $R^{31}$;

each $R^{h30}$ and $R^{i30}$ is independently selected from OH, $C_{1-6}$ alkoxy, and $C_{1-6}$ haloalkoxy; or any $R^{h30}$ and $R^{i30}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a31}$, $R^{b31}$, $R^{c31}$ and $R^{d31}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$cycloalkyl, phenyl, 5-6 membered heteroaryl and 4-7 membered heterocycloalkyl are each optionally substituted with 1, 2, 3, or 4 substituents independently selected from $R^{32}$;

or any $R^{c31}$ and $R^{d31}$ attached to the same N atom, together with the N atom to which they are attached, form a 4-, 5-, 6- or 7-membered heterocycloalkyl group optionally substituted with 1, 2 or 3 substituents independently selected from $R^{32}$;

each $R^{h31}$ and $R^{i31}$ is independently selected from OH, $C_{1-6}$ alkoxy, and $C_{1-6}$ haloalkoxy; or any $R^{h31}$ and $R^{i31}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a32}$, $R^{b32}$, $R^{c32}$ and $R^{d32}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c32}$ and $R^{d32}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{h32}$ and $R^{i32}$ is independently selected from OH, $C_{1-6}$ alkoxy, and $C_{1-6}$ haloalkoxy; or any $R^{h32}$ and $R^{i32}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a40}$, $R^{b40}$, $R^{c40}$ and $R^{d40}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{41}$;

or any $R^{c40}$ and $R^{d40}$ attached to the same N atom, together with the N atom to which they are attached, form a 4-, 5-, 6- or 7-membered heterocycloalkyl group optionally substituted with 1, 2, 3, or 4 substituents independently selected from $R^{41}$;

each $R^{h40}$ and $R^{i40}$ is independently selected from OH, $C_{1-6}$ alkoxy, and $C_{1-6}$ haloalkoxy; or any $R^{h40}$ and $R^{i40}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a41}$, $R^{b41}$, $R^{c41}$ and $R^{d41}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{42}$;

or any $R^{c41}$ and $R^{d41}$ attached to the same N atom, together with the N atom to which they are attached, form a 4-, 5-, 6- or 7-membered heterocycloalkyl group optionally substituted with 1, 2 or 3 substituents independently selected from $R^{42}$;

each $R^{h41}$ and $R^{i41}$ is independently selected from OH, $C_{1-6}$ alkoxy, and $C_{1-6}$ haloalkoxy; or any $R^{h41}$ and $R^{i41}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a42}$, $R^{b42}$, $R^{c42}$ and $R^{d42}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c42}$ and $R^{d42}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{h42}$ and $R^{i42}$ is independently selected from OH, $C_{1-6}$ alkoxy, and $C_{1-6}$ haloalkoxy; or any $R^{h42}$ and $R^{i42}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a50}$, $R^{b50}$, $R^{c50}$ and $R^{d50}$, is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{51}$;

or any $R^{c50}$ and $R^{d50}$ attached to the same N atom, together with the N atom to which they are attached, form a 4-, 5-, 6- or 7-membered heterocycloalkyl group optionally substituted with 1, 2 or 3 substituents independently selected from $R^{51}$;

each $R^{h50}$ and $R^{i50}$ is independently selected from OH, $C_{1-6}$ alkoxy, and $C_{1-6}$ haloalkoxy; or any $R^{h50}$ and $R^{i50}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a51}$, $R^{b51}$, $R^{c51}$ and $R^{d51}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{52}$;

or any $R^{c51}$ and $R^{d51}$ attached to the same N atom, together with the N atom to which they are attached, form a 4-, 5-, 6- or 7-membered heterocycloalkyl group optionally substituted with 1, 2, 3, or 4 substituents independently selected from $R^{52}$;

each $R^{h51}$ and $R^{i51}$ is independently selected from OH, $C_{1-6}$ alkoxy, and $C_{1-6}$ haloalkoxy; or any $R^{h51}$ and $R^{i51}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a52}$, $R^{b52}$, $R^{c52}$ and $R^{d52}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c52}$ and $R^{d52}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{h52}$ and $R^{i52}$ is independently selected from OH, $C_{1-6}$ alkoxy, and $C_{1-6}$ haloalkoxy; or any $R^{h52}$ and $R^{i52}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a60}$, $R^{b60}$, $R^{c60}$ and $R^{d60}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$cycloalkyl, 4-10 membered heterocycloalkyl, $C_{6-10}$ aryl and 5-10 membered heteroaryl, are each optionally substituted with 1, 2, 3, or 4 substituents independently selected from $R^{61}$;

or any $R^{c60}$ and $R^{d60}$ attached to the same N atom, together with the N atom to which they are attached, form a 4-, 5-, 6- or 7-membered heterocycloalkyl group optionally substituted with 1, 2, 3, or 4 substituents independently selected from $R^{61}$;

each $R^{h60}$ and $R^{i60}$ is independently selected from OH, $C_{1-6}$ alkoxy, and $C_{1-6}$ haloalkoxy; or any $R^{h60}$ and $R^{i60}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a61}$, $R^{b61}$, $R^{c61}$ and $R^{d61}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$cycloalkyl, phenyl, 5-6 membered heteroaryl and 4-7 membered heterocycloalkyl are each optionally substituted with 1, 2, 3, or 4 substituents independently selected from $R^{62}$;

or any $R^{c61}$ and $R^{d61}$ attached to the same N atom, together with the N atom to which they are attached, form a 4-, 5-, 6- or 7-membered heterocycloalkyl group optionally substituted with 1, 2 or 3 substituents independently selected from $R^{62}$;

each $R^{h61}$ and $R^{i61}$ is independently selected from OH, $C_{1-6}$ alkoxy, and $C_{1-6}$ haloalkoxy; or any $R^{h61}$ and $R^{i61}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a62}$, $R^{b62}$, $R^{c62}$ and $R^{d62}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c62}$ and $R^{d62}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{h62}$ and $R^{i62}$ is independently selected from OH, $C_{1-6}$ alkoxy, and $C_{1-6}$ haloalkoxy; or any $R^{h62}$ and $R^{i62}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^g$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The compound of claim 1, or pharmaceutically acceptable salt thereof, wherein ═══ represents a single bond or a double bond;

X is N or $CR^5$;

Y is N or $CR^6$;

each R is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NOR^a)R^b$, $C(=NR^e)NR^cR^d$, $NR^cC(=NR^e)NR^cR^d$, $NR^cC(=NR^e)R^b$, $NR^cS(O)R^b$, $NR^cS(O)_2R^b$, $NR^cS(O)_2NR^cR^d$, $S(O)R^b$, $S(O)NR^cR^d$, $S(O)_2R^b$, $S(O)_2NR^cR^d$, and $BR^hR^i$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

n is 0, 1, 2, 3, or 4;

$Cy^1$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

$R^{3A}$ and $R^{3B}$ are each independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NOR$^{a3}$)R$^{b3}$, C(=NR$^{e3}$)NR$^{c3}$R$^{d3}$, NR$^{c3}$C(=NR$^{e3}$)NR$^{c3}$R$^{d3}$, NR$^{c3}$C(=NR$^{e3}$)R$^{b3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, S(O)$_2$NR$^{c3}$R$^{d3}$, and BR$^{h3}$R$^{i3}$; or R$^{3A}$ and R$^{3B}$ can be taken together with the carbon atom to which they are attached to form a C=O;

R$^4$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{e4}$)R$^{b4}$, C(=NOR$^{a4}$)R$^{b4}$, C(=NR$^{e4}$)NR$^{c4}$R$^{d4}$, NR$^{c4}$C(=NR$^{e4}$)NR$^{c4}$R$^{d4}$, NR$^{c4}$C(=NR$^{e4}$)R$^{b4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, S(O)$_2$NR$^{c4}$R$^{d4}$, and BR$^{h4}$R$^{i4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from R$^{40}$;

R$^5$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{1-3}$ aryl-$C_{1-3}$ alkylene, 5-10 membered heteroaryl-$C_{1-3}$ alkylene, halo, D, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NOR$^{a5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$C(=NR$^{e5}$)R$^{b5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, S(O)$_2$NR$^{c5}$R$^{d5}$, and BR$^{h5}$R$^{i5}$;

R$^6$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, NO$_2$, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)OR$^{a6}$, NR$^{c6}$C(O)NR$^{c6}$R$^{d6}$, C(=NR$^{e6}$)R$^{b6}$, C(=NOR$^{a6}$)R$^{b6}$, C(=NR$^{e6}$)NR$^{c6}$R$^{d6}$, NR$^{c6}$C(=NR$^{e6}$)NR$^{c6}$R$^{d6}$, NR$^{c6}$C(=NR$^{e6}$)R$^{b6}$, NR$^{c6}$S(O)R$^{b6}$, NR$^{c6}$S(O)$_2$R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, S(O)$_2$NR$^{c6}$R$^{d6}$, and BR$^{h6}$R$^{i6}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from R$^{60}$;

Cy$^2$ is selected from $C_{3-10}$ cycloalkyl, 4-14 membered heterocycloalkyl, $C_{6-10}$ aryl and 5-10 membered heteroaryl; wherein the 4-14 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-14 membered heterocycloalkyl is optionally substituted by oxo to form a carbonyl group; and wherein the $C_{3-10}$ cycloalkyl, 4-14 membered heterocycloalkyl, $C_{6-10}$ aryl and 5-10 membered heteroaryl are each optionally substituted with 1, 2, 3 or 4 substituents independently selected from R$^{20}$;

each R$^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{13}$alkylene, halo, D, CN, NO$_2$, OR$^{a10}$, SR$^{a10}$, C(O)R$^{b10}$, C(O)NR$^{c10}$R$^{d10}$, C(O)OR$^{a10}$, OC(O)R$^{b10}$, OC(O)NR$^{c10}$R$^{d10}$, NR$^{c10}$R$^{d10}$, NR$^{c10}$C(O)R$^{b10}$, NR$^{c10}$C(O)OR$^{a10}$, NR$^{c10}$C(O)NR$^{c10}$R$^{d10}$, C(=NR$^{e10}$)R$^{b10}$, C(=NOR$^{a10}$)R$^{b10}$, C(=NR$^{e10}$)NR$^{c10}$R$^{d10}$, NR$^{c10}$C(=NR$^{e10}$)NR$^{c10}$R$^{d10}$, NR$^{c10}$S(O)R$^{b10}$, NR$^{c10}$S(O)$_2$R$^{b10}$, NR$^{c10}$S(O)$_2$NR$^{c10}$R$^{d10}$, S(O)R$^{b10}$, S(O)NR$^{c10}$R$^{d10}$, S(O)$_2$R$^{b10}$, S(O)$_2$NR$^{c10}$R$^{d10}$, and BR$^{h10}$R$^{i10}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{13}$alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from R$^{11}$;

each R$^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{13}$alkylene, halo, D, CN, OR$^{a11}$, SR$^{a11}$, C(O)R$^{b11}$, C(O)NR$^{c11}$R$^{d11}$, C(O)OR$^{a11}$, OC(O)R$^{b11}$, OC(O)NR$^{c11}$R$^{d11}$, NR$^{c11}$R$^{d11}$, NR$^{c11}$C(O)R$^{b11}$, NR$^{c11}$C(O)OR$^{a11}$, NR$^{c11}$C(O)NR$^{c11}$R$^{d11}$, NR$^{c11}$S(O)R$^{b11}$, NR$^{c11}$S(O)$_2$R$^{b11}$, NR$^{c11}$S(O)$_2$NR$^{c11}$R$^{d11}$, S(O)R$^{b11}$, S(O)NR$^{c11}$R$^{d11}$, S(O)$_2$R$^{b11}$, S(O)$_2$NR$^{c11}$R$^{d11}$, and BR$^{h11}$R$^{i11}$;

each R$^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{13}$alkylene, halo, D, CN, NO$_2$, OR$^{a20}$, SR$^{a20}$, C(O)R$^{b20}$, C(O)NR$^{c20}$R$^{d20}$, C(O)OR$^{a20}$, OC(O)R$^{b20}$, OC(O)NR$^{c20}$R$^{d20}$, NR$^{c20}$R$^{d20}$, NR$^{c20}$C(O)R$^{b20}$, NR$^{c20}$C(O)OR$^{a20}$, NR$^{c20}$C(O)NR$^{c20}$R$^{d20}$, C(=NR$^{e20}$)R$^{b20}$, C(=NOR$^{a20}$)R$^{b20}$, C(=NR$^{e20}$)NR$^{c20}$R$^{d20}$, NR$^{c20}$C(=NR$^{e20}$)NR$^{c20}$R$^{d20}$, NR$^{c20}$S(O)R$^{b20}$, NR$^{c20}$S(O)$_2$R$^{b20}$, NR$^{c2}$S(O)$_2$NR$^{c20}$R$^{d20}$, S(O)R$^{b20}$, S(O)NR$^{c20}$R$^{d20}$, S(O)$_2$R$^{b20}$, S(O)$_2$NR$^{c20}$R$^{d20}$, and BR$^{h20}$R$^{i20}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from R$^{21}$;

each R$^{21}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{13}$alkylene, halo, D, CN, OR$^{a21}$, SR$^{a21}$, C(O)R$^{b21}$, C(O)NR$^{c21}$R$^{d21}$, C(O)OR$^{a21}$, OC(O)R$^{b21}$, OC(O)NR$^{c21}$R$^{d21}$, NR$^{c21}$R$^{d21}$, NR$^{c21}$C(O)R$^{b21}$, NR$^{c21}$C(O)OR$^{a21}$, NR$^{c21}$C(O)NR$^{c21}$R$^{d21}$, NR$^{c21}$S(O)R$^{b21}$, NR$^{c21}$S(O)$_2$R$^{b21}$, NR$^{c21}$S(O)$_2$NR$^{c21}$R$^{d21}$, S(O)R$^{b21}$, S(O)NR$^{c21}$R$^{d21}$, S(O)$_2$R$^{b21}$, S(O)$_2$NR$^{c21}$R$^{d21}$, and BR$^{h21}$R$^{i21}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from R$^g$;

each R$^{22}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$ alkylene, halo, D, CN, NO$_2$, OR$^{a22}$, SR$^{a22}$, C(O)R$^{b22}$, C(O)NR$^{c22}$R$^{d22}$, C(O)OR$^{a22}$, OC(O)R$^{b22}$, OC(O)NR$^{c22}$R$^{d22}$, NR$^{c22}$R$^{d22}$, NR$^{c22}$C(O)R$^{b22}$, NR$^{c22}$C(O)OR$^{a22}$, NR$^{c22}$C(O)NR$^{c22}$R$^{d22}$, NR$^{c22}$S(O)R$^{b22}$, NR$^{c22}$S(O)$_2$R$^{b22}$, NR$^{c22}$S(O)$_2$NR$^{c22}$R$^{d22}$, S(O)R$^{b22}$, S(O)NR$^{c22}$R$^{d22}$, S(O)$_2$R$^{b22}$, S(O)$_2$NR$^{c22}$R$^{d22}$, and BR$^{h22}$R$^{i22}$;

each R$^{40}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{13}$alkylene, halo, D, CN, NO$_2$, OR$^{a40}$, SR$^{a40}$, C(O)R$^{b40}$, C(O)NR$^{c40}$R$^{d40}$, C(O)OR$^{a40}$, OC(O)R$^{b40}$, OC(O)NR$^{c40}$R$^{d40}$, NR$^{c40}$R$^{d40}$, NR$^{c40}$C(O)R$^{b40}$, NR$^{c40}$C(O)OR$^{a40}$, NR$^{c40}$C(O)NR$^{c40}$R$^{d40}$, NR$^{c40}$S(O)R$^{b40}$, NR$^{c40}$S(O)$_2$R$^{b40}$, NR$^{c40}$S(O)$_2$NR$^{c40}$R$^{d40}$, S(O)R$^{b40}$, S(O)NR$^{c40}$R$^{d40}$, S(O)$_2$R$^{b40}$, S(O)$_2$NR$^{c40}$R$^{d40}$, and BR$^{h40}$R$^{i40}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from R$^{41}$;

each R$^{41}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$ alkylene, halo, D, CN, OR$^{a41}$, SR$^{a41}$, C(O)R$^{b41}$, C(O)NR$^{c41}$R$^{d41}$, C(O)OR$^{a41}$, OC(O)R$^{b41}$, OC(O)NR$^{c41}$R$^{d41}$, NR$^{c41}$R$^{d41}$, NR$^{c41}$C(O)R$^{b41}$, NR$^{c41}$C(O)OR$^{a41}$, NR$^{c41}$C(O)NR$^{c41}$R$^{d41}$, NR$^{c41}$S(O)R$^{b41}$, NR$^{c41}$S(O)$_2$R$^{b41}$, NR$^{c41}$S(O)$_2$NR$^{c41}$R$^{d41}$, S(O)R$^{b41}$, S(O)NR$^{c41}$R$^{d41}$, S(O)$_2$R$^{b41}$, S(O)$_2$NR$^{c41}$R$^{d41}$, and BR$^{h41}$R$^{i41}$;

each R$^{60}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$alkylene, halo, D, CN, NO$_2$, OR$^{a60}$, SR$^{a60}$, C(O)R$^{b60}$, C(O)NR$^{c60}$R$^{d60}$, C(O)OR$^{a60}$, OC(O)R$^{b60}$, OC(O)NR$^{c60}$R$^{d60}$, NR$^{c60}$R$^{d60}$, NR$^{c60}$C(O)R$^{b60}$, NR$^{c60}$C(O)OR$^{a60}$, NR$^{c60}$C(O)NR$^{c60}$R$^{d60}$, NR$^{c60}$S(O)R$^{b60}$, NR$^{c60}$S(O)$_2$R$^{b60}$, NR$^{c60}$S(O)$_2$NR$^{c60}$R$^{d60}$, S(O)R$^{b60}$, S(O)NR$^{c60}$R$^{d60}$, S(O)$_2$R$^{b60}$, S(O)$_2$NR$^{c60}$R$^{d60}$, and BR$^{h60}$R$^{i60}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$alkylene, C$_{6-10}$ aryl-C$_{1-3}$ alkylene and 5-10 membered heteroaryl-C$_{1-3}$ alkylene are each optionally substituted with 1, 2, 3, or 4 substituents independently selected from R$^{61}$;

each R$^{61}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, C$_{3-10}$ cycloalkyl-C$_{1-3}$ alkylene, 4-10 membered heterocycloalkyl-C$_{1-3}$ alkylene, C$_{6-10}$ aryl-C$_{1-3}$ alkylene, 5-10 membered heteroaryl-C$_{1-3}$alkylene, halo, D, CN, OR$^{a61}$, SR$^{a61}$, C(O)R$^{b61}$, C(O)NR$^{c61}$R$^{d61}$, C(O)OR$^{a61}$, OC(O)R$^{b61}$, OC(O)NR$^{c61}$R$^{d61}$, NR$^{c61}$R$^{d61}$, NR$^{c61}$C(O)R$^{b61}$, NR$^{c61}$C(O)OR$^{a61}$, NR$^{c61}$C(O)NR$^{c61}$R$^{d61}$, NR$^{c61}$S(O)R$^{b61}$, NR$^{c61}$S(O)$_2$R$^{b61}$, NR$^{c61}$S(O)$_2$NR$^{c61}$R$^{d61}$, S(O)R$^{b61}$, S(O)NR$^{c61}$R$^{d61}$, S(O)$_2$R$^{b61}$, S(O)$_2$NR$^{c61}$R$^{d61}$, and BR$^{h61}$R$^{i61}$;

each R$^a$, R$^b$, R$^c$ and R$^d$ is independently selected from H, C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl and 5-10 membered heteroaryl; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl and 5-10 membered heteroaryl, are each optionally substituted with 1, 2, 3, or 4 substituents independently selected from R$^{22}$;

or any R$^c$ and R$^d$ attached to the same N atom, together with the N atom to which they are attached, form a 4-, 5-, 6- or 7-membered heterocycloalkyl group optionally substituted with 1, 2, 3, or 4 substituents independently selected from R$^{22}$;

each R$^e$ is independently selected from H, CN, C$_{1-6}$ alkyl, C$_{2-6}$ alkenyl, C$_{2-6}$ alkynyl, C$_{1-6}$ haloalkyl, C$_{1-6}$ alkylthio, C$_{1-6}$ alkylsulfonyl, C$_{1-6}$ alkylcarbonyl, C$_{1-6}$ alkylaminosulfonyl, carbamyl, C$_{1-6}$ alkylcarbamyl, di(C$_{1-6}$ alkyl)carbamyl, aminosulfonyl, C$_{1-6}$ alkylaminosulfonyl and di(C$_{1-6}$ alkyl)aminosulfonyl;

each R$^h$ and R$^i$ is independently selected from OH, C$_{1-6}$ alkoxy, and C$_{1-6}$ haloalkoxy; or any R$^h$ and R$^i$ attached to the same B atom, together with the B atom to which they are attached, form a 5- or 6-membered heterocycloalkyl group optionally substituted with 1, 2, 3, or 4 substituents independently selected from C$_{1-6}$ alkyl and C$_{1-6}$ haloalkyl;

each R$^{a3}$, R$^{b3}$, R$^{c3}$ and R$^{d3}$ is independently selected from H, C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl and 5-10 membered heteroaryl;

or any $R^{c3}$ and $R^{d3}$ attached to the same N atom, together with the N atom to which they are attached, form a 4-, 5-, 6- or 7-membered heterocycloalkyl group;

each $R^{e3}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h3}$ and $R^{i3}$ is independently selected from OH, $C_{1-6}$ alkoxy, and $C_{1-6}$ haloalkoxy; or any $R^{h3}$ and $R^{i3}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a4}$, $R^{b4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c4}$ and $R^{d4}$ attached to the same N atom, together with the N atom to which they are attached, form a 4-, 5-, 6- or 7-membered heterocycloalkyl group optionally substituted with 1, 2, 3, or 4 substituents independently selected from $R^{40}$;

each $R^{e4}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h4}$ and $R^{i4}$ is independently selected from OH, $C_{1-6}$ alkoxy, and $C_{1-6}$ haloalkoxy; or any $R^{h4}$ and $R^{i4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{j4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c4}$ and $R^{j4}$ attached to the same N atom, together with the N atom to which they are attached, form a 4-, 5-, 6- or 7-membered heterocycloalkyl group optionally substituted with 1, 2, 3, or 4 substituents independently selected from $R^{40}$;

each $R^{a5}$, $R^{b5}$, $R^{c5}$, and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c5}$ and $R^{d5}$ attached to the same N atom, together with the N atom to which they are attached, form a 4-, 5-, 6- or 7-membered heterocycloalkyl group;

each $R^{e5}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h5}$ and $R^{i5}$ is independently selected from OH, $C_{1-6}$ alkoxy, and $C_{1-6}$ haloalkoxy; or any $R^{h5}$ and $R^{i5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a6}$, $R^{b6}$, $R^{c6}$, and $R^{d6}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^{60}$;

each $R^{e6}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h6}$ and $R^{i6}$ is independently selected from OH, $C_{1-6}$ alkoxy, and $C_{1-6}$ haloalkoxy; or any $R^{h6}$ and $R^{i6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a10}$, $R^{b10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

or any $R^{c10}$ and $R^{d10}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{e10}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h10}$ and $R^{i10}$ is independently selected from OH, $C_{1-6}$ alkoxy, and $C_{1-6}$ haloalkoxy; or any $R^{h10}$ and $R^{i10}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a11}$, $R^{b11}$, $R^{c11}$ and $R^{d11}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c11}$ and $R^{d11}$ attached to the same N atom, together with the N atom to which they are attached, form a 4-, 5-, 6- or 7-membered heterocycloalkyl group;

each $R^{h11}$ and $R^{i11}$ is independently selected from OH, $C_{1-6}$ alkoxy, and $C_{1-6}$ haloalkoxy; or any $R^{h11}$ and $R^{i11}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a20}$, $R^{b20}$, $R^{c20}$ and $R^{d20}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{21}$;

or any $R^{c20}$ and $R^{d20}$ attached to the same N atom, together with the N atom to which they are attached, form a 4-, 5-, 6- or 7-membered heterocycloalkyl group optionally substituted with 1, 2, 3, or 4 substituents independently selected from $R^{21}$;

each $R^{e20}$ is independently selected from H, CN, $C_{1-6}$ alkyl, $C_{2-6}$ alkenyl, $C_{2-6}$ alkynyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h20}$ and $R^{i20}$ is independently selected from OH, $C_{1-6}$ alkoxy, and $C_{1-6}$ haloalkoxy; or any $R^{h20}$ and $R^{i20}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a21}$, $R^{b21}$, $R^{c21}$ and $R^{d21}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$cycloalkyl, phenyl, 5-6 membered heteroaryl and 4-7 membered heterocycloalkyl are each optionally substituted with 1, 2, 3, or 4 substituents independently selected from $R^g$;

or any $R^{c21}$ and $R^{d21}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{h21}$ and $R^{i21}$ is independently selected from OH, $C_{1-6}$ alkoxy, and $C_{1-6}$ haloalkoxy; or any $R^{h21}$ and $R^{i21}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a22}$, $R^{b22}$, $R^{c22}$ and $R^{d22}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c22}$ and $R^{d22}$ attached to the same N atom, together with the N atom to which they are attached, form a 4-, 5-, 6- or 7-membered heterocycloalkyl group;

each $R^{h22}$ and $R^{i22}$ is independently selected from OH, $C_{1-6}$ alkoxy, and $C_{1-6}$ haloalkoxy; or any $R^{h22}$ and $R^{i22}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a40}$, $R^{b40}$, $R^{c40}$ and $R^{d40}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{41}$;

or any $R^{c40}$ and $R^{d40}$ attached to the same N atom, together with the N atom to which they are attached, form a 4-, 5-, 6- or 7-membered heterocycloalkyl group optionally substituted with 1, 2, 3, or 4 substituents independently selected from $R^{41}$;

each $R^{h40}$ and $R^{i40}$ is independently selected from OH, $C_{1-6}$ alkoxy, and $C_{1-6}$ haloalkoxy; or any $R^{h40}$ and $R^{i40}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a41}$, $R^{b41}$, $R^{c41}$ and $R^{d41}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c41}$ and $R^{d41}$ attached to the same N atom, together with the N atom to which they are attached, form a 4-, 5-, 6- or 7-membered heterocycloalkyl group;

each $R^{h41}$ and $R^{i41}$ is independently selected from OH, $C_{1-6}$ alkoxy, and $C_{1-6}$ haloalkoxy; or any $R^{h41}$ and $R^{i41}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each Raw, $R^{b60}$, $R^{c60}$ and $R^{d60}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{61}$;

or any $R^{c60}$ and $R^{d60}$ attached to the same N atom, together with the N atom to which they are attached, form a 4-, 5-, 6- or 7-membered heterocycloalkyl group optionally substituted with 1, 2, 3, or 4 substituents independently selected from $R^{61}$;

each $R^{h60}$ and $R^{i60}$ is independently selected from OH, $C_{1-6}$ alkoxy, and $C_{1-6}$ haloalkoxy; or any $R^{h60}$ and $R^{i60}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a61}$, $R^{b61}$, $R^{c61}$ and $R^{d61}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c61}$ and $R^{d61}$ attached to the same N atom, together with the N atom to which they are attached, form a 4-, 5-, 6- or 7-membered heterocycloalkyl group;

each $R^{h61}$ and $R^{i61}$ is independently selected from OH, $C_{1-6}$ alkoxy, and $C_{1-6}$ haloalkoxy; or any $R^{h61}$ and $R^{i61}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^g$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

3. The compound of claim 1, or pharmaceutically acceptable salt thereof, wherein ≡ represents a single bond or a double bond;

X is N or $CR^5$;

Y is N or $CR^6$;

each R is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $NR^cS(O)_2R^b$, $NR^cS(O)_2NR^cR^d$, $S(O)_2R^b$, and $S(O)_2NR^cR^d$;

n is 0, 1, 2, 3, or 4;

$Cy^1$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

$R^{3A}$ and $R^{3B}$ are each independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$;

or $R^{3A}$ and $R^{3B}$ can be taken together with the carbon atom to which they are attached to form a C=O;

$R^4$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{40}$;

$R^5$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)_2R^{b5}$, $NR^{c5}S(O)_2NR^{c5}R^{d5}$, $S(O)_2R^{b5}$, and $S(O)_2NR^{c5}R^{d5}$;

$R^6$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)_2R^{b6}$, $NR^{c6}S(O)_2NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{60}$;

$Cy^2$ is selected from $C_{3-10}$ cycloalkyl, 4-14 membered heterocycloalkyl, $C_{6-10}$ aryl and 5-10 membered heteroaryl; wherein the 4-14 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-14 membered heterocycloalkyl is optionally substituted by oxo to form a carbonyl group; and wherein the $C_{3-10}$ cycloalkyl, 4-14 membered heterocycloalkyl, $C_{6-10}$ aryl and 5-10 membered heteroaryl are each optionally substituted with 1, 2, 3 or 4 substituents independently selected from $R^{20}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a10}$, $SR^{a10}$, $C(O)R^{b10}$, $C(O)NR^{c10}R^{d10}$, $C(O)OR^{a10}$, $OC(O)R^{b10}$, $OC(O)NR^{c10}R^{d10}$, $NR^{c10}R^{d10}$, $NR^{c10}C(O)R^{b10}$, $NR^{c10}C(O)OR^{a10}$, $NR^{c10}C(O)NR^{c10}R^{d10}$, $NR^{c10}S(O)_2R^{b10}$, $NR^{c10}S(O)_2NR^{c10}R^{d10}$, $S(O)_2R^{b10}$, and $S(O)_2NR^{c10}R^{d10}$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a20}$, $SR^{a20}$, $C(O)R^{b20}$, $C(O)NR^{c20}R^{d20}$, $C(O)OR^{a20}$, $OC(O)R^{b20}$, $OC(O)NR^{c20}R^{d20}$, $NR^{c20}R^{d20}$, $NR^{c20}C(O)R^{b20}$, $NR^{c20}C(O)OR^{a20}$, $NR^{c20}C(O)NR^{c20}R^{d20}$, $NR^{c20}S(O)_2R^{b20}$, $NR^{c20}S(O)_2NR^{c20}R^{d20}$, $S(O)_2R^{b20}$, and $S(O)_2NR^{c20}R^{d20}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$alkylene, halo, D, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)_2R^{b21}$, $NR^{c21}S(O)_2NR^{c21}R^{d21}$, $S(O)_2R^{b21}$, and $S(O)_2NR^{c21}R^{d21}$;

each $R^{40}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a40}$, $SR^{a40}$, $C(O)R^{b40}$, $C(O)NR^{40}R^{d40}$, $C(O)OR^{a40}C(O)R^{b40}$, $OC(O)NR^{c10}R^{d40}$, $NR^{40}R^{d40}$, $NR^{c40}C(O)R^{b40}$, $NR^{c40}C(O)OR^{a40}$, $NR^{c40}C(O)NR^{c40}R^{d40}$, $NR^{c40}S(O)_2R^{b40}$, $NR^{c40}S(O)_2NR^{c40}R^{d40}$, $S(O)_2R^{b40}$, and $S(O)_2NR^{c40}R^{d40}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{41}$;

each $R^{41}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d41}$, $NR^{c41}S(O)_2R^{b41}$, $NR^{c41}S(O)_2NR^{c41}R^{d41}$, $S(O)_2R^{b41}$, and $S(O)_2NR^{c41}R^{d41}$;

each $R^{60}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a60}$, $SR^{a60}$, $C(O)R^{b60}$, $C(O)NR^{c60}R^{d60}$, $C(O)OR^{a60}$, $OC(O)R^{b60}$, $OC(O)NR^{c60}R^{d60}$, $NR^{c60}R^{d60}$, $NR^{c60}C(O)R^{b60}$, $NR^{c60}C(O)OR^{a60}$, $NR^{c60}C(O)NR^{c60}R^{d60}$, $NR^{c60}S(O)_2R^{b60}$, $NR^{c60}S(O)_2NR^{c60}R^{d60}$, $S(O)_2R^{b60}$, and $S(O)_2NR^{c60}R^{d60}$;

each $R^a$, $R^b$, $R^c$ and $R^d$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^c$ and $R^d$ attached to the same N atom, together with the N atom to which they are attached, form a 4-, 5-, 6- or 7-membered heterocycloalkyl group;

each $R^{a3}$, $R^{b3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c3}$ and $R^{d3}$ attached to the same N atom, together with the N atom to which they are attached, form a 4-, 5-, 6- or 7-membered heterocycloalkyl group;

each $R^{a4}$, $R^{b4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c4}$ and $R^{d4}$ attached to the same N atom, together with the N atom to which they are attached, form a 4-, 5-, 6- or 7-membered heterocycloalkyl group optionally substituted with 1, 2, 3, or 4 substituents independently selected from $R^{40}$;

each $R^{j4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c4}$ and $R^{j4}$ attached to the same N atom, together with the N atom to which they are attached, form a 4-, 5-, 6- or 7-membered heterocycloalkyl group optionally substituted with 1, 2, 3, or 4 substituents independently selected from $R^{40}$;

each $R^{a5}$, $R^{b5}$, $R^{c5}$, and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c5}$ and $R^{d5}$ attached to the same N atom, together with the N atom to which they are attached, form a 4-, 5-, 6- or 7-membered heterocycloalkyl group;

each $R^{a6}$, $R^{b6}$, $R^{c6}$, and $R^{d6}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^{60}$;

each $R^{a10}$, $R^{b10}$, $R^{c10}$ and $R^{d10}$ is independently selected from H, $C_{1-6}$ alkyl, $C_{2-6}$ alkenyl, $C_{2-6}$ alkynyl, $C_{1-6}$ haloalkyl, $C_{3-10}$cycloalkyl, 4-10 membered heterocycloalkyl, $C_{6-10}$ aryl and 5-10 membered heteroaryl;

or any $R^{c10}$ and $R^{d10}$ attached to the same N atom, together with the N atom to which they are attached, form a 4-, 5-, 6- or 7-membered heterocycloalkyl group;

each $R^{a20}$, $R^{b20}$, $R^{c20}$ and $R^{d20}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{21}$;

or any $R^{c20}$ and $R^{d20}$ attached to the same N atom, together with the N atom to which they are attached, form a 4-, 5-, 6- or 7-membered heterocycloalkyl group optionally substituted with 1, 2, 3, or 4 substituents independently selected from $R^{21}$;

each $R^{a21}$, $R^{b21}$, $R^{c21}$ and $R^{d21}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c21}$ and $R^{d21}$ attached to the same N atom, together with the N atom to which they are attached, form a 4-, 5-, 6- or 7-membered heterocycloalkyl group;

each $R^{a40}$, $R^{b40}$, $R^{c40}$ and $R^{d40}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{41}$;

or any $R^{c40}$ and $R^{d40}$ attached to the same N atom, together with the N atom to which they are attached, form a 4-, 5-, 6- or 7-membered heterocycloalkyl group optionally substituted with 1, 2, 3, or 4 substituents independently selected from $R^{41}$;

each $R^{a41}$, $R^{b41}$, $R^{c41}$ and $R^{d41}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl;

or any $R^{c41}$ and $R^{d41}$ attached to the same N atom, together with the N atom to which they are attached, form a 4-, 5-, 6- or 7-membered heterocycloalkyl group; and each $R^{a60}$, $R^{b60}$, $R^{c60}$ and $R^{d60}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

or any $R^{c60}$ and $R^{d60}$ attached to the same N atom, together with the N atom to which they are attached, form a 4-, 5-, 6- or 7-membered heterocycloalkyl group.

4. The compound of claim 1, or a pharmaceutically acceptable salt thereof, wherein === represents a single bond or a double bond;

X is N;

Y is N or $CR^6$;

each R is independently selected from $C_{1-6}$ alkyl, $C_{1-6}$ haloalkyl, halo, D, CN, $OR^a$, and $NR^cR^d$;

n is 0, 1, or 2;

$Cy^1$ is selected from $C_{6-10}$ aryl and 5-10 membered heteroaryl; wherein the 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, 3 or 4 substituents independently selected from $R^{10}$;

$R^{3A}$ and $R^{3B}$ are each independently selected from H, $C_{1-6}$ alkyl, $C_{1-6}$ haloalkyl, halo, D, CN, $OR^{a3}$, and $NR^{c3}R^{d3}$;

or $R^{3A}$ and $R^{3B}$ can be taken together with the carbon atom to which they are attached to form a C=O;

$R^4$ is selected from H, $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{j4}$, and $NR^{c4}C(O)R^{b4}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{40}$;

$R^6$ is selected from H, $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a6}$, and $NR^{c6}R^{d6}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{60}$;

$Cy^2$ is selected from $C_{3-10}$ cycloalkyl, and 4-14 membered heterocycloalkyl; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group; and wherein the $C_{3-10}$ cycloalkyl, and 4-14 membered heterocycloalkyl, are each optionally substituted with 1, 2, 3 or 4 substituents independently selected from $R^{20}$;

each $R^{10}$ is independently selected from $C_{1-6}$ alkyl, $C_{1-6}$ haloalkyl, halo, D, CN, $OR^{a10}$, and $NR^{c10}R^{d10}$;

each $R^{20}$ is independently selected from $C_{1-6}$ alkyl, $C_{2-6}$ alkenyl, $C_{2-6}$ alkynyl, $C_{1-6}$ haloalkyl, halo, D, CN, $OR^{a20}$, $C(O)R^{b20}$, $C(O)NR^{c20}R^{d20}$, and $NR^{c20}R^{d20}$; wherein said $C_{1-6}$ alkyl, is optionally substituted with 1, 2, 3, or 4 substituents independently selected from $R^{21}$;

each $R^{21}$ is independently selected from $C_{1-6}$ alkyl, $C_{1-6}$ haloalkyl, halo, D, CN, $OR^{a21}$, and $NR^{c21}R^{d21}$;

each $R^{40}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a40}$, and $NR^{c40}R^{d40}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{41}$;

each $R^{41}$ is independently selected from $C_{1-6}$ alkyl, $C_{1-6}$ haloalkyl, halo, D, CN, $OR^{a41}$, and $NR^{c41}R^{d41}$;

each $R^{60}$ is independently selected from $C_{1-6}$ alkyl, $C_{1-6}$ haloalkyl, halo, D, CN, $OR^{a60}$, and $NR^{c60}R^{d60}$;

each $R^a$, $R^c$ and $R^d$ is independently selected from H, $C_{1-6}$ alkyl, and $C_{1-6}$ haloalkyl;

each $R^{a3}$, $R^{c3}$ and $R^{d3}$ is independently selected from H, $C_{1-6}$ alkyl, and $C_{1-6}$ haloalkyl;

each $R^{a4}$, $R^{b4}$, $R^{c4}$ and $R^{d4}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c4}$ and $R^{d4}$ attached to the same N atom, together with the N atom to which they are attached, form a 4-, 5-, 6- or 7-membered heterocycloalkyl group optionally substituted with 1, 2, 3, or 4 substituents independently selected from $R^{40}$;

each $R^{j4}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c4}$ and $R^{j4}$ attached to the same N atom, together with the N atom to which they are attached, form a 4-, 5-, 6- or 7-membered heterocycloalkyl group optionally substituted with 1, 2, 3, or 4 substituents independently selected from $R^{40}$;

each $R^{a6}$, $R^{c6}$, and $R^{d6}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{60}$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^{60}$;

each $R^{a10}$, $R^{c10}$ and $R^{d10}$ is independently selected from H, $C_{1-6}$ alkyl, and $C_{1-6}$ haloalkyl;

each $R^{a20}$, $R^{b20}$, $R^{c20}$ and $R^{d20}$ is independently selected from H, $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, $C_{2-6}$ alkynyl, are each optionally substituted with 1, 2, 3, or 4 substituents independently selected from $R^{21}$;

each $R^{a21}$, $R^{c21}$ and $R^{d21}$, is independently selected from H, $C_{1-6}$ alkyl, and $C_{1-6}$ haloalkyl;

each $R^{a40}$, $R^{c40}$ and $R^{d40}$ is independently selected from H, $C_{1-6}$ alkyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{41}$;

or any $R^{c40}$ and $R^{d40}$ attached to the same N atom, together with the N atom to which they are attached, form a 4-, 5-, 6- or 7-membered heterocycloalkyl group optionally substituted with 1, 2, 3, or 4 substituents independently selected from $R^{41}$;

each $R^{a41}$, $R^{c41}$ and $R^{d41}$, is independently selected from H, $C_{1-6}$ alkyl, and $C_{1-6}$ haloalkyl; and each $R^{a60}$, $R^{c60}$ and $R^{d60}$ is independently selected from H, $C_{1-6}$ alkyl, and $C_{1-6}$ haloalkyl.

5. The compound of claim 1, wherein the compound of Formula I is a compound of Formula II:

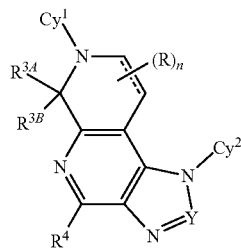

(II)

or a pharmaceutically acceptable salt thereof.

6. The compound of claim 1, or a pharmaceutically acceptable salt thereof, wherein:

=== represents a single bond or a double bond;

Y is N or $CR^6$;

each R is independently selected from $C_{1-6}$ alkyl, $C_{1-6}$ haloalkyl, halo, D, and CN;

n is 0, 1, or 2;

$Cy^1$ is selected from $C_{6-10}$ aryl and 5-10 membered heteroaryl; wherein the 5-10 membered heteroaryl each has at least one ring-forming carbon atom and 1 or 2 ring-forming heteroatoms independently selected from N and O; and wherein the $C_{6-10}$ aryl and 5-10 membered heteroaryl are each optionally substituted with 1, 2, or 3 substituents independently selected from $R^{10}$;

$R^{3A}$ and $R^{3B}$ are each independently selected from H, $C_{1-6}$ alkyl, $C_{1-6}$ haloalkyl, halo, D, and CN;

or $R^{3A}$ and $R^{3B}$ can be taken together with the carbon atom to which they are attached to form a C=O;

$R^4$ is selected from H, $C_{1-6}$ alkyl, $C_{1-6}$ haloalkyl, $C_{3-6}$ cycloalkyl, 4-6 membered heterocycloalkyl, phenyl, 5-6 membered heteroaryl, halo, D, CN, $OR^{a4}$, and $NR^{c4}R^{j4}$; wherein said $C_{1-6}$ alkyl, $C_{3-6}$ cycloalkyl, 4-6 membered heterocycloalkyl, phenyl, and 5-6 membered heteroaryl, are each optionally substituted with 1, 2, or 3 substituents independently selected from $R^{40}$;

$R^6$ is selected from H, $C_{1-6}$ alkyl, $C_{1-6}$ haloalkyl, halo, D, CN, $OR^{a6}$, and $NR^{c6}R^{d6}$; wherein said $C_{1-6}$ alkyl, is optionally substituted with 1, 2, or 3 substituents independently selected from $R^{60}$;

$Cy^2$ is selected from 4-8 membered heterocycloalkyl; wherein the 4-8 membered heterocycloalkyl has at least one ring-forming carbon atom and 1 or 2 ring-forming heteroatoms independently selected from N and O; and wherein the 4-8 membered heterocycloalkyl, is optionally substituted with 1, 2, or 3 substituents independently selected from $R^{20}$;

each $R^{10}$ is independently selected from $C_{1-6}$ alkyl, $C_{1-6}$ haloalkyl, halo, D, CN, $OR^{a10}$, and $NR^{c10}R^{d10}$;

each $R^{20}$ is independently selected from $C_{1-6}$ alkyl, $C_{2-6}$ alkenyl, $C_{2-6}$ alkynyl, $C_{1-6}$ haloalkyl, halo, D, CN, $OR^{a20}$, $C(O)R^{b20}$, $C(O)NR^{c20}R^{d20}$, and $NR^{c20}R^{d20}$; wherein said $C_{1-6}$ alkyl, is optionally substituted with 1, 2, 3, or 4 substituents independently selected from $R^{21}$;

each $R^{21}$ is independently selected from $C_{1-6}$ alkyl, $C_{1-6}$ haloalkyl, halo, D, CN, $OR^{a21}$, and $NR^{c21}R^{d21}$;

each $R^{40}$ is independently selected from $C_{1-6}$ alkyl, $C_{1-6}$ haloalkyl, $C_{3-6}$ cycloalkyl, 4-6 membered heterocycloalkyl, halo, D, CN, $OR^{a40}$, and $NR^{c40}R^{d40}$; wherein said $C_{1-6}$ alkyl, $C_{3-6}$ cycloalkyl, and 4-6 membered heterocycloalkyl, are each optionally substituted with 1, 2, or 3 substituents independently selected from $R^{41}$;

each $R^{41}$ is independently selected from $C_{1-6}$ alkyl, $C_{1-6}$ haloalkyl, halo, D, and CN;

each $R^{60}$ is independently selected from $C_{1-6}$ alkyl, $C_{1-6}$ haloalkyl, halo, D, CN, $OR^{a60}$, and $NR^{c60}R^{d60}$;

each $R^{a4}$, and $R^{c4}$ is independently selected from H, $C_{1-6}$ alkyl, $C_{1-6}$ haloalkyl, $C_{3-6}$ cycloalkyl, 4-6 membered heterocycloalkyl, phenyl and 5-6 membered heteroaryl; wherein said $C_{1-6}$ alkyl, $C_{3-6}$ cycloalkyl, 4-6 membered heterocycloalkyl, phenyl and 5-6 membered heteroaryl, are each optionally substituted with 1, 2, or 3 substituents independently selected from $R^{40}$;

each $R^{j4}$ is independently selected from H, $C_{1-6}$ alkyl, $C_{1-6}$ haloalkyl, $C_{3-6}$ cycloalkyl, 4-6 membered heterocycloalkyl, phenyl and 5-6 membered heteroaryl; wherein said $C_{1-6}$ alkyl, $C_{3-6}$ cycloalkyl, 4-6 membered heterocycloalkyl, phenyl and 5-6 membered heteroaryl, are each optionally substituted with 1, 2, 3, or 4 substituents independently selected from $R^{40}$;

or any $R^{c4}$ and $R^{j4}$ attached to the same N atom, together with the N atom to which they are attached, form a 4-, 5-, or 6-membered heterocycloalkyl group optionally substituted with 1, 2, 3, or 4 substituents independently selected from $R^{40}$;

each $R^{a6}$, $R^{c6}$, and $R^{d6}$ is independently selected from H, $C_{1-6}$ alkyl, and $C_{1-6}$ haloalkyl; wherein said $C_{1-6}$ alkyl is optionally substituted with 1, 2, or 3 substituents independently selected from $R^{60}$;

each $R^{a10}$, $R^{c10}$ and $R^{d10}$ is independently selected from H, $C_{1-6}$ alkyl, and $C_{1-6}$ haloalkyl;

each $R^{a20}$, $R^{b20}$, $R^{c20}$ and $R^{d20}$ is independently selected from H, $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl, are each optionally substituted with 1, 2, 3, or 4 substituents independently selected from $R^{21}$;

each $R^{a21}$, $R^{c21}$ and $R^{d21}$, is independently selected from H, $C_{1-6}$ alkyl, and $C_{1-6}$ haloalkyl;

each $R^{a40}$, $R^{c40}$ and $R^{d40}$ is independently selected from H, $C_{1-6}$ alkyl, $C_{1-6}$ haloalkyl, $C_{3-6}$ cycloalkyl, and 4-6 membered heterocycloalkyl; wherein said $C_{1-6}$ alkyl, $C_{3-6}$ cycloalkyl, and 4-6 membered heterocycloalkyl, are each optionally substituted with 1, 2, or 3 substituents independently selected from $R^{41}$;

or any $R^{c40}$ and $R^{d40}$ attached to the same N atom, together with the N atom to which they are attached, form a 4-, 5-, or 6-membered heterocycloalkyl group optionally substituted with 1, 2, or 3 substituents independently selected from $R^{41}$; and each $R^{a60}$, $R^{c60}$ and $R^{d60}$ is independently selected from H, $C_{1-6}$ alkyl, and $C_{1-6}$ haloalkyl.

7. The compound of claim 1, or a pharmaceutically acceptable salt thereof, wherein === represents a single bond or a double bond;

X is N;

Y is N, CH, or C($C_{1-6}$ alkyl) optionally substituted with 1, 2, 3, or 4 substituents independently selected from $R^{60}$;

R is $C_{1-6}$ haloalkyl;

n is 0 or 1;

$Cy^1$ is $C_{6-10}$ aryl optionally substituted with 1 or 2 substituents independently selected from $R^{10}$;

$R^{3A}$ and $R^{3B}$ are H;

or $R^{3A}$ and $R^{3B}$ can be taken together with the carbon atom to which they are attached to form a C=O;

$R^4$ is selected from $OR^{a4}$, 4-6 membered heterocycloalkyl, and 5-6 membered heteroaryl, wherein said heterocycloalkyl and heteroaryl are each optionally substituted with 1, 2, 3, or 4 substituents independently selected from $R^{40}$;

$Cy^2$ is 4-8 membered heterocycloalkyl optionally substituted with 1, 2, or 3 substituents independently selected from $R^{20}$;

each $R^{10}$ is independently selected from $C_{1-6}$ alkyl, $C_{1-6}$ haloalkyl, halo, and OH;

each $R^{20}$ is independently selected from $C_{1-6}$ alkyl, $C_{1-6}$ haloalkyl, and $C(O)R^{b20}$, wherein said alkyl is optionally substituted with 1 or 2 substituents independently selected from $R^{21}$;

each $R^{21}$ is independently selected from $C_{1-6}$ haloalkyl, halo, CN, OH, and $NH_2$;

$R^{40}$ is independently selected from $C_{1-6}$ alkyl, OH, O($C_{1-6}$ alkyl), N($C_{1-6}$ alkyl)$_2$, NH($C_{1-6}$ alkyl), $NH_2$, and 4-6 membered heterocycloalkyl, wherein heterocycloalkyl is optionally substituted by $C_{1-6}$ alkyl;

each $R^{60}$ is independently selected from $C_{1-6}$ alkyl, $C_{1-6}$ haloalkyl, halo, CN, $OR^{a60}$, and $NR^{c60}R^{d60}$;

$R^{a4}$ is independently selected from H, $C_{1-6}$ alkyl, and $C_{1-6}$ haloalkyl, wherein $C_{1-6}$ alkyl is optionally substituted by $R^{40}$;

each $R^{b20}$ is independently selected from $C_{1-6}$ alkyl, $C_{2-6}$ alkenyl, and $C_{2-6}$ alkynyl; wherein said $C_{1-6}$ alkyl, $C_{2-6}$ alkenyl, and $C_{2-6}$ alkynyl, are each optionally substituted with halo; and each $R^{a60}$, $R^{c60}$ and $R^{d60}$ is independently selected from H and $C_{1-6}$ alkyl.

8. The compound of claim 1, wherein the compound of Formula I is a compound of Formula III:

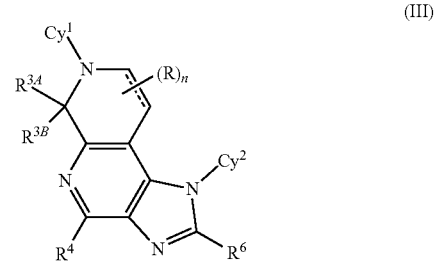

(III)

or a pharmaceutically acceptable salt thereof.

9. The compound of claim 1, wherein the compound of Formula I is a compound of Formula IIIa:

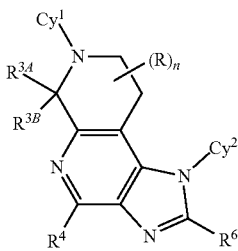

(IIIa)

or a pharmaceutically acceptable salt thereof.

10. The compound of claim 1, wherein the compound of Formula I is a compound of Formula IIIb:

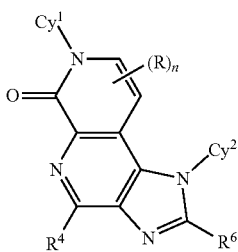

(IIIb)

or a pharmaceutically acceptable salt thereof.

11. The compound of claim 1, wherein the compound of Formula I is a compound of Formula IV:

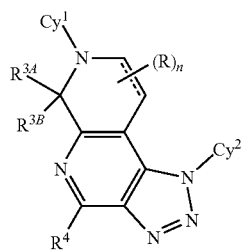

(IV)

or a pharmaceutically acceptable salt thereof.

12. The compound of claim 1, or a pharmaceutically acceptable salt thereof, wherein === represents a single bond.

13. The compound of claim 1, or a pharmaceutically acceptable salt thereof, wherein === represents a double bond.

14. The compound of claim 1, or a pharmaceutically acceptable salt thereof, wherein X is N.

15. The compound of claim 1, or a pharmaceutically acceptable salt thereof, wherein Y is CH or C($C_{1-6}$ alkyl) wherein $C_{1-6}$ alkyl is optionally substituted with 1, 2, 3, or 4 substituents independently selected from $R^{60}$.

16. The compound of claim 1, or a pharmaceutically acceptable salt thereof, wherein Y is N.

17. The compound of claim 1, or a pharmaceutically acceptable salt thereof, wherein n is 0.

18. The compound of claim 1, or a pharmaceutically acceptable salt thereof, wherein R is $C_{1-6}$ haloalkyl and n is 1.

19. The compound of claim 1, or a pharmaceutically acceptable salt thereof, wherein $Cy^1$ is $C_{6-10}$ aryl optionally substituted with 1 or 2 substituents independently selected from $R^{10}$.

20. The compound of claim 1, or a pharmaceutically acceptable salt thereof, wherein each $R^{10}$ is independently selected from $C_{1-6}$ alkyl, halo, and OH.

21. The compound of claim 1, or a pharmaceutically acceptable salt thereof, wherein $R^{3A}$ and $R^{3B}$ are taken together with the carbon atom to which they are attached to form a C=O.

22. The compound of claim 1, or a pharmaceutically acceptable salt thereof, wherein $R^{3A}$ and $R^{3B}$ are each H.

23. The compound of claim 1, or a pharmaceutically acceptable salt thereof, wherein $R^4$ is selected from $OR^{a4}$, 4-6 membered heterocycloalkyl, and 5-6 membered heteroaryl, wherein said heterocycloalkyl and heteroaryl are each optionally substituted with 1, 2, or 3 substituents independently selected from $R^{40}$.

24. The compound of claim 1, or a pharmaceutically acceptable salt thereof, wherein each $R^{40}$ is independently selected from $C_{1-6}$ alkyl, $N(C_{1-6}$ alkyl$)_2$, $NH(C_{1-6}$ alkyl), $NH_2$, and 4-6 membered heterocycloalkyl wherein heterocycloalkyl is optionally substituted with $R^{41}$.

25. The compound of claim 1, or a pharmaceutically acceptable salt thereof, wherein each $R^{a4}$ is independently selected from $C_{1-6}$ alkyl substituted with 4-6 membered heterocycloalkyl, wherein said heterocycloalkyl is optionally substituted with $C_{1-6}$ alkyl.

26. The compound of claim 1, or a pharmaceutically acceptable salt thereof, wherein $Cy^2$ is 4-8 membered heterocycloalkyl optionally substituted with 1, 2, or 3 substituents independently selected from $R^{20}$.

27. The compound of claim 1, or a pharmaceutically acceptable salt thereof, wherein each $R^{20}$ is independently selected from $C_{1-6}$ alkyl and $C(O)R^{b20}$, wherein said alkyl is optionally substituted with 1 or 2 substituents independently selected from $R^{21}$.

28. The compound of claim 1, or a pharmaceutically acceptable salt thereof, wherein each $R^{21}$ is independently selected from $C_{1-6}$ haloalkyl, halo, CN, OH, and $NH_2$.

29. The compound of claim 1, or a pharmaceutically acceptable salt thereof, wherein each $R^{b20}$ is independently selected from $C_{1-6}$ alkyl, $C_{2-6}$ alkenyl, and $C_{2-6}$ alkynyl; wherein said $C_{1-6}$ alkyl, $C_{2-6}$ alkenyl, and $C_{2-6}$ alkynyl, are each optionally substituted with halo.

30. The compound of claim 1, wherein the compound of Formula I is selected from:
 2-((2S,4S)-1-acryloyl-4-(4-(3-(dimethylamino)azetidin-1-yl)-7-(3-hydroxynaphthalen-1-yl)-6-oxo-6,7-dihydro-1H-imidazo[4,5-c][1,7]naphthyridin-1-yl)piperidin-2-yl)acetonitrile;
 2-((2S,4S)-1-(but-2-ynoyl)-4-(4-(3-(dimethylamino)azetidin-1-yl)-7-(3-hydroxynaphthalen-1-yl)-6-oxo-6,7-dihydro-1H-imidazo[4,5-c][1,7]naphthyridin-1-yl)piperidin-2-yl)acetonitrile;
 1-((1R,4R,5S)-2-azabicyclo[2.1.1]hexan-5-yl)-4-(3-(dimethylamino)azetidin-1-yl)-7-(3-hydroxynaphthalen-1-yl)-2-(2-(methylamino)ethyl)-1,7-dihydro-6H-imidazo[4,5-c][1,7]naphthyridin-6-one;
 2-((2S,4S)-1-acryloyl-4-(4-(3-(dimethylamino)azetidin-1-yl)-7-(naphthalen-1-yl)-6,7,8,9-tetrahydro-1H-imidazo[4,5-c][1,7]naphthyridin-1-yl)piperidin-2-yl)acetonitrile;

2-((2S,4S)-1-acryloyl-4-(4-(3-(dimethylamino)azetidin-1-yl)-7-(3-hydroxynaphthalen-1-yl)-6,7,8,9-tetrahydro-1H-imidazo[4,5-c][1,7]naphthyridin-1-yl)piperidin-2-yl)acetonitrile;

2-((2S,4S)-1-acryloyl-4-(4-(3-(dimethylamino)azetidin-1-yl)-7-(naphthalen-1-yl)-6-oxo-8-(trifluoromethyl)-6,7-dihydro-1H-imidazo[4,5-c][1,7]naphthyridin-1-yl)piperidin-2-yl)acetonitrile;

2-((2S)-1-acryloyl-4-(4-(2-methylpyridin-3-yl)-7-(naphthalen-1-yl)-6-oxo-8-(trifluoromethyl)-6,7-dihydro-1H-imidazo[4,5-c][1,7]naphthyridin-1-yl)piperidin-2-yl)acetonitrile;

2-((2S,4S)-1-acryloyl-4-(7-(3-chloro-2-methylphenyl)-4-((S)-1-((S)-1-methylpyrrolidin-2-yl)ethoxy)-6-oxo-8-(trifluoromethyl)-6,7-dihydro-1H-imidazo[4,5-c][1,7]naphthyridin-1-yl)piperidin-2-yl)acetonitrile;

2-((2S,4S)-1-(but-2-ynoyl)-4-(7-(3-chloro-2-methylphenyl)-4-((S)-1-((S)-1-methylpyrrolidin-2-yl)ethoxy)-6-oxo-8-(trifluoromethyl)-6,7-dihydro-1H-imidazo[4,5-c][1,7]naphthyridin-1-yl)piperidin-2-yl)acetonitrile;

2-((2S,4S)-4-(7-(3-chloro-2-methylphenyl)-4-((S)-1-((S)-1-methylpyrrolidin-2-yl)ethoxy)-6-oxo-8-(trifluoromethyl)-6,7-dihydro-1H-imidazo[4,5-c][1,7]naphthyridin-1-yl)-1-(2-fluoroacryloyl)piperidin-2-yl)acetonitrile;

2-((2S,4S)-1-acryloyl-4-(7-(3-chloro-2-methylphenyl)-4-(3-(dimethylamino)-3-methylazetidin-1-yl)-6-oxo-8-(trifluoromethyl)-6,7-dihydro-1H-[1,2,3]triazolo[4,5-c][1,7]naphthyridin-1-yl)piperidin-2-yl)acetonitrile; and 2-((2S,4S)-4-(7-(3-chloro-2-methylphenyl)-4-(3-(dimethylamino)-3-methylazetidin-1-yl)-6-oxo-8-(trifluoromethyl)-6,7-dihydro-1H-[1,2,3]triazolo[4,5-c][1,7]naphthyridin-1-yl)-1-((E)-4-fluorobut-2-enoyl)piperidin-2-yl)acetonitrile;

or a pharmaceutically acceptable salt thereof.

31. A pharmaceutical composition comprising the compound claim 1, or a pharmaceutically acceptable salt thereof, and a pharmaceutically acceptable carrier.

32. A method of inhibiting KRAS activity in a subject in need thereof comprising administering to the subject a therapeutically effective amount of the compound of claim 1.

33. A method of treating a KRAS-mediated disease or disorder in a subject in need thereof comprising administering to the subject a therapeutically effective amount of the compound of claim 1.

34. The method of claim 33, wherein the disease or disorder is an immunological or inflammatory disorder.

35. The method of claim 34, wherein the immunological or inflammatory disorder is Ras-associated lymphoproliferative disorder or juvenile myelomonocytic leukemia caused by somatic mutations of KRAS.

36. The method of claim 33, wherein the disease or disorder is a cancer.

37. The method of claim 36, wherein the cancer is selected from carcinomas, hematological cancers, sarcomas, and glioblastoma.

38. The method of claim 37, wherein the cancer is a hematological cancer selected from myeloproliferative neoplasms, myelodysplastic syndrome, chronic and juvenile myelomonocytic leukemia, acute myeloid leukemia, acute lymphocytic leukemia, and multiple myeloma.

39. The method of claim 37, wherein the cancer is a carcinoma selected from pancreatic, colorectal, lung, bladder, gastric, esophageal, breast, head and neck, cervical, skin, and thyroid carcinomas.

40. A method of treating a disease or disorder associated with KRAS protein harboring a G12C mutation, said method comprising administering to a patient in need thereof a therapeutically effective amount of the compound of claim 1.

41. A method of treating cancer in a subject, in need thereof comprising administering to the subject a therapeutically effective amount of the compound of claim 1, wherein the cancer is a pancreatic cancer, colorectal cancer or lung cancer.

42. The method of claim 36, wherein the cancer is a pancreatic cancer, colorectal cancer or lung cancer.

* * * * *

UNITED STATES PATENT AND TRADEMARK OFFICE
CERTIFICATE OF CORRECTION

PATENT NO.        : 12,077,539 B2                                                   Page 1 of 1
APPLICATION NO.   : 17/700923
DATED             : September 3, 2024
INVENTOR(S)       : Chao Qi et al.

It is certified that error appears in the above-identified patent and that said Letters Patent is hereby corrected as shown below:

In the Claims

Column 142, Line 45, Claim 2, delete "Raw" and insert -- $R^{a60}$ --.

Signed and Sealed this
Eleventh Day of February, 2025

Coke Morgan Stewart
*Acting Director of the United States Patent and Trademark Office*